United States Patent
Malamas et al.

(10) Patent No.: US 10,689,357 B2
(45) Date of Patent: Jun. 23, 2020

(54) N-ACYLETHANOLAMINE HYDROLYZING ACID AMIDASE (NAAA) INHIBITORS AND USE THEREOF

(71) Applicant: Northeastern University, Boston, MA (US)

(72) Inventors: Michael S. Malamas, Jamison, PA (US); Alexandros Makriyannis, Watertown, MA (US); Shrouq I. Farah, Everett, MA (US); Alexander M. Zvonok, Revere, MA (US); Shakiru Olajire Alapafuja, Braintree, MA (US)

(73) Assignee: NORTHEASTERN UNIVERSITY, Boston, MA (US)

( * ) Notice: Subject to any disclaimer, the term of this patent is extended or adjusted under 35 U.S.C. 154(b) by 0 days.

(21) Appl. No.: 16/406,613

(22) Filed: May 8, 2019

(65) Prior Publication Data

US 2019/0345132 A1 Nov. 14, 2019

Related U.S. Application Data

(60) Provisional application No. 62/668,789, filed on May 8, 2018.

(51) Int. Cl.
| | | |
|---|---|---|
| *C07D 401/04* | (2006.01) | |
| *C07C 331/26* | (2006.01) | |
| *C07D 205/04* | (2006.01) | |
| *C07D 213/16* | (2006.01) | |
| *C07D 263/34* | (2006.01) | |
| *C07F 9/58* | (2006.01) | |

(52) U.S. Cl.
CPC .......... *C07D 401/04* (2013.01); *C07C 331/26* (2013.01); *C07D 205/04* (2013.01); *C07D 213/16* (2013.01); *C07D 263/34* (2013.01); *C07F 9/58* (2013.01)

(58) Field of Classification Search
CPC .......................... C07D 401/04; C07C 331/26
See application file for complete search history.

(56) References Cited

U.S. PATENT DOCUMENTS

| | | |
|---|---|---|
| 2,866,804 A | 12/1958 | Nischk et al. |
| 3,671,638 A | 6/1972 | Knowles |
| 3,822,269 A | 7/1974 | Jeanmart et al. |
| 4,001,254 A | 1/1977 | Schmid et al. |
| 6,124,323 A | 9/2000 | Bigge et al. |
| 6,835,727 B2 | 12/2004 | Okamoto et al. |
| 7,868,177 B2 | 1/2011 | Cee et al. |
| 9,963,444 B2 | 5/2018 | Malamas et al. |
| 2011/0112127 A1 | 5/2011 | Zhang |
| 2014/0094508 A1 | 5/2014 | Piomelli et al. |
| 2017/0114050 A1 | 4/2017 | Malamas et al. |
| 2018/0222894 A1 | 8/2018 | Malamas et al. |

FOREIGN PATENT DOCUMENTS

| | | |
|---|---|---|
| KR | 20130122361 A | 11/2013 |
| LV | 14955 B | 2/2015 |
| WO | 9637465 A1 | 11/1996 |
| WO | 2007130353 A1 | 11/2007 |
| WO | 2013090929 A1 | 6/2013 |
| WO | 2015055994 A1 | 4/2015 |
| WO | 2015/179190 A1 | 11/2015 |
| WO | 2016132134 A1 | 8/2016 |
| WO | 2015179190 A1 | 11/2016 |
| WO | 2017193063 A1 | 11/2017 |
| WO | 2019217977 A1 | 11/2019 |

OTHER PUBLICATIONS

Non-Final Office Action for U.S. Appl. No. 15/942,345, "N-Acylethanolamine Hydrolyzing Acid Amidase (NAAA) Inhibitors and Their Use Thereof", dated Apr. 15, 2019.
Non-Final Office Action for U.S. Appl. No. 15/311,817, "N-Acylethanolamine Hydrolyzing Acid Amidase (NAAA) Inhibitors and Their Use Thereof", dated Sep. 22, 2017.
Notice of Allowance for U.S. Appl. No. 15/311,817, "N-Acylethanolamine Hydrolyzing Acid Amidase (NAAA) Inhibitors and Their Use Thereof", dated Jan. 5, 2018.
Notification Concerning Transmittal of International Preliminary Report on Patentability for International Application No. PCT/US2015/030583, "N-Acylethanolamine Hydrolyzing Acid Amidase (NAAA) Inhibitors and Their Use Thereof", dated Nov. 22, 2016.
PCT/US2015/030583 Written Opinion of the International Searching Authority dated Jul. 29, 2015 entitled "N-Acylethanolamine Hydrolyzing Acid Amidase (NAAA) Inhibitors and Their Use Thereof."

(Continued)

*Primary Examiner* — Golam M Shameem
(74) *Attorney, Agent, or Firm* — Hamilton, Brook, Smith & Reynold, P.C.

(57) ABSTRACT

Disclosed herein are compounds represented by Structural Formula I:

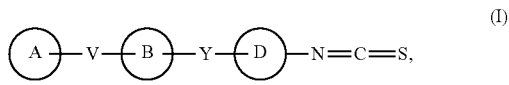

or a pharmaceutically acceptable salt thereof. Values for the variables in Structural Formula I are described herein. The compounds can be used to modulate (e.g., inhibit) N-acylethanolamine hydrolyzing acid amidase (NAAA) and thereby treat a variety of diseases, disorders and conditions mediated by NAAA, such as a gastrointestinal motility disorder, irritable bowel syndrome, an inflammatory bowel disorder, neuroinflammation, nicotine addiction, cancer, opioid dependence, analgesia, chemotherapy-induced neuropathic pain and pain. Also disclosed herein are compositions and methods including compounds of Structural Formula I, or a pharmaceutically acceptable salt thereof.

18 Claims, No Drawings

(56) References Cited

OTHER PUBLICATIONS

PCT/US2015/030583 International Search Report dated Jul. 29, 2015 entitled "N-Acylethanolamine Hydrolyzing Acid Amidase (NAAA) Inhibitors and Their Use Thereof."

Solorzano, C., et al., "Selective N-acylethanolomaine-hydrolyzing acid amidase inhibition reveals a key role for endogenous palmitoylethanolamide in inflammation", PNAS, 106(49): 20966-20971 (Dec. 8, 2009).

Supplemental Partial European Search Report for European Application No. 15 79 5556, "N-Acylethanolamine -Hydrolyzing Acid Amidase (NAAA) Inhibitors and Their Use Thereof", date of completion Oct. 12, 2017.

West, et al., "Mass Spectrometric Characterization of Human N-Acylethanolamine-Hydrolyzing Acid Amidase," J. Proteome Res., 11(2): 972-981 (2012).

West, J.M., et al., "Biochemical and Mass Spectrometric Characterization of Human N-Acylethanolamine-Hydrolyzing Acid Amidase Inhibition", PLOS One, 7(8): e43877 (Aug. 2012).

Whitten, K.M., "Synthesis and Biological Evaluation of Novel Endocannabinoid Probes, Metabolically Stable Analogs, and Nacylethanolamine-Hydrolyzing Acid Amidase Inhibitors," (2012) Chemistry Dissertations, Paper 56. [retrieved on Jul. 16, 2015] Retrieved from the Internet. <URL: http://hdl.handle.net/2047/d20002788>, pp. 2, 3, 7-18, 182-233.

Bisogno, T., et al., "Biosynthesis, Uptake and Degradation of Anandamide and Palmitoylethanolaide in Leukocytes", The Journal of Biological Chemistry, 272(6), Feb. 7, 1997, 3315-3323.

Calignano, A., et al., "Control of pain initiation by endogenous cannabinoids", Nature, 394, Jul. 16, 1998, 277-281.

Capasso, R., et al., "Inhibitory effect of palmitoylethanolamide on gastrointestinal motility in mice", British Journal of Pharmacology (2001) 134, 945-950.

Costa, B., et al., "Therapeutic effect of the endogenous fatty acid amide, palmitoylethanolamide, in rat acute inflammation: inhibition of nitric oxide and cyclo-oxygenase systems", British Journal of Pharmacology (2002) 137, 413-420.

Cuzzocrea, S., et al., "Role of endogenous and exogenous ligands for the peroxisome proliferators activated receptors alpha (PPAR-α) in the development of inflammatory bowel disease in mice", Laboratory Investigation (2004) 84, 1643-1654.

Darmani, N. A., et al., "Involvement of the cannabimimetic compounds, N-palmitoyl-ethanolamine, in inflammatory and neuropathic conditions: Review of the available pre-clinical data, and first human studies", Neuropharmacology 48 (2005) 1154-1163.

Final Office Action for U.S. Appl. No. 15/942,345, "N-Acylethanolamine Hydrolyzing Acid Amidase (NAAA) Inhibitors and Their Use Thereof", dated Aug. 29, 2019.

Fu, J., et al., "Oleylethanolamide regulates feeding and body weight through activation of the nuclear receptor PPAR-α", Nature, 425, Sep. 2003, 90-93.

Jaggar, S., et al., "The anti-hyperalgesic actions of the cannabinoid anandamide and the putative CB2 receptor agonist palmitoylethanolamide in visceral and somatic inflammatory pain", PAIN, 76 (1998) 189-199.

Kim, J-A., et al., "Expressin of Protease-Activated Receiptor 2 in Ulcerative Colitis", Inflammatory Bowel Diseases, 9 (4): 224-229, 2003.

Lambert D., et al., "Anticonvulsant Activity of N-Palmitoylethanolamide, a Putative Endocannabinoid, in Mice", Epilepsia, 42(3): 321-327 (2001).

Lo Verme, J., et al., "The search for the palmitoylethanolamide receptor", Life Sciences 77 (2005) 1685-1698.

Luchicchi, A., "Effects of fatty acid amide hydrolase inhibition on neuronal responses to nicotine, cocaine and morphine in the nucleus accumbens shell and ventral tegmental area: involvement of PPAR-α Nuclear Receptors", Addict Biol. Jul. 2010; 15(3): 277-288.

Mazzari, S., "N-(2-Hydroxyethyl)hexadecanamide is orally active in reducing edema formation and inflammatory hyperalgesia by down-modulating mast cell activation", European Journal of Pharmacology 300 (1996) 227-236.

Nissen, S.E., et al., "Effects of a Potent and Selective PPAR-α Agonist in Patients With Atherogenic Dyslipidemia or Hypercholesterolemia", JAM, Mar. 28, 2007-v297(12): 1362-1373.

Notification of Transmittal of the International Search Report and the Written Opinion of the International Searching Authority, or the Declaration for International Application No. PCT/US2019/040893, "N-Acylethanolamine Hydrolyzing Acid Amidase (NAAA) Inhibitors and Use Thereof", dated Sep. 10, 2019.

Okamoto, Y., et al., "Molecular Characterization of a Phospholipase D Generating Anandamide and Its Congeners", The Journal of Biological Chemistry, 279(7): 5298-5305 (Feb. 13, 2004).

Sheu, M., et al., "Topical Peroxisome Proliferator Activated Receptor-α Activators Reduce Inflammation in Irritant and Allergic Contact Mermatitis Models", Society for Investigatie Dermatology, 118(1): 94-101 (Jan. 2002).

Tsuboi, K., et al., The N-Acylethanolamine-Hydrolyzing Acid Amidase (NAAA), Chemistry and Biodiversity, vol. 4 (2007), 1914-1925.

Winterkamp, S., et al., "Urinary Excretion of N-Methylhistamine as a Marker of Disease Activity in Inflammatory Bowel Disease", The American Journal of Gastroenterology, 97(12): 3071-3077 (2002).

Notice of Allowance for U.S. Appl. No. 15/942,345, "N-Acylethanolamine Hydrolyzing Acid Amidase (NAAA) Inhibitors and Their Use Thereof", dated Dec. 11, 2019.

N-ACYLETHANOLAMINE HYDROLYZING ACID AMIDASE (NAAA) INHIBITORS AND USE THEREOF

RELATED APPLICATION

This application claims the benefit of U.S. Provisional Application No. 62/668,789, filed on May 8, 2018. The entire teachings of the above application are incorporated herein by reference.

GOVERNMENT SUPPORT

This invention was made with government support under Grant No. R01-DA003801 awarded by the National Institutes of Health. The government has certain rights in the invention.

BACKGROUND

N-Acylethanolamine hydrolyzing acid amidase (NAAA) is a lysosomal enzyme, which plays a central role in the deactivation of N-palmitoylethanolamine (PEA). PEA is an endogenous lipid produced on demand by most mammalian cells, and a growing body of evidence links PEA to the regulation of inflammatory and pain processes. PEA reduces peripheral inflammation and exerts neuroprotective and antinociceptive effects in rats and mice.

Accordingly, there is a need for pharmacologic strategies aimed at correcting a deficit in PEA/PPARα signaling by preventing PEA degradation, e.g., for the treatment of inflammatory disorders.

SUMMARY

This invention is based, in part, on the discovery that N-acylethanolamine hydrolyzing acid amidase (NAAA) inhibition exerts PPARα-dependent beneficial effects on colon inflammation and inflammatory bowel diseases, and also can play a critical role in other disorders associated with decreased PEA levels, including neuroinflammation, nicotine addiction, cancer, opioid dependence, analgesia, chemotherapy-induced neuropathic pain and pain.

Provided herein is a compound represented by the following structural formula:

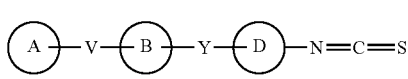

(I)

or a pharmaceutically acceptable salt thereof, wherein values for the variables (e.g., A, V, B, Y and D) are described herein.

Also provided herein is a composition comprising a compound (e.g., a compound of any one of Structural Formulas I-IIIa) or salt (e.g., a pharmaceutically acceptable salt of a compound of any one of Structural Formulas I-IIIa) described herein and a pharmaceutically acceptable carrier.

Also provided herein is a method for modulating (e.g., inhibiting) the activity of N-acylethanolamine hydrolyzing acid amidase, comprising contacting a receptor of N-acylethanolamine hydrolyzing acid amidase with a compound (e.g., a compound of any one of Structural Formulas I-IIIa), salt (e.g., a pharmaceutically acceptable salt of a compound of any one of Structural Formulas I-IIIa) or composition described herein.

Also provided herein is a method for treating a disease, disorder or condition mediated by NAAA in a subject in need thereof, comprising administering to the subject an effective amount of a compound (e.g., a compound of any one of Structural Formulas I-IIIa), salt (e.g., a pharmaceutically acceptable salt of a compound of any one of Structural Formulas I-IIIa) or composition described herein.

Also provided herein is a method of treating a disease, disorder or condition selected from an inflammatory gastrointestinal motility disorder, irritable bowel syndrome or an inflammatory bowel disorder in a subject in need thereof, comprising administering to the subject an effective amount of a compound, salt or composition described herein.

Also provided is a compound (e.g., a compound of any one of Structural Formulas I-IIIa), or a pharmaceutically acceptable salt thereof, or a composition for use in the treatment of a disease, disorder or condition described herein (e.g., a disease, disorder or condition mediated by NAAA; inflammatory gastrointestinal motility disorder; irritable bowel syndrome; inflammatory bowel disorder), wherein the compound, salt or composition is described herein. Also provided is use of a compound (e.g., a compound of any one of Structural Formulas I-IIIa), salt (e.g., a pharmaceutically acceptable salt of a compound of any one of Structural Formulas I-IIIa) or composition described herein for the manufacture of a medicament for the treatment of a disease, disorder or condition described herein (e.g., a disease, disorder or condition mediated by NAAA; inflammatory gastrointestinal motility disorder; irritable bowel syndrome; inflammatory bowel disorder).

NAAA inhibition offers the advantage of blocking PEA degradation under inflammatory stress and stimulating PPARα activation. A reduction in the reinforcing addictive nature of drugs of abuse has also been reported for inhibition of NAAA. These characteristics make NAAA an excellent therapeutic target for discovery of novel compounds to treat pain and inflammation without the addictive properties of opioids.

DETAILED DESCRIPTION

The following terms are used throughout as defined below.

As used herein, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element is essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to a non-hydrogen atom. Substituted groups also include groups in which one or more bonds to a hydrogen atom or carbon atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents.

"Optionally substituted" refers to an organic group that is substituted or unsubstituted. In some embodiments, an optionally substituted group is unsubstituted. In some embodiment, an optionally substituted group is substituted, for example, with one or more substituents described herein.

Examples of substituents include: halogen, hydroxyl, alkoxy, haloalkoxy (e.g., trifluoromethoxy), alkenoxy, alkynoxy, aryloxy, aralkyloxy, heteroaryloxy, heteroarylalkoxy, heterocyclylalkyl, cycloalkyl, cylcolalkylalkyl, heterocyclyl, cycloalkoxy, heterocyclyloxy, cycloalkylalkoxy, heterocyclylalkoxy, oxo, carboxy, ester, urethane, oxime, hydroxylamine, alkoxyamine, aralkoxyamine, thiol, sulfide, sulfoxide, sulfone, sulfonyl, pentafluorosulfanyl (i.e., —$SF_5$), sulfonamide, amino, N-oxide, hydrazine, hydrazide, azide, amide, urea, amidine, guanidine, enamine, imide, isocyanate, isothiocyanate, cyanate, thiocyanate, imine, nitro, nitrile (i.e., CN), and the like. In some embodiments, a substituted group is substituted with one or more substituents independently selected from halogen, hydroxyl, alkoxy, haloalkoxy, isocyanate or nitrile. In some embodiments, a substituted group is substituted with one or more substituents independently selected from halogen, alkoxy or haloalkoxy.

Substituted ring groups such as substituted cycloalkyl, aryl, heterocyclyl, heteroaryl, cycloalkylene, arylene, heterocyclylene and heteroarylene groups also include rings and ring systems that may also be substituted with substituted or unsubstituted alkyl, alkenyl, and alkynyl groups as defined below (e.g., alkyl). In some embodiments, a substituted ring group is substituted with one or more substituents independently selected from halogen, hydroxyl, alkoxy, haloalkoxy, isocyanate, nitrile, alkyl or haloalkyl (e.g., trifluoromethyl). In some embodiments, a substituted ring group is substituted with one or more substituents independently selected from halogen, alkoxy, haloalkoxy or haloalkyl.

"Alkyl" refers to an optionally substituted, saturated, aliphatic, branched or straight-chain, monovalent, hydrocarbon radical having from 1 to 12 carbon atoms and, typically, from 1 to 10 carbon atoms or, in some embodiments, from 1 to 8, 1 to 6, 1 to 5 or 1 to 4 carbon atoms. Thus, "$(C_1-C_4)$alkyl" means a radical having from 1-4 carbon atoms in a linear or branched arrangement. Examples of straight chain alkyl groups include, but are not limited to, methyl, ethyl, n-propyl, n-butyl, n-pentyl, n-hexyl, n-heptyl, and n-octyl. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted one or more times (e.g., 1, 2, 3, 4, 5, etc.) independently with substituents such as those listed above.

"Alkylene" refers to an optionally substituted, saturated, aliphatic, branched or straight-chain, divalent, hydrocarbon radical having from 1 to 12 carbon atoms and, typically, from 1 to 10 carbon atoms or, in some embodiments, from 1 to 8, 1 to 6, 1 to 5 or 1 to 4 carbon atoms. Thus, "$(C_1-C_4)$alkylene" means a diradical having from 1-4 carbon atoms in a linear or branched arrangement. Examples of alkylene include, but are not limited to, methylene, ethylene (e.g., 1,2-ethylene, 1,1-ethylene), propylene, butylene, pentylene, and the like. Alkylene groups may be substituted one or more times (e.g., 1, 2, 3, 4, 5, etc.) independently with substituents such as those listed above.

"Alkenyl" refers to an optionally substituted, aliphatic, branched or straight-chain, monovalent, hydrocarbon radical having at least one carbon-carbon double bond and from 2 to 12 carbon atoms, and, typically, from 2 to 10 carbon atoms or, in some embodiments, from 2 to 8, 2 to 6, 2 to 5 or 2 to 4 carbon atoms. Thus, "$(C_2-C_6)$alkenyl" means a radical having at least one carbon-carbon double bond and from 2 to 6 carbon atoms in a linear or branched arrangement. In some embodiments, the alkenyl group has one, two, or three carbon-carbon double bonds. Examples include, but are not limited to, vinyl, allyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, among others. Alkenyl groups may be mono-substituted or substituted more than once, such as, but not limited to, mono-, di- or tri-substituted with substituents such as those listed above.

"Alkenylene" refers to an optionally substituted, aliphatic, branched or straight-chain, divalent, hydrocarbon radical having at least one carbon-carbon double bond and from 2 to 12 carbon atoms and, typically, from 2 to 10 carbon atoms or, in some embodiments, from 2 to 8, 2 to 6, 2 to 5 or 2 to 4 carbon atoms. Thus, "$(C_2-C_6)$alkenylene" means a diradical having at least one carbon-carbon double bond and from 2 to 6 carbon atoms in a linear or branched arrangement. In some embodiments, the alkenylene group has one, two, or three carbon-carbon double bonds. Alkenylene includes, but is not limited to, ethenylene and isoprenylene. Alkenylene groups may be mono-substituted or substituted more than once, such as, but not limited to, mono-, di- or tri-substituted with substituents such as those listed above.

"Alkynyl" refers to an optionally substituted, aliphatic, branched or straight-chain, monovalent, hydrocarbon radical having at least one carbon-carbon triple bond and from 2 to 12 carbon atoms and, typically, from 2 to 10 carbon atoms or, in some embodiments, from 2 to 8, 2 to 6, 2 to 5 or 2 to 4 carbon atoms. Thus, "$(C_2-C_6)$alkynyl" means a radical having at least one carbon-carbon triple bond and from 2 to 6 carbon atoms in a linear or branched arrangement. In some embodiments, the alkynyl group has one, two, or three carbon-carbon triple bonds. Examples include, but are not limited to, —C≡CH, —C≡$CCH_3$, —$CH_2$C≡$CCH_3$, —C≡$CCH_2$CH($CH_2CH_3$)$_2$, among others. Alkynyl groups may be mono-substituted or substituted more than once, such as, but not limited to, mono-, di- or tri-substituted with substituents such as those listed above.

"Alkynylene" refers to an optionally substituted, aliphatic, branched or straight-chain, divalent, hydrocarbon radical having at least one carbon-carbon triple bond and from 2 to 12 carbon atoms and, typically, from 2 to 10 carbon atoms or, in some embodiments, from 2 to 8, 2 to 6, 2 to 5 or 2 to 4 carbon atoms. Thus, "$(C_2-C_6)$alkynylene" means a diradical having at least one carbon-carbon triple bond and from 2 to 6 carbon atoms in a linear or branched arrangement. In some embodiments, the alkynylene group has one, two, or three carbon-carbon triple bonds. Alkynylene includes, but is not limited to, propargylene. Alkynylene groups may be mono-substituted or substituted more than once, such as, but not limited to, mono-, di- or tri-substituted with substituents such as those listed above.

"Cycloalkyl" refers to an optionally substituted, saturated, aliphatic, monovalent, monocyclic, bicyclic or tricyclic, hydrocarbon ring radical having from 3 to 12 carbon atoms in the ring(s), or, in some embodiments, 3 to 10, 3 to 8, 3 to 7, 3 to 4, 5, or 6 carbon atoms. Thus, "$(C_3-C_7)$cycloalkyl" means a ring radical having from 3 to 7 ring carbons. Exemplary monocyclic cycloalkyl groups include, but are not limited to, cyclopropyl, cyclobutyl, cyclopentyl, cyclohexyl, cycloheptyl, and cyclooctyl. Bi- and tricyclic ring systems include both bridged cycloalkyl groups and fused rings, such as, but not limited to, bicyclo[1.1.1]pentyl, bicyclo[2.1.1]hexyl, adamantyl, decalinyl, and the like. Cycloalkyl groups may be substituted one or more times as defined above. Cycloalkyl groups may also include rings that are substituted with alkyl as defined above. Representative substituted cycloalkyl groups may be mono-substituted or substituted more than once, such as, but not limited to, 3-substituted cyclohexyl; 2,2-, 2,3-, 2,4-2,5- or 2,6-disubstituted cyclohexyl; 3-substituted cyclobutyl; or 3-substituted bicyclo[1.1.1]pentyl, all of which may be substituted with substituents such as those listed above. In one embodiment, cycloalkyl is $(C_3-C_7)$cycloalkyl (e.g., cyclobutyl).

"Cycloalkylene" refers to an optionally substituted, saturated, aliphatic, divalent, monocyclic, bicyclic or tricyclic, hydrocarbon ring radical having from 3 to 12 carbon atoms in the ring(s), or, in some embodiments, 3 to 10, 3 to 8, 3 to 7, 3 to 4, 5, or 6 carbon atoms. Thus, "$(C_3-C_7)$cycloalkylene" means a ring diradical having from 3 to 7 ring carbons. Exemplary monocyclic cycloalkylene groups include, but are not limited to, cyclopropylene, cyclobutylene, cyclopentylene, cyclohexylene, cycloheptylene, and cyclooctylene. Bi- and tricyclic ring systems include both bridged cycloalkyl groups and fused rings, such as, but not limited to, bicyclo[1.1.1]pentylene, bicyclo[2.1.1]hexylene, adamantylene, decalinylene, and the like. Cycloalkylene groups may be substituted one or more times with groups as defined above. Cycloalkylene groups may also include rings that are substituted with alkyl as defined above. Representative substituted cycloalkylene groups may be mono-substituted or substituted more than once, such as, but not limited to, 3-substituted cyclohexylene; 2,2-, 2,3-, 2,4-2,5- or 2,6-disubstituted cyclohexylene; 3-substituted cyclobutylene; or 3-substituted bicyclo[1.1.1]pentylene, all of which may be substituted with substituents such as those listed above. In one embodiment, cycloalkylene is $(C_3-C_7)$cycloalkylene.

"Cycloalkylalkyl" refers to an alkyl group as defined above in which a hydrogen or carbon bond of the alkyl group is replaced with a bond to a cycloalkyl group as defined herein. Substituted cycloalkylalkyl groups may be substituted at the alkyl, the cycloalkyl or both the alkyl and cycloalkyl portions of the group. Cycloalkylalkyl groups may be substituted one or more times with substituents such as those listed above.

"Aryl" refers to an optionally substituted, monocyclic, bicyclic or tricyclic, carbocyclic, monovalent aromatic ring radical having from 6 to 15 ring carbon atoms. Thus, "$(C_6-C_{15})$aryl" means a ring radical having from 6-15 carbon atoms. Aryl groups include, but are not limited to, phenyl, azulenyl, heptalenyl, biphenyl, fluorenyl, phenanthrenyl, anthracenyl, indenyl, indanyl, pentalenyl, and naphthyl. In some embodiments, aryl has from 6 to 14 ring carbons, from 6 to 12, from 6 to 10 or 6 ring carbons. In some embodiments, aryl is phenyl or naphthyl (e.g., phenyl). The phrase "aryl groups" includes groups containing fused rings, such as fused aromatic-aliphatic ring systems (e.g., indanyl, tetrahydronaphthyl, and the like). Aryl groups may be mono-substituted or substituted more than once (e.g., disubstituted). Monosubstituted aryl groups include, but are not limited to, 2-, 3-, 4-, 5-, or 6-substituted phenyl or naphthyl groups, which may be substituted with substituents such as those listed above. Disubstituted aryl groups include, but are not limited to, 3,4-disubstituted phenyl.

"Arylene" refers to an optionally substituted, monocyclic, bicyclic or tricyclic, carbocyclic, divalent aromatic ring radical having from 6 to 15 ring carbon atoms. Thus, "$(C_6-C_{15})$arylene" means a ring radical having from 6 to 15 carbon atoms. Arylene groups include, but are not limited to, phenylene and naphthylene. In some embodiments, arylene has from 6 to 14 ring carbons, from 6 to 12, from 6 to 10 or 6 ring carbons. In some embodiments, arylene is phenylene or naphthylene (e.g., phenylene). The phrase "arylene" includes groups containing fused rings, such as fused aromatic-aliphatic ring systems (e.g., indanylene, tetrahydronaphthylene, and the like). Arylene groups may be mono-substituted or substituted more than once (e.g., disubstituted). Monosubstituted arylene groups include, but are not limited to, 2-, 3-, 4-, 5-, or 6-substituted phenylene or naphthylene groups, which may be substituted with substituents such as those listed above. Disubstituted arylene groups include, but are not limited to, 3,4-disubstituted phenylene.

"Aralkyl" refers to an alkyl group as defined above in which a hydrogen atom of the alkyl group is replaced with an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Aralkyl groups may be substituted one or more times with substituents such as those listed above.

"Heterocyclyl" refers to an optionally substituted, saturated or unsaturated, aliphatic, monocyclic, bicyclic or tricyclic, monovalent, hydrocarbon ring system having from 3 to 16 ring atoms, wherein at least one carbon atom in the ring system has been replaced with a heteroatom, such as, but not limited to, N, S or O. Thus, "$(C_3-C_7)$heterocyclyl" means a heterocyclic ring system having from 3 to 7 ring atoms. In some embodiments, the heterocyclyl group contains 1, 2, 3 or 4 heteroatoms. In some embodiments, heterocyclyl has from 3 to 6, from 3 to 7, from 3 to 10, from 3 to 12, or from 3 to 14 ring members. "Heterocyclyl" includes fused ring species including those comprising fused aromatic and non-aromatic groups, such as, for example, 2,3-dihydrobenzo[1,4]dioxinyl, and benzo[1,3]dioxolyl. The phrase also includes bridged polycyclic ring systems containing a heteroatom such as, but not limited to, quinuclidyl. Heterocyclyl groups include, but are not limited to, azetidinyl, pyrrolidinyl, piperidinyl, piperazinyl, azepanyl, tetrahydrofuranyl, tetrahydropyranyl, morpholinyl, thiomorpholinyl, and dioxidyl. Heterocyclyl groups may be mono-substituted or substituted more than once, such as, disubstituted with various substituents such as those listed above.

"Heterocyclylene" refers to an optionally substituted, saturated or unsaturated, aliphatic, monocyclic, bicyclic or tricyclic, divalent, hydrocarbon ring system having from 3 to 16 ring atoms, wherein at least one carbon atom in the ring system has been replaced with a heteroatom, such as, but not limited to, N, S or O. Thus, "$(C_3-C_7)$heterocyclylene" means a heterocyclic ring system having from 3 to 7 ring atoms. In some embodiments, the heterocyclylene group contains 1, 2, 3 or 4 heteroatoms. In some embodiments, heterocyclylene has from 3 to 6, from 3 to 7, from 3 to 10, from 3 to 12, or from 3 to 14 ring members. "Heterocyclylene" includes fused ring species including those comprising fused aromatic and non-aromatic groups, such as, for example, 2,3-dihydrobenzo[1,4]dioxinylene, and benzo[1,3]dioxolylene. The phrase also includes bridged polycyclic ring systems containing a heteroatom such as, but not limited to, quinuclidyl. Heterocyclylene groups include, but are not limited to, azetidinylene, pyrrolidinylene, piperidinylene, piperazinylene, azepanylene, tetrahydrofuranylene, tetrahydropyranylene, morpholinylene, thiomorpholinylene, and dioxidylenyl. Heterocyclylene groups may be mono-substituted or substituted more than once, such as, disubstituted with various substituents such as those listed above.

"Heteroaryl" refers to an optionally substituted, monocyclic, bicyclic or tricyclic, monovalent, aromatic, hydrocarbon ring system having from 5 to 15 ring carbons, wherein at least one carbon atom in the ring system has been replaced with a heteroatom, such as, but not limited to, N, S and O. Thus, "$(C_5-C_{15})$heteroaryl" means a heterocyclic aromatic ring system having from 5 to 15 ring atoms consisting of carbon and at least one heteroatom. Heteroaryl groups include, but are not limited to, pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl. Heteroaryl groups include fused ring compounds in which all rings are aromatic such as indolyl groups, and include fused ring compounds in which only one of the rings is aromatic, such as 2,3-dihydroindolyl. Heteroaryl groups may be substituted one or more times with various substituents such as those listed above.

"Heteroarylene" refers to an optionally substituted, monocyclic, bicyclic or tricyclic, divalent, aromatic, hydrocarbon ring system having from 5 to 15 ring carbons, wherein at least one carbon atom in the ring system has been replaced with a heteroatom, such as, but not limited to, N, S and O. Thus, "$(C_5-C_{15})$heteroarylene" means a heterocyclic aromatic ring system having from 5 to 15 ring atoms consisting of carbon and at least one heteroatom. Heteroarylene groups include, but are not limited to, pyrrolylene, pyrazolylene, triazolylene, tetrazolylene, oxazolylene, isoxazolylene, thiazolylene, pyridinylene, pyridazinylene, pyrimidinylene, pyrazinylene, thiophenylene, benzothiophenylene, furanylene, benzofuranylene, indolylene, azaindolylene (pyrrolopyridinylene), indazolylene, benzimidazolylene, imidazopyridinylene (azabenzimidazolylene), pyrazolopyridinylene, triazolopyridinylene, benzotriazolylene, benzoxazolylene, benzothiazolylene, benzothiadiazolylene, imidazopyridinylene, isoxazolopyridinylene, thianaphthylene, purinylene, xanthinylene, adeninylene, guaninylene, quinolinylene, isoquinolinylene, tetrahydroquinolinylene, quinoxalinylene, and quinazolinylene. Heteroarylene groups include fused ring compounds in which all rings are aromatic such as indolylene groups, and include fused ring compounds in which only one of the rings is aromatic, such as 2,3-dihydroindolylene. Heteroarylene groups may be substituted one or more times with various substituents such as those listed above.

"Heterocyclylalkyl" refers to an alkyl group as defined above in which a hydrogen or carbon bond of the alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Heterocyclylalkyl groups may be substituted one or more times with substituents such as those listed above.

"Heteroaralkyl" refers to an alkyl group as defined above in which a hydrogen or carbon bond of the alkyl group is replaced with a bond to a heteroaryl group as defined above. Substituted heteroaralkyl groups may be substituted at the alkyl, the heteroaryl or both the alkyl and heteroaryl portions of the group. Heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of an alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Alkoxy groups may be substituted one or more times with substituents such as those listed above.

The terms "alkanoyl" and "alkanoyloxy," as used herein, refer, respectively, to —C(O)-alkyl groups and —O—C(O)-alkyl groups, each containing 2-5 carbon atoms.

The terms "aryloxy" and "arylalkoxy," as used herein, refer, respectively, to a substituted or unsubstituted aryl group bonded to an oxygen atom and a substituted or unsubstituted aralkyl group bonded to an oxygen atom at the alkyl. Examples include but are not limited to phenoxy, naphthyloxy, and benzyloxy. Aryloxy and arylalkoxy groups may be substituted one or more times with substituents such as those listed above.

The term "carboxylate" as used herein refers to a —COOH group. A "substituted carboxylate" refers to —C(O)O-G where G is a carboxylate protecting group. Carboxylate protecting groups are well known to one of ordinary skill in the art. An extensive list of protecting groups for the carboxylate group functionality and procedures for adding or removing the protecting groups may be found in Protective Groups in Organic Synthesis, Greene, T. W.; Wuts, P. G. M., John Wiley & Sons, New York, N.Y., (3rd Edition, 1999), which is hereby incorporated by reference in its entirety and for any and all purposes as if fully set forth herein.

The term "ester" as used herein refers to —COOR$^{70}$ groups. R$^{70}$ is an alkyl, cycloalkyl, alkenyl, alkynyl, aryl, aralkyl, cylcoalkylalkyl, heterocyclylalkyl, heterocyclyl, heteroaryl or heteroarylalkyl group as defined herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or an alkyl, cycloalkyl, alkenyl, alkynyl, aryl, aralkyl, cylcoalkylalkyl, heterocyclylalkyl, heterocyclyl, heteroaryl or heteroarylalkyl group as defined herein. Amido groups include, but are not limited to, carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and, in others, the amide is —NHC(O)-alkyl, and the group is termed "alkanoylamino."

The term "nitrile" or "cyano" as used herein refers to the —CN group.

The term "amine" (or "amino") as used herein refers to —NR$^{75}$R$^{76}$ groups, wherein R$^{75}$ and R$^{76}$ are independently hydrogen, or an alkyl, cycloalkyl, alkenyl, alkynyl, aryl, aralkyl, cylcoalkylalkyl, heterocyclylalkyl, heterocyclyl, heteroaryl or heteroarylalkyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "halogen" or "halo," as used herein, refers to bromine, chlorine, fluorine, or iodine. In some embodiments, the halogen is fluorine. In other embodiments, the halogen is chlorine or bromine.

The term "hydroxy," as used herein, can refer to —OH or its ionized form, —O—.

The term "isocyano," as used herein, refers to —NC.

The term "isothiocyano," as used herein, refers to —NCS.

Pharmaceutically acceptable salts of compounds described herein are within the scope of the present technology and include acid or base addition salts which retain the desired pharmacological activity and are not biologically undesirable (e.g., the salt is not unduly toxic, allergenic, or irritating, and is bioavailable).

When the compound of the present technology has a basic group, such as, for example, an amino group, pharmaceutically acceptable salts may be formed with inorganic acids (such as hydrochloric acid, hydroboric acid, nitric acid, sulfuric acid, and phosphoric acid), organic acids (such as alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid).

When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts may be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

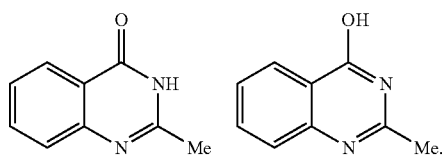

As another example, guanidines may exhibit the following isomeric forms in protic organic solution, also referred to as tautomers of each other:

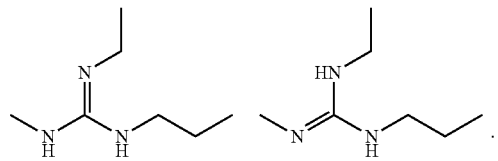

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers may be isolated or synthesized so as to be substantially free of their enantiomeric or diastereomeric partners, and these stereoisomers are all within the scope of the present technology.

Some stereoisomers may be more active or may exhibit beneficial effects when enriched relative to the other stereoisomer(s) or when separated from the other stereoisomer(s). Accordingly, the compounds of the disclosure may be present as a mixture of stereoisomers, individual stereoisomers, or as an optically active or enantiomerically pure form.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

It will be understood that certain polyvalent (e.g., divalent) radicals, such as certain of the divalent radicals listed as potential values for variables V and Y in Structural Formula I (e.g., —C(O)N($R^{10}$)—, —C(O)N($R^{13}$)—, —C(O)O—, —S($O_2$)N($R^{13}$)—, —S($O_2$)O—, —P(O)($R^{14}$)N($R^{13}$)—, —P(O)($R^{14}$)O—, —OC(O)N($R^{13}$)—), can be attached to the remainder of Structural Formula I in various orientations. For example, when V is —C(O)N($R^{10}$)— in Structural Formula I, V can be oriented so that the carbonyl carbon of —C(O)N($R^{10}$)— is attached to A, and the nitrogen atom of —C(O)N($R^{10}$)— is attached to B. Alternatively, V can be oriented so that the nitrogen atom of —C(O)N($R^{10}$)— is attached to A, and the carbonyl carbon of —C(O)N($R^{10}$)— is attached to B. Unless indicated otherwise, every possible orientation of such radicals is intended to be included within the scope of the invention.

In some embodiments, the orientation of the value is fixed, such that the orientation of the value in the text from left to right matches its orientation in the molecule, also read from left to right. Such a fixed orientation value can be indicated with an asterisk. Thus, a value for V of *—C(O)N($R^{10}$)— would indicate that V is oriented so that the carbonyl carbon of —C(O)N($R^{10}$)— is attached to A, and the nitrogen atom of —C(O)N($R^{10}$)— is attached to B.

A description of example embodiments follows.
Compounds

A first embodiment is a compound represented by the following structural formula:

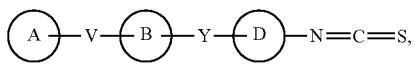

(I)

or a pharmaceutically acceptable salt thereof, wherein:
Ring A is absent, cycloalkyl, aryl, heterocyclyl or heteroaryl;
V is absent, —O—, —N($R^{10}$)—, —S(O)$_2$—, —S(O)—, —C(O)—, —C(O)N($R^{10}$)— or —C($R^{11}$)($R^{12}$)— (e.g., absent, —O—, —N($R^{10}$)—, —S(O)$_2$—, —S(O)—, —C(O)—, *—C(O)N($R^{10}$)— or —C($R^{11}$)($R^{12}$)—);
$R^{10}$ is —H or $C_1$-$C_4$ alkyl;
$R^{11}$ and $R^{12}$ are each independently —H, $C_1$-$C_4$ alkyl, cycloalkyl, aryl, heterocyclyl or heteroaryl, or taken together with the carbon atom to which they are attached, form a saturated or unsaturated ring (e.g., containing from 3 to 16 ring atoms selected from carbon, nitrogen, oxygen or sulfur);
B is $C_1$-$C_6$ alkylene, $C_1$-$C_6$ alkenylene, $C_1$-$C_6$ alkynylene, cycloalkylene, arylene, heterocyclylene or heteroarylene;
Y is —C(O)N($R^{13}$)—, —C(O)O—, —S($O_2$)N($R^{13}$)—, —S($O_2$)O—, —P(O)($R^{14}$)N($R^{13}$)—, —P(O)($R^{14}$)O—, —OC(O)N($R^{13}$)—, —OC(O)O— or —N($R^{13}$)C(O)N($R^{13}$)— (e.g., *—C(O)N($R^{13}$)—, *—C(O)O—, *—S($O_2$)N($R^{13}$)—, *—S($O_2$)O—, *P(O)($R^{14}$)N($R^{13}$)—,
*—P(O)($R^{14}$)O—, *—OC(O)N($R^{13}$)—, —OC(O)O— or —N($R^{13}$)C(O)N($R^{13}$)—); each $R^{13}$ is independently —H or $C_1$-$C_4$ alkyl;
$R^{14}$ is $C_1$-$C_4$ alkyl; and
Ring D is $C_3$-$C_7$ cycloalkyl (e.g., cyclobutyl, bicyclo[1.1.1]pentanyl).

In a first aspect of the first embodiment, Ring A is aryl or heteroaryl. Values for the remaining variables are as described in the first embodiment.

In a second aspect of the first embodiment, Ring A is phenyl (e.g., p-methoxyphenyl, m-methoxyphenyl, 3-fluoro-4-methoxyphenyl) or pyridinyl (e.g., pyridin-2-yl, pyridin-3-yl). Values for the remaining variables are as described in the first embodiment, or first aspect thereof.

In a third aspect of the first embodiment, V is absent, —O— or —N($R^{10}$)—. Values for the remaining variables are as described in the first embodiment, or first or second aspect thereof.

In a fourth aspect of the first embodiment, V is absent. Values for the remaining variables are as described in the first embodiment, or first through third aspects thereof.

In a fifth aspect of the first embodiment, B is arylene or heteroarylene. Values for the remaining variables are as described in the first embodiment, or first through fourth aspects thereof.

In a sixth aspect of the first embodiment, B is phenylene (e.g., 2-fluorophenyl-1,4-enyl, phenyl-1,4-enyl) or pyridinylene (e.g., pyridinyl-2,5-enyl, pyridinyl-3,5-enyl). Values for the remaining variables are as described in the first embodiment, or first through third aspects thereof.

In a seventh aspect of the first embodiment, Y is —C(O)N($R^{13}$)—, —C(O)O—, —S($O_2$)N($R^{13}$)—, —S($O_2$)O—, —P(O)($R^{14}$)N($R^{13}$)— or —OC(O)N($R^{13}$)— (e.g., *—C(O)N($R^{13}$)—, *—C(O)O—, *—S($O_2$)N($R^{13}$)—, *—S($O_2$)O—, *—P(O)($R^{14}$)N($R^{13}$)— or *—OC(O)N($R^{13}$)—). Values for the remaining variables are as described in the first embodiment, or first through sixth aspects thereof.

In an eighth aspect of the first embodiment, Y is —C(O)N($R^{13}$)—, —S($O_2$)N($R^{13}$)— or —P(O)($R^{14}$)N($R^{13}$)— (e.g., *—C(O)N($R^{13}$)—, *—S($O_2$)N($R^{13}$)— or *—P(O)($R^{14}$)N($R^{13}$)—). Values for the remaining variables are as described in the first embodiment, or first through seventh aspects thereof.

In a ninth aspect of the first embodiment, $R^{10}$ is —H. Values for the remaining variables are as described in the first embodiment, or first through eighth aspects thereof.

In a tenth aspect of the first embodiment, $R^{11}$ and $R^{12}$ are each —H. Values for the remaining variables are as described in the first embodiment, or first through ninth aspects thereof.

In an eleventh aspect of the first embodiment, $R^{13}$ is —H. Values for the remaining variables are as described in the first embodiment, or first through tenth aspects thereof.

In a twelfth aspect of the first embodiment, $R^{14}$ is —$CH_3$. Values for the remaining variables are as described in the first embodiment, or first through eleventh aspects thereof.

In a thirteenth aspect of the first embodiment, Y is —C(O)N($R^{13}$)— or —S($O_2$)N($R^{13}$)— (e.g., *—C(O)N($R^{13}$)— or *—S($O_2$)N($R^{13}$)—). Values for the remaining variables are as described in the first embodiment, or first through twelfth aspects thereof.

A second embodiment is a compound represented by the following structural formula:

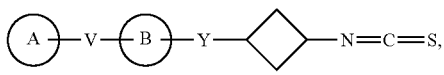

(II)

or a pharmaceutically acceptable salt thereof. Values for the variables are as described in the first embodiment, or any aspect thereof.

In a first aspect of the second embodiment, the compound is represented by the following structural formula:

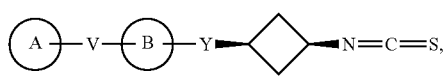

(IIa)

or a pharmaceutically acceptable salt thereof. Values for the variables are as described in the first embodiment, or any aspect thereof.

A third embodiment is a compound represented by the following structural formula:

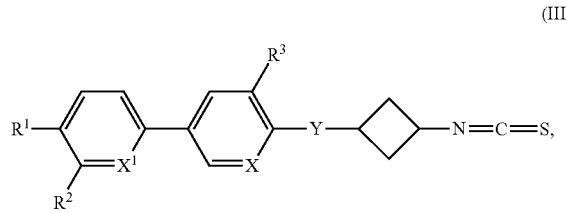

(III)

or a pharmaceutically acceptable salt thereof, wherein:
X and $X^1$ are each independently —C($R^{15}$)— or —N—;
$R^{15}$ is —H or halo (e.g., fluoro);
$R^1$ is $C_1$-$C_4$ alkoxy (e.g., —OCH$_3$);
$R^2$ is —H or halo (e.g., fluoro); and
$R^3$ is —H or halo (e.g., fluoro).
Values for the remaining variables are as described in the first embodiment, or any aspect thereof.

In a first aspect of the third embodiment, the compound is represented by the following structural formula:

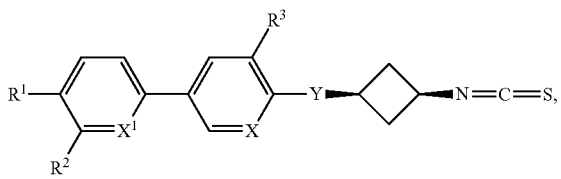

(IIIa)

or a pharmaceutically acceptable salt thereof. Values for the variables are as described in the first embodiment, or any aspect thereof, or the third embodiment.

In a second aspect of the third embodiment, X is —C(H)— and $X^1$ is —C(H)—. Values for the remaining variables are as described in the first embodiment, or any aspect thereof, or the third embodiment, or first aspect thereof.

In a third aspect of the third embodiment, X is —N— and $X^1$ is —N—. Values for the remaining variables are as described in the first embodiment, or any aspect thereof, or the third embodiment, or first or second aspect thereof.

In a fourth aspect of the third embodiment, X is —N— and $X^1$ is —C(H)—. Values for the remaining variables are as described in the first embodiment, or any aspect thereof, or the third embodiment, or first through third aspects thereof.

In a fifth aspect of the third embodiment, X is —C(H)— and $X^1$ is —N—. Values for the remaining variables are as described in the first embodiment, or any aspect thereof, or the third embodiment, or first through fourth aspects thereof.

In a sixth aspect of the third embodiment, $R^1$ is —OCH$_3$. Values for the remaining variables are as described in the first embodiment, or any aspect thereof, or the third embodiment, or first through fifth aspects thereof.

In a seventh aspect of the third embodiment, $R^{15}$ is —H. Values for the remaining variables are as described in the first embodiment, or any aspect thereof, or the third embodiment, or first through sixth aspects thereof.

In one embodiment, the compound is a compound set forth in Table 1, or a pharmaceutically acceptable salt thereof.

TABLE 1

| Compound Structure |
| --- |
| 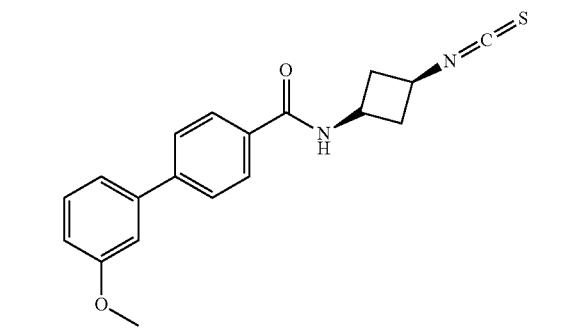 |
| 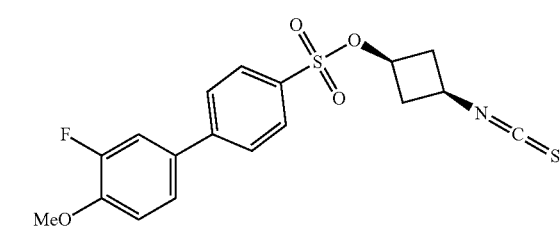 |
| 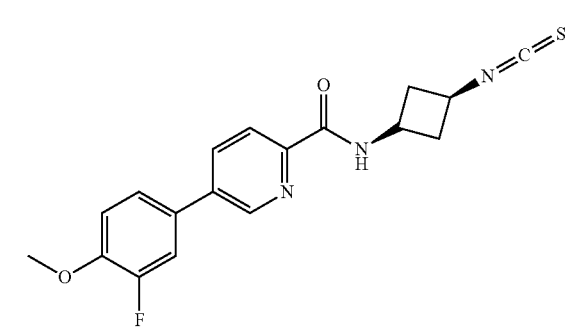 |

TABLE 1-continued
Compound Structure
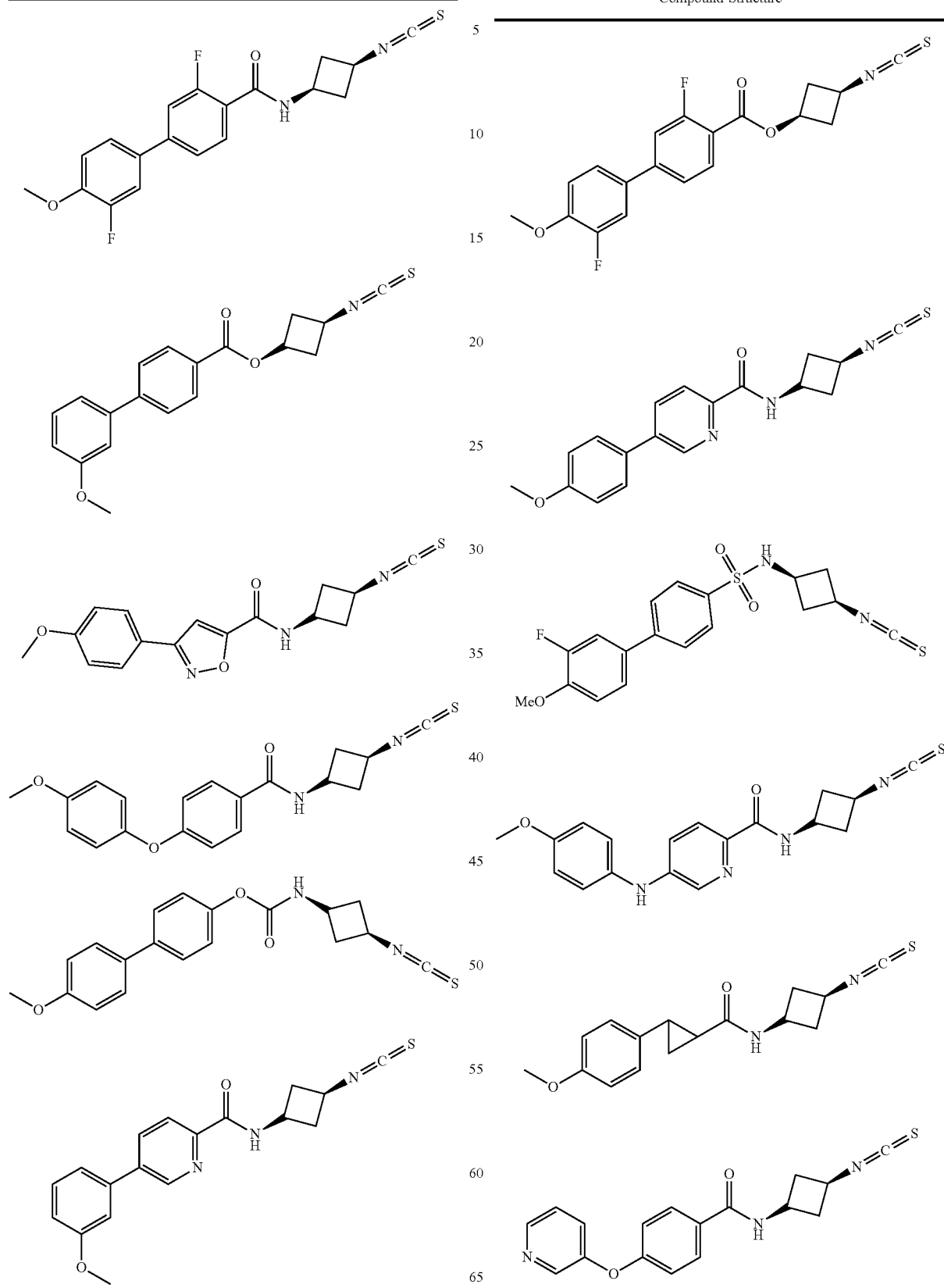

TABLE 1-continued
Compound Structure
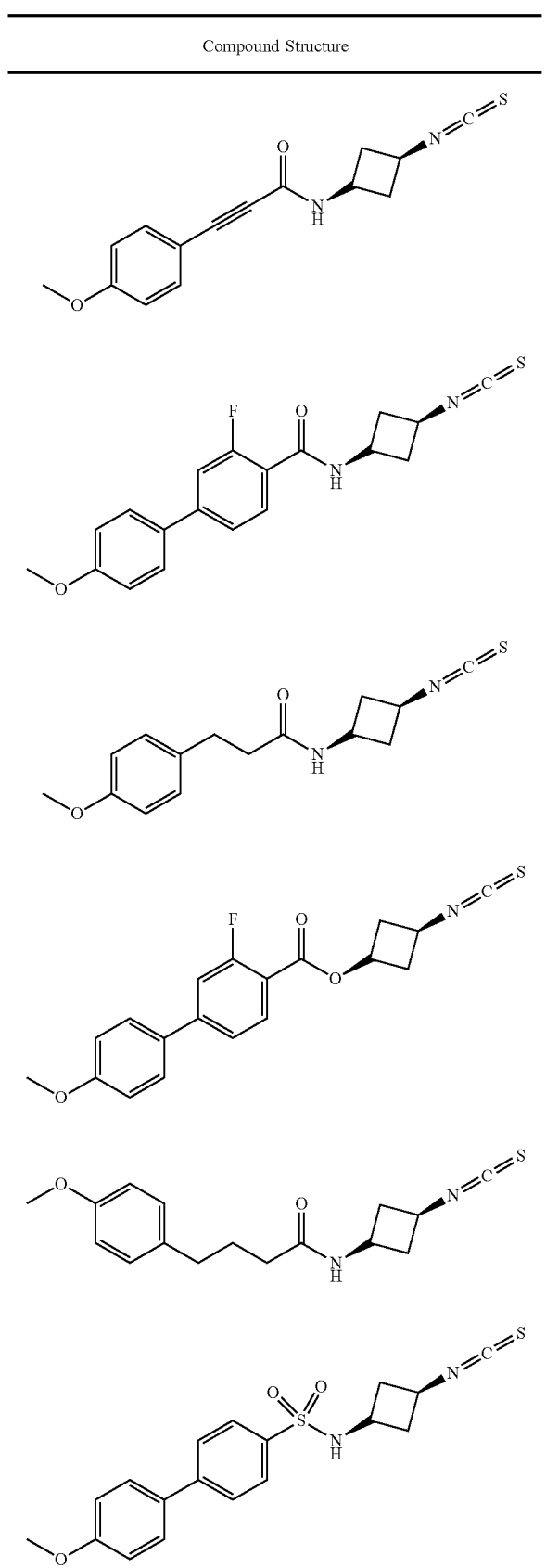
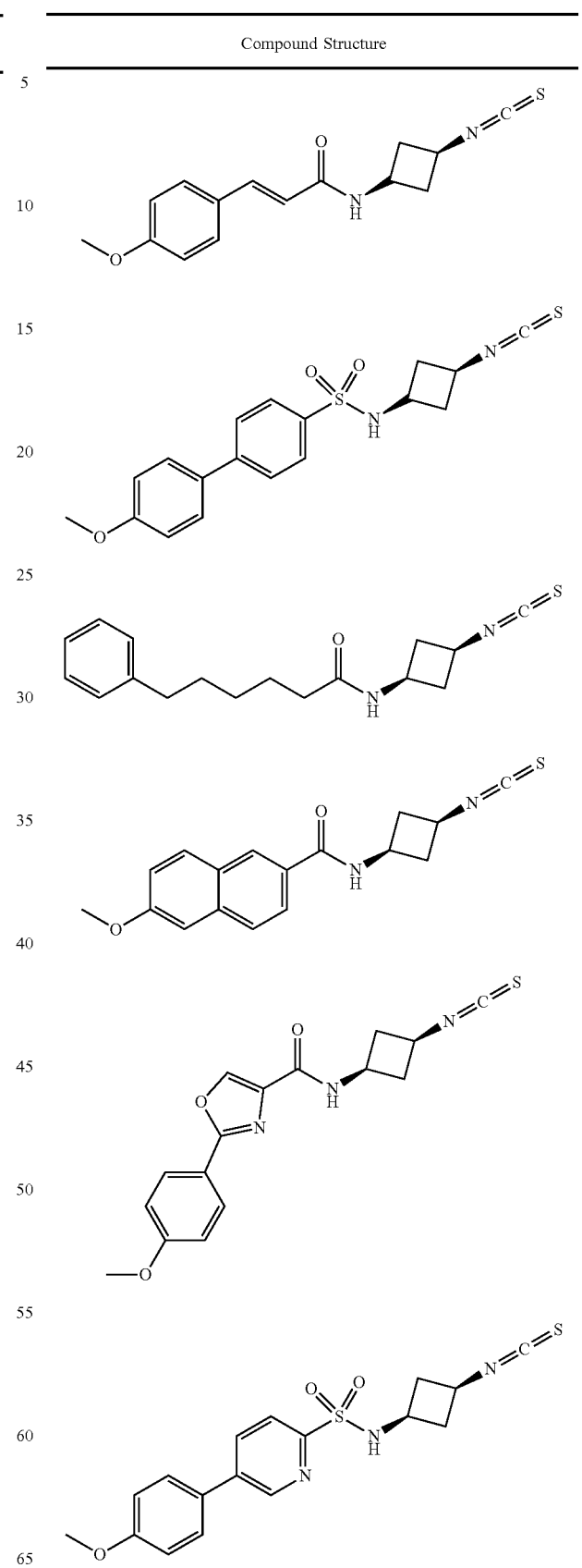

TABLE 1-continued
Compound Structure
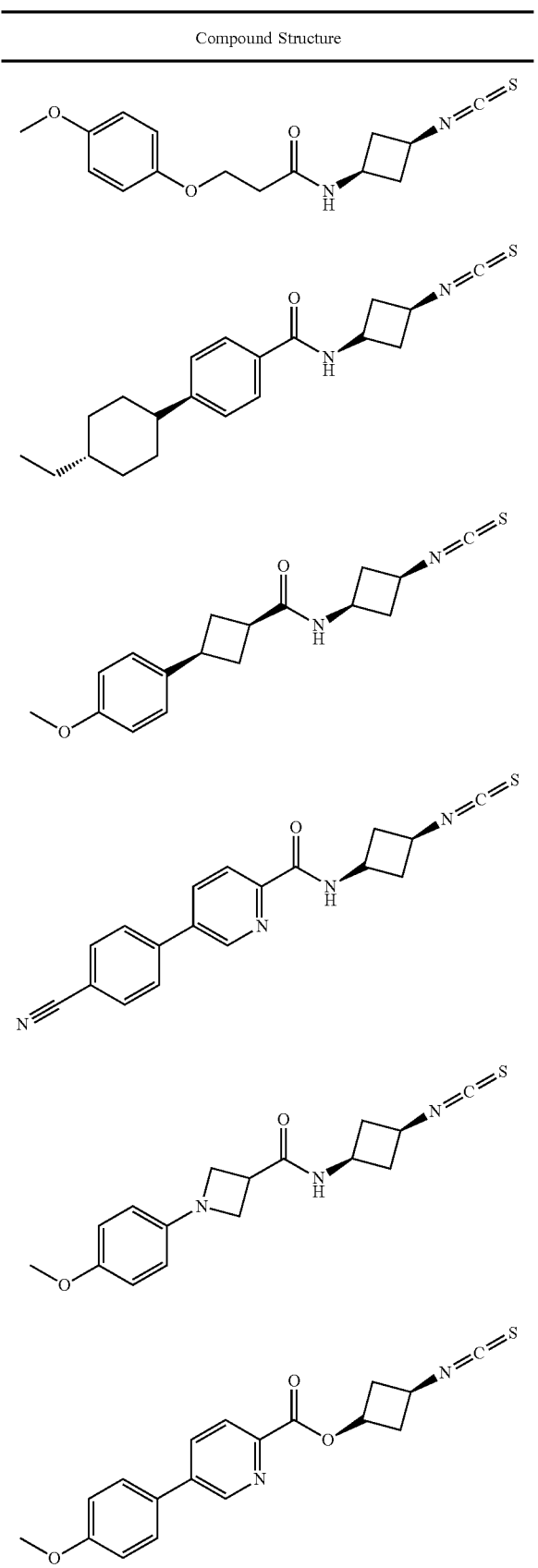
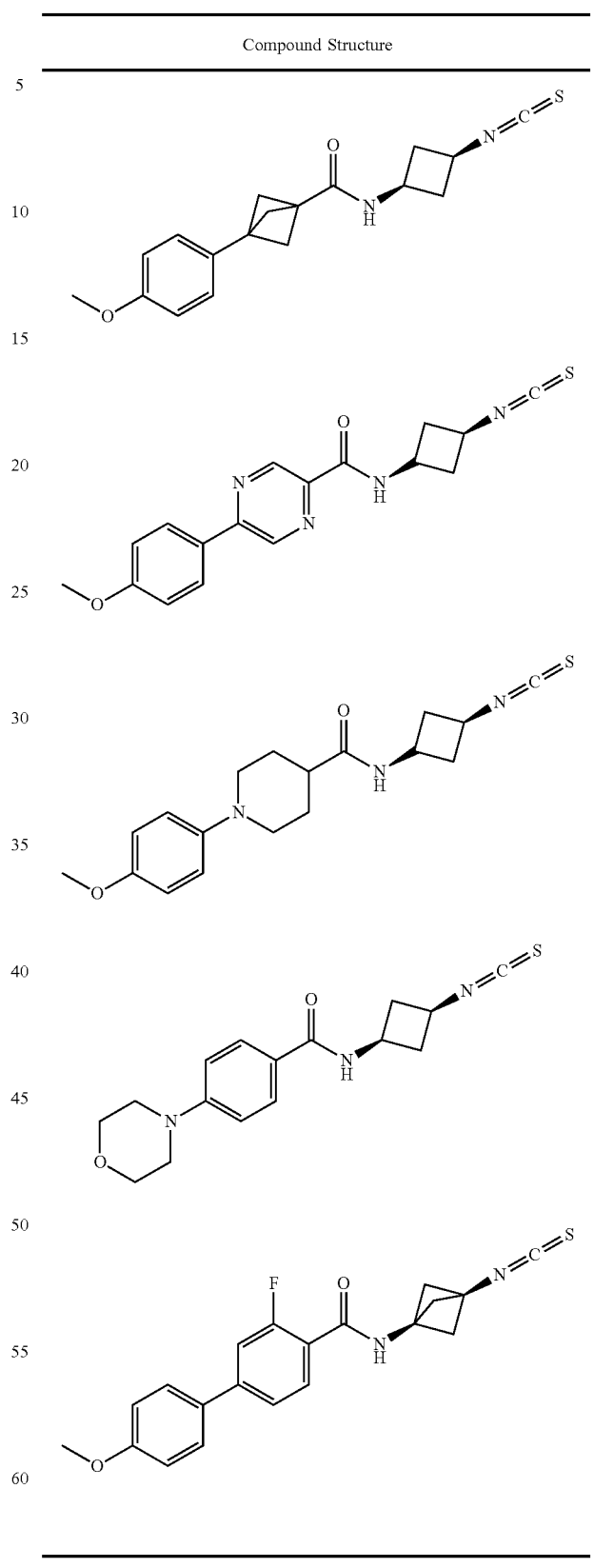
In another embodiment, the compound is a compound set forth in Table 2, or a pharmaceutically acceptable salt thereof.

TABLE 2
| Compound Structure |
| --- |
| 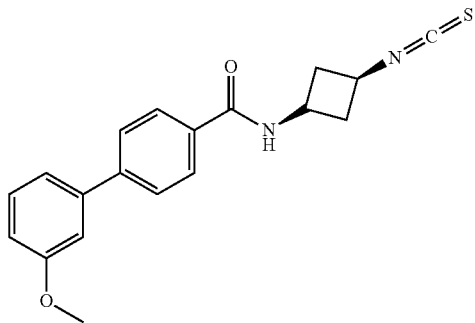 |
| 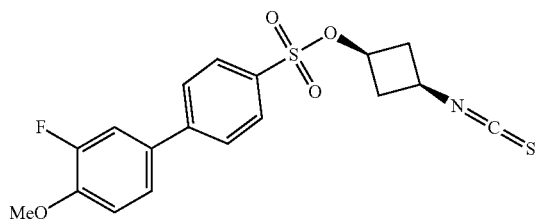 [SMILES: COc1ccc(-c2ccc(S(=O)(=O)O[C@H]3C[C@@H](N=C=S)C3)cc2)cc1F] |
| 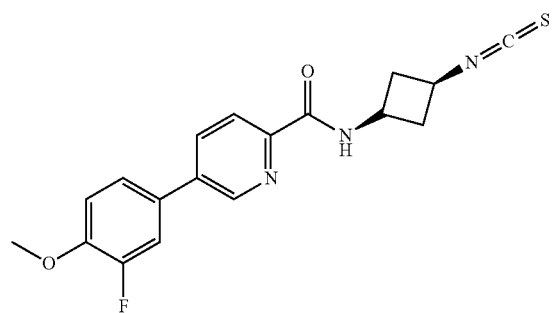 |
| 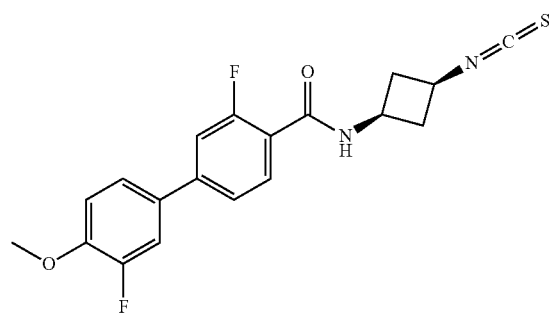 [SMILES: COc1ccc(-c2ccc(C(=O)N[C@H]3C[C@@H](N=C=S)C3)c(F)c2)cc1F] |
| 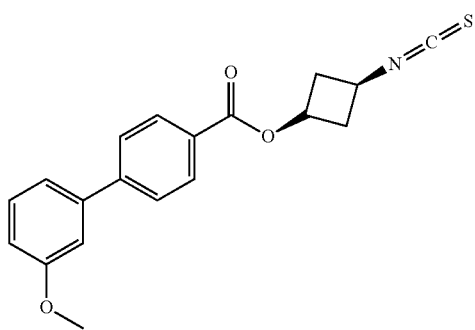 |

TABLE 2-continued

Compound Structure

TABLE 2-continued
Compound Structure
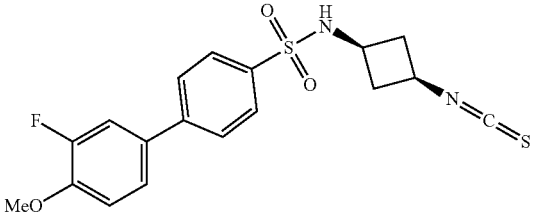 [SMILES: COc1ccc(-c2ccc(S(=O)(=O)N[C@H]3C[C@@H](N=C=S)C3)cc2)cc1F]
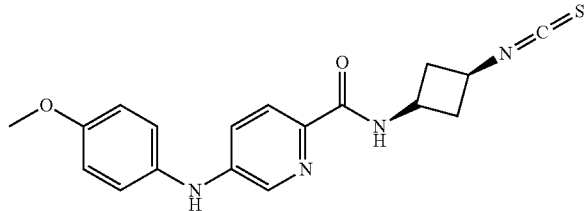
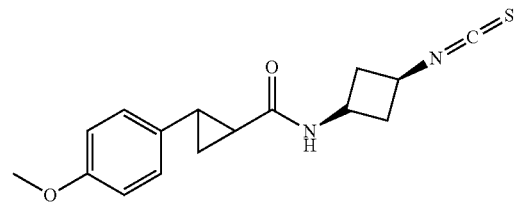
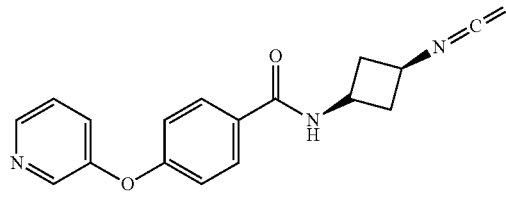
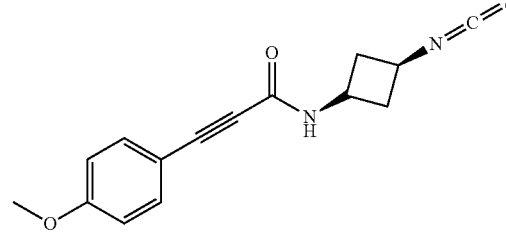
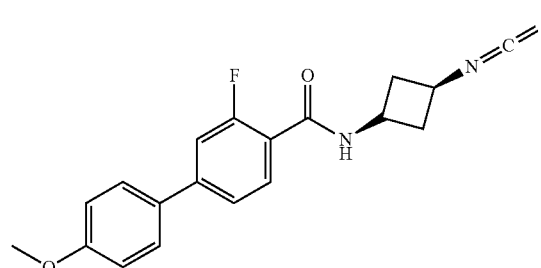
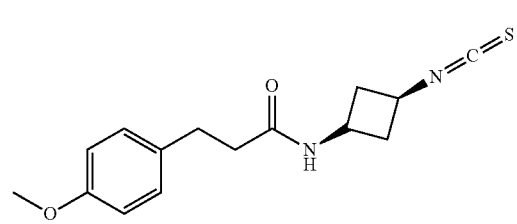

TABLE 2-continued
Compound Structure
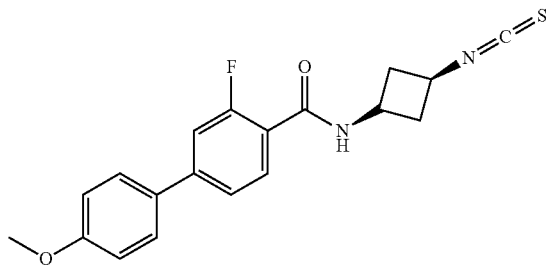
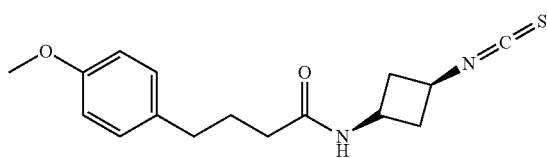
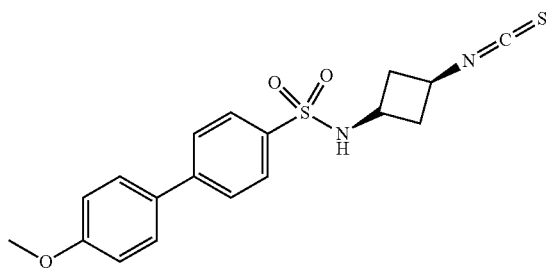
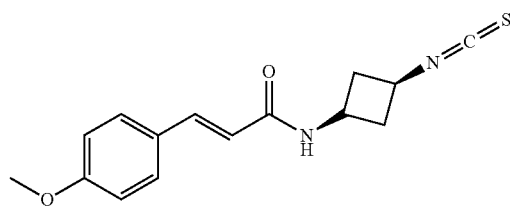
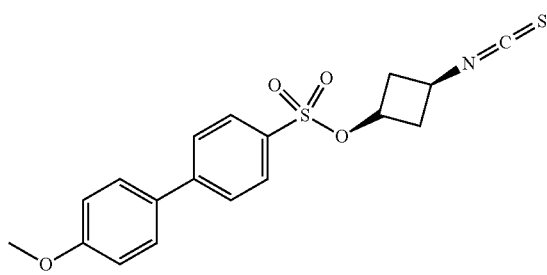
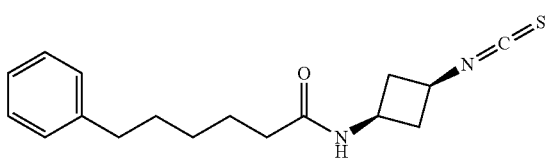 [SMILES: O=C(CCCCCc1ccccc1)N[C@H]1C[C@@H](N=C=S)C1]
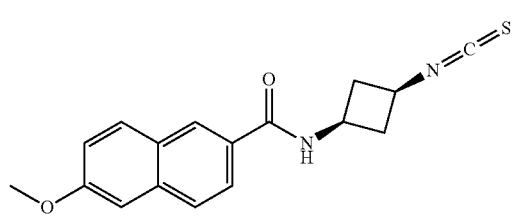 [SMILES: COc1ccc2cc(C(=O)N[C@H]3C[C@@H](N=C=S)C3)ccc2c1]

TABLE 2-continued
Compound Structure
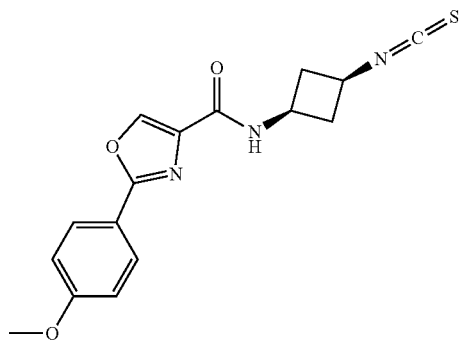 [SMILES: COc1ccc(-c2nc(C(=O)N[C@H]3C[C@@H](N=C=S)C3)co2)cc1]
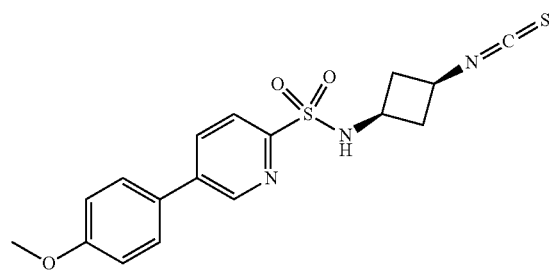 [SMILES: COc1ccc(-c2ccc(S(=O)(=O)N[C@H]3C[C@@H](N=C=S)C3)nc2)cc1]
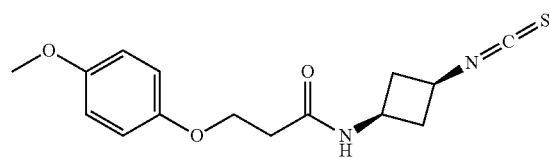 [SMILES: COc1ccc(OCCC(=O)N[C@H]2C[C@@H](N=C=S)C2)cc1]
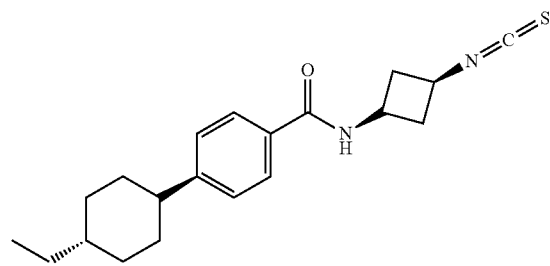
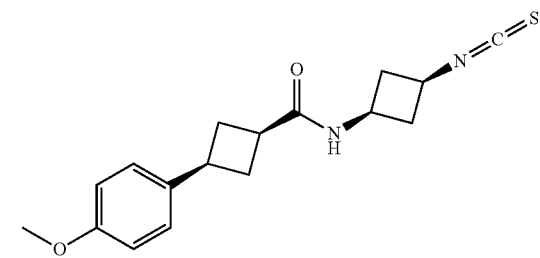 [SMILES: COc1ccc([C@H]2C[C@@H](C(=O)N[C@H]3C[C@@H](N=C=S)C3)C2)cc1]
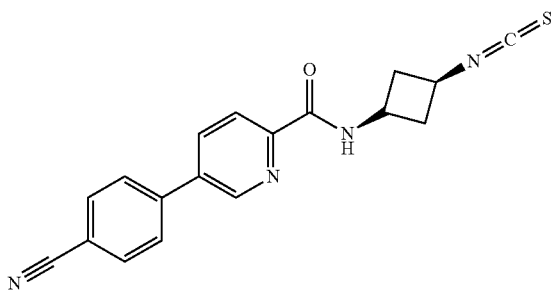

TABLE 2-continued
Compound Structure
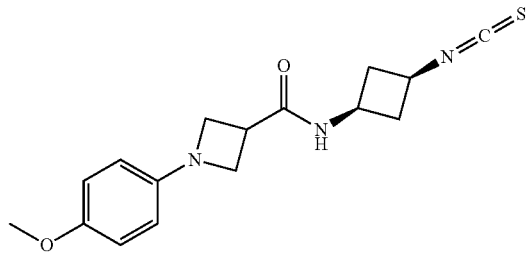
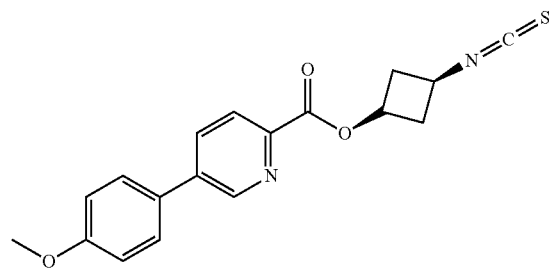
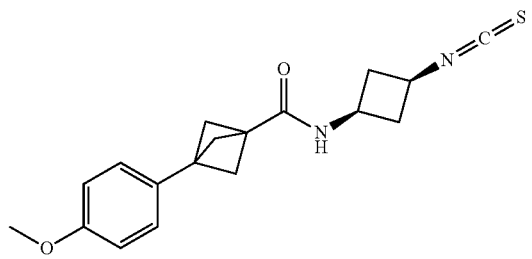 [SMILES: COc1ccc(C23CC(C(=O)N[C@H]4C[C@@H](N=C=S)C4)(C2)C3)cc1]
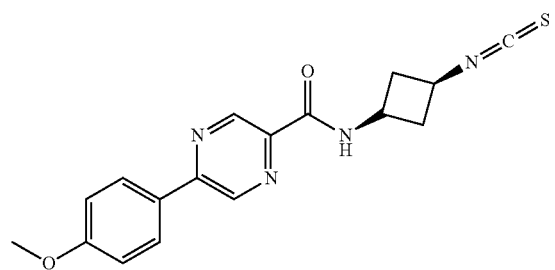
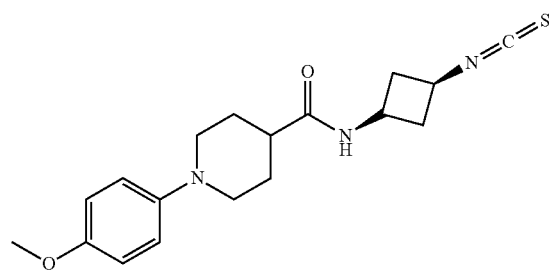

TABLE 2-continued
Compound Structure
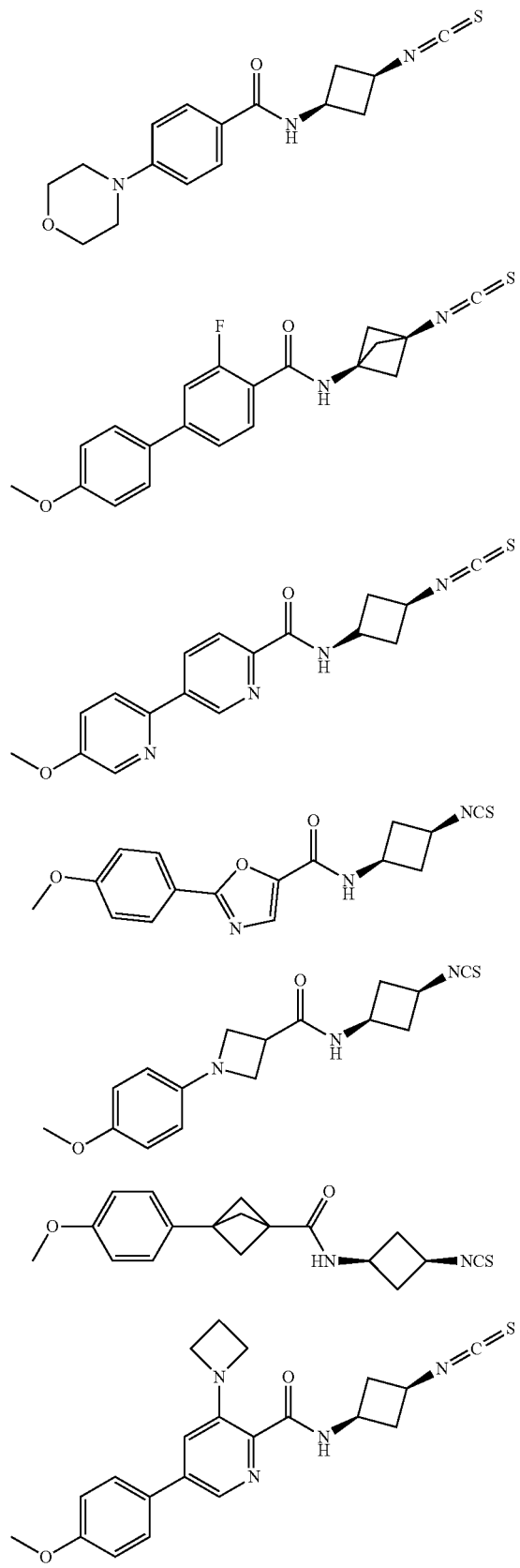

TABLE 2-continued
Compound Structure
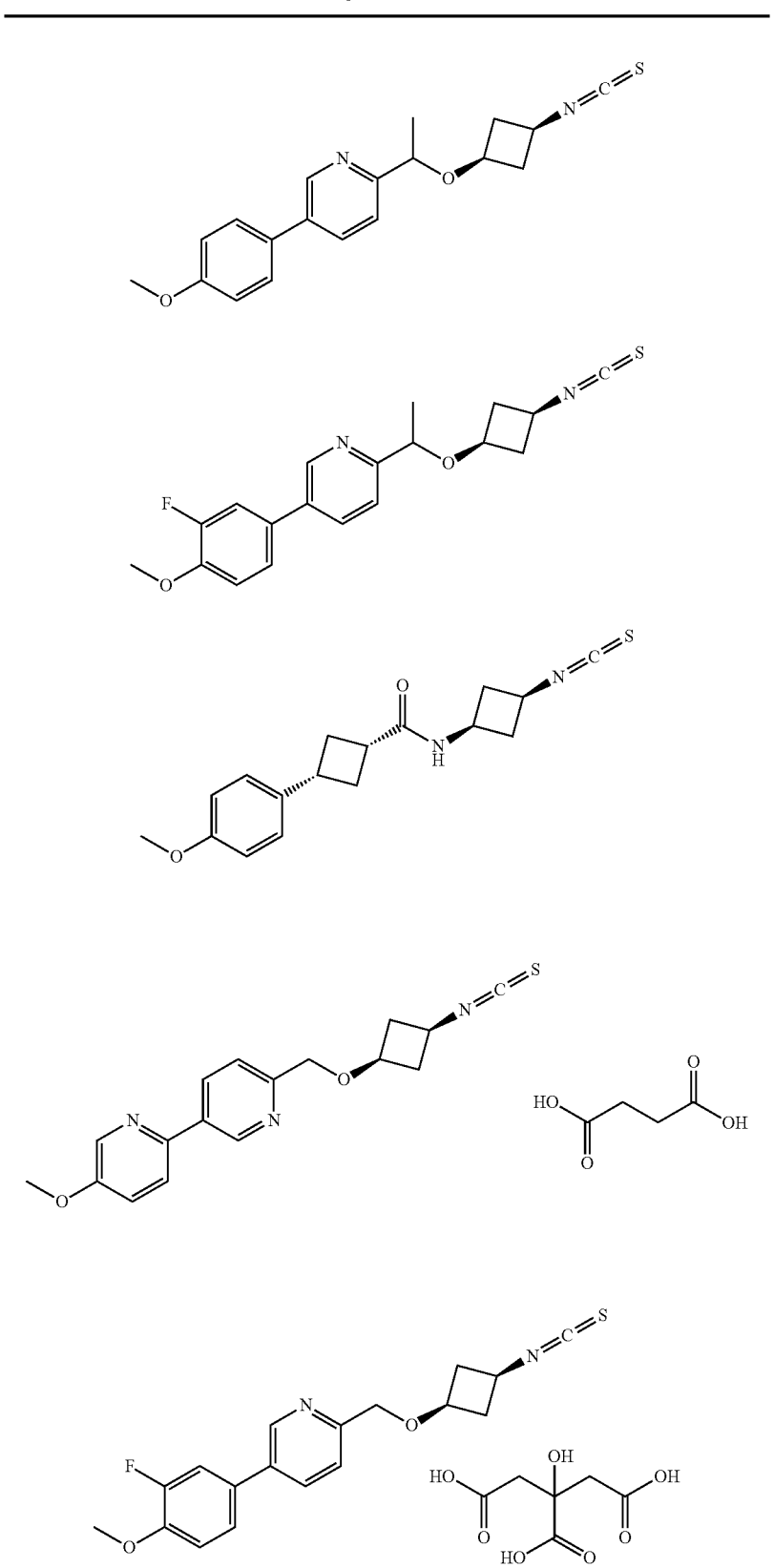

TABLE 2-continued

Compound Structure

In another embodiment, the compound is a compound set forth in Table 3, or a pharmaceutically acceptable salt thereof.

TABLE 3

Compound Structure

TABLE 3-continued

Compound Structure

TABLE 3-continued

Compound Structure

The compounds described herein can be used for the treatment of inflammatory bowel diseases, including Crohn's disease and ulcerative colitis.

Compositions

Also provided herein is a composition comprising a compound disclosed herein (e.g., a compound of Structural Formula I, II, IIa, III, IIIa), or a pharmaceutically acceptable salt thereof, and a pharmaceutically acceptable carrier. In some embodiments, a composition of the invention is formulated for oral, intravenous, subcutaneous, intraperitoneal or dermatological administration to a subject in need of the composition.

The term "carrier," as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds or their pharmaceutically acceptable salts may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. Oral formulations may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. In one embodiment, the powders and tablets contain up to 99% of the active ingredient. Capsules may contain mixtures of the active compound(s) or their pharmaceutically acceptable salt(s) with inert fillers and/or diluents such as pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins.

In one embodiment, the surface modifying agent includes nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidol silicon dioxide, phosphates, sodium dodecylsulfate, magnesium aluminum silicate, and triethanolamine.

Oral formulations herein may utilize standard delay or time release formulations to alter the absorption of the active compound(s) or their pharmaceutically acceptable salt(s). The oral formulation may also consist of administering the active ingredient in water or fruit juice, containing appropriate solubilizers or emulsifiers as needed. Liquid carriers may be used in preparing solutions, suspensions, emulsions, syrups and elixirs. The active ingredient of this disclosure may be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, sodium carboxymethyl cellulose solution), alcohols (including monohydric alcohols and polyhydric alcohols, e.g., glycols) and their derivatives, and oils (e.g., fractionated coconut oil and arachis oil).

For parenteral administration the carrier can also be an oily ester such as ethyl oleate and/or isopropyl myristate. Sterile liquid carriers are used in sterile liquid form compositions for parenteral administration. The liquid carrier for pressurized compositions may be halogenated hydrocarbon or other pharmaceutically acceptable propellant. Liquid pharmaceutical compositions, which are sterile solutions or suspensions, may be utilized by, for example, intramuscular, intraperitoneal or subcutaneous injection. Sterile solutions can also be administered intravenously.

Compositions for oral administration may be in either liquid or solid form. In one embodiment, the pharmaceutical composition is in unit dosage form, e.g., as tablets, capsules, powders, solutions, suspensions, emulsions, granules, or suppositories. In such form, the composition is sub-divided into unit dose(s) containing appropriate quantities of the active ingredient; the unit dosage forms may be packaged compositions, for example, packeted powders, vials, ampoules, prefilled syringes or sachets containing liquids.

The unit dosage form may be, for example, a capsule or tablet itself, or it may be the appropriate number of any such compositions in package form. Such unit dosage form may contain from about 1 mg/kg to about 250 mg/kg, and may be given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally and transdermally. Such administrations may be carried out using the compounds or their pharmaceutically acceptable salts disclosed herein in lotions, creams, foams, patches, suspensions, solutions, and suppositories (rectal). When administered for the treatment or inhibition of a particular disease state or disorder, it is understood that the effective dosage may vary depending upon the particular compound or salt utilized, the mode of administration, the condition, and severity of the condition being treated, as well as the various physical factors related to the individual being treated.

The compositions of this disclosure may also be administered parenterally or intraperitoneally. Solutions or suspensions of active compounds as a free base or pharmaceutically acceptable salt may be prepared in water suitably mixed with a surfactant such as hydroxylpropylcellulose. Dispersions may also be prepared in glycerol, liquid polyethylene glycols and mixtures thereof in oils. Under ordinary conditions of storage and use, these preparations contain a preservative to inhibit the growth of microorganisms. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi.

The carrier may be a solvent or dispersion medium containing, for example, water, ethanol, polyol (e.g., glycerol, propylene glycol and liquid polyethylene glycol), suitable mixtures thereof, and vegetable oils.

Methods

Also provided herein is a method for modulating (e.g., inhibiting) the activity of N-acylethanolamine hydrolyzing acid amidase, comprising contacting a receptor of N-acylethanolamine hydrolyzing acid amidase with a compound (e.g., a compound of any of Structural Formulas I, II, IIa, III and IIIa), salt or composition described herein.

Also provided herein is a method for treating a disease, disorder or condition mediated by NAAA in a subject in need thereof, comprising administering to the subject an effective amount of a compound (e.g., a compound of any of Structural Formulas I, II, IIa, III and IIIa), salt or composition described herein. A "disease, disorder or condition mediated by NAAA" or "NAAA-mediated disease, disorder or condition" refers to any disease or other deleterious disorder or condition in which NAAA plays a role, or for which modulation of N-palmitoylethanolamine (PEA) is clinically relevant (e.g., a disease, disorder or condition associated with abnormal levels of PEA).

Modulation of endogenous PEA concentration is known to exert analgesic, neuroprotective, anti-allergic and gastrointestinal tract antiinflammatory properties. PEA is an endogenous agonist for the peroxisome proliferator-activated receptor-α (PPARα), which is expressed in the intestinal mucosa of the small intestine and colon. Activation of PPARα with endogenous or exogenous ligands results in the amelioration of di-nitrobenzene sulfonic acid (DNBS)-induced colitis, suggestive of the potential role of PPARα ligands as novel therapies for gastrointestinal inflammatory conditions. However, the prolonged clinical use of exogenous PPARα ligands is linked to a variety of severe side-effects, including oncogenesis, renal dysfunction, rhabdomyolysis, and cardiovascular toxicity.

Local and systemic administration of PEA alleviates pain behaviors elicited by chemical irritants and is effective even when administered after induction of acute inflammation. For example, the PEA levels in ulcerative colitis patients were assessed by biopsy of the mast cells. Mast cells produce high amounts of PEA that potently inhibit mouse small intestine motility and visceral pain in mice. Thus, the presence of elevated levels of PEA in colonic biopsies supports the hypothesis that PEA participates in the control of visceral pain and intestinal motility.

Examples of diseases, disorders and conditions mediated by NAAA include inflammatory disorders of the gastrointestinal tract, such as inflammatory gastrointestinal motility disorder, irritable bowel syndrome and inflammatory bowel disorder, inflammation, nicotine addiction, cancer, opioid dependence, analgesia, chemotherapy-induced neuropathic pain, pain and other neuroinflammation disorders.

Also provided herein is a method of treating a disease, disorder or condition selected from an inflammatory gastrointestinal motility disorder, irritable bowel syndrome or an inflammatory bowel disorder in a subject in need thereof, comprising administering to the subject an effective amount of a compound (e.g., a compound of any of Structural Formulas I, II, IIa, III and IIIa), salt or composition described herein. In some embodiments, the disease, disorder or condition is Chrohn's disease. In some embodiments, the disease, disorder or condition is ulcerative colitis.

As used herein, the terms "treat," "treating," or "treatment," mean to counteract a medical condition to the extent that the medical condition is improved according to a clinically-acceptable standard.

In an embodiment, the subject (e.g., patient) is a mammal (e.g., human, non-human primate, cow, sheep, goat, horse, dog, cat, rabbit, guinea pig, rat, mouse or other bovine, ovine, equine, canine, feline, or rodent organism). In a particular embodiment, the subject is a human. A "subject in need thereof" refers to a subject who has, or is at risk for developing, a disease, disorder or condition described herein (e.g., a NAAA-mediated disease, disorder or condition). A skilled medical professional (e.g., physician) can readily determine whether a subject has, or is at risk for developing, a disease or condition described herein.

The terms "effective amount," "therapeutically effective amount" and "effective dosage" as used herein, refer to the amount of a compound or salt that, when administered to a subject, is effective to at least partially ameliorate (and, in preferred embodiments, cure) a condition from which the patient is suspected to suffer. It is understood that the effective dosage of the active compounds or salts of this disclosure may vary depending upon the particular compound or salt utilized, the mode of administration, the condition, and severity thereof, of the condition being treated, as well as the various physical factors related to the individual being treated.

An effective amount of the compound or salt to be administered can be determined by a clinician of ordinary skill using the guidance provided herein and other methods known in the art, and is dependent on several factors including, for example, the particular compound or salt chosen, the subject's age, sensitivity, tolerance to drugs and overall well-being. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects (e.g., immunogenic response, nausea, dizziness, gastric upset, hyperviscosity syndromes, congestive heart failure, stroke, pulmonary edema).

For treating IBD and inflammatory diseases, generally, satisfactory results may be obtained when the compounds or salts of this disclosure are administered to the individual in need at a daily dosage of from about 1 mg to about 10 mg per kilogram of body weight, preferably administered once per day or in divided doses two to six times per day, or in a sustained release form. For most large mammals, the total daily dosage is from about 10 mg to about 100 mg preferably from about 5 to about 20 mg. In the case of a 70 kg human adult, the total daily dose will generally be from about 10 mg to about 150 mg and may be adjusted to provide the optimal therapeutic result. This regimen may be adjusted to provide the optimal therapeutic response.

A compound described herein (e.g., a compound of any of Structural Formulas I-IIIa), or a pharmaceutically acceptable salt thereof, can be administered in a single dose or as multiple doses, for example, in an order and on a schedule suitable to achieve a desired therapeutic effect. Suitable dosages and regimens of administration can be determined by a clinician of ordinary skill.

A compound described herein (e.g., a compound of any of Structural Formulas I-IIIa), or a pharmaceutically acceptable salt thereof, can also be administered in combination with one or more other therapies or treatments. With respect to the administration of a compound or salt in combination with one or more other therapies or treatments, the compound or salt is typically administered as a single dose (by, e.g., injection, infusion, orally), followed by repeated doses at particular intervals (e.g., one or more hours) if desired or indicated.

When administered in a combination therapy, the compound or salt can be administered before, after or concurrently with the other therapy (e.g., an additional agent(s)). When co-administered simultaneously (e.g., concurrently), the compound or salt and other therapy can be in separate formulations or the same formulation. Alternatively, the compound or salt and other therapy can be administered sequentially, as separate compositions, within an appropriate time frame as determined by a skilled clinician (e.g., a time sufficient to allow an overlap of the pharmaceutical effects of the therapies).

A compound described herein (e.g., a compound of any of Structural Formulas I-IIIa), or a pharmaceutically acceptable salt thereof, can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound or salt and the particular disease to be treated. Administration can be local or systemic as indicated. The preferred mode of administration can vary depending on the particular compound or salt chosen.

The actual dose of a therapeutic agent and treatment regimen can be determined by the physician, taking into account the nature of the disease, other therapies being given, and subject characteristics.

EXEMPLIFICATION

Method A

N-((1s,3s)-3-isothiocyanatocyclobutyl)carboxamides 8 and N-((1s,3s)-3-isothio-cyanatocyclobutyl)carboxylates 9 were prepared according to scheme 1. Cyclobutane-amine 1 or cyclobutane-alcohol 2 were coupled with the appropriate substituted-carboxylic acid 3 by using coupling agent 1-ethyl-3-(3-dimethylaminopropyl) carbodiimide hydrochloride (EDC.HCl) to afford the amide 4 or ester 5, respectively. Deprotection of the BOC group of 4 and 5 with trifluoroacetic acid afforded the free amines 6 and 7. Amines 6 or 7 were treated with 1,1'-thiocarbonyldi-2(1H)-pyridone to afford the corresponding N-((1s,3s)-3-isothio-cyanatocyclobutyl)carboxamides 8 and N-((1s,3s)-3-isothiocyanatocyclobutyl)carboxylates 9, respectively.

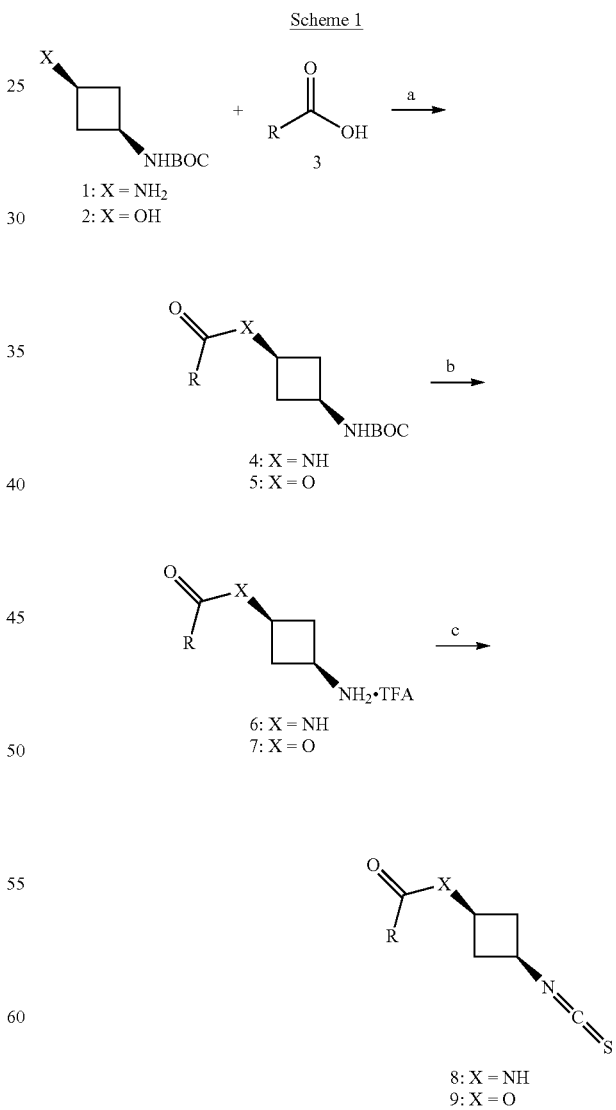

Reagents: (a) EDC, DIEA, HOBt, DMF; (b) TFA, CH$_2$Cl$_2$; (c) 1,1'-thiocarbonyldi-2(1H)-pyridone, Et$_3$N, CH$_2$Cl$_2$

Example 1. (E)-N-((1s, 3s)-3-Isothiocyanatocyclobutyl)-3-(4-methoxyphenyl)acrylamide

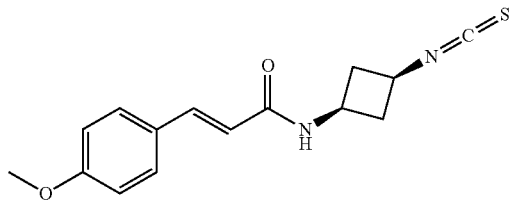 [SMILES: COc1ccc(/C=C/C(=O)N[C@H]2C[C@@H](N=C=S)C2)cc1]

Step a: tert-Butyl ((1s, 3s)-3-((E)-3-(4-methoxyphenyl)acrylamido)cyclobutyl)carbamate. 4-Methoxycinnamic acid (48 mg, 0.27 mmol) and 1-hydroxybenzotriazole (44 mg, 0.32 mmol) were added to a stirring solution of tert-butyl (cis-3-aminocyclobutyl)carbamate (50 mg, 0.27 mmol) in DMF (3 mL) under an argon atmosphere. EDC.HCl (62 mg, 0.32 mmol) and diisopropylethylamine (0.12 mL, 0.67 mmol) were added to the reaction mixture. The resulting mixture was stirred for 24 h at room temperature. The reaction mixture was then diluted with EtOAc (25 mL) and washed with water (2×15 mL) and brine. The organic extracts were dried over anhydrous MgSO$_4$ and the solvents were removed under reduced pressure to afford tert-butyl ((1s, 3 s)-3-((E)-3-(4-methoxyphenyl)acrylamido)cyclobutyl)carbamate as white solid (70 mg, 75% yield): $^1$H NMR (500 MHz, CDCl$_3$) δ 7.57 (d, J=15.5 Hz, 1H), 7.43 (d, J=9 Hz, 2H), 6.88 (d, J=9 Hz, 2H), 6.21 (d, J=15.5 Hz, 1H), 5.72-5.68 (m, 1H), 4.74-4.69 (m, 1H), 4.20-4.15 (m, 1H), 3.81 (s, 3H), 2.80-2.56 (m, 2H), 1.93-1.72 (m, 2H), 1.43 (s, 9H).

Step b: (E)-N-((1s, 3s)-3-Aminocyclobutyl)-3-(4-methoxyphenyl)acrylamide.TFA salt. Trifluoroacetic acid (0.10 mL, 1.87 mmol) was gradually added to a stirring solution of tert-butyl ((1s, 3 s)-3-((E)-3-(4-methoxyphenyl)acrylamido)cyclobutyl)carbamate (65 mg, 0.19 mmol) in dichloromethane (3 mL). The resulting reaction mixture was stirred at room temperature for 18 hours. Then, the mixture was concentrated under vacuum and chloroform (3×15 mL) was added and evaporated under reduced pressure to ensure the removal of the trifluoroacetic acid. The product (E)-N-((1s, 3 s)-3-aminocyclobutyl)-3-(4-methoxyphenyl)acrylamide.TFA was used in the next step without further purification.

Step c: (E)-N-((1s, 3s)-3-Isothiocyanatocyclobutyl)-3-(4-methoxyphenyl)acrylamide. Triethylamine (0.13 mL, 0.94 mmol) was added into a stirring solution of (E)-N-((1s, 3s)-3-aminocyclobutyl)-3-(4-methoxyphenyl)acrylamide-.TFA (67 mg, 0.19 mmol) in dichloromethane (4 mL) under argon. 1,1'-Thiocarbonyldi-2(1H)-pyridone (87 mg, 0.37 mmol) was added after 10 min. The resulting reaction mixture was stirred at room temperature and monitored by TLC. After two hours, the reaction mixture was diluted with dichloromethane (25 mL) and washed with water (2×15 mL). The organic layer was dried over MgSO$_4$ and the solvent was removed under reduced pressure. The resulting residue was purified on silica gel (Biotage; eluting solvents hexanes:EtOAc 1/1 ratio) to afford (E)-N-((1r, 3r)-3-isothiocyanatocyclobutyl)-3-(4-methoxyphenyl)acrylamide as a white solid (40 mg, 74% yield); $^1$H NMR (500 MHz, CDCl$_3$) δ 7.58 (d, J=15 Hz, 1H), 7.44 (d, J=8.5 Hz, 2H), 6.89 (d, J=9 Hz, 2H), 6.22 (d, J=15.5 Hz, 1H), 5.70 (d, J=7.5 Hz, 1H), 4.38-4.28 (m, 1H), 3.88-3.82 (m, 4H), 2.98-2.92 (m, 2H), 2.21-2.15 (m, 2H).

The following examples were prepared according to Method A.

Example 2. N-((1r, 3r)-3-Isothiocyanatocyclobutyl)-3'-methoxy-[1,1'-biphenyl]-4-carboxamide

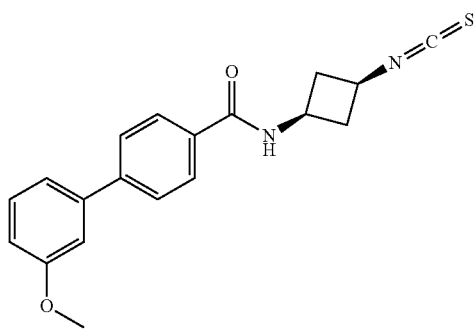

$^1$H NMR (500 MHz, CDCl$_3$) δ 7.83 (d, J=8 Hz, 2H), 7.67 (d, J=8 Hz, 2H), 7.40 (t, J=8 Hz, 1H), 7.20 (d, J=8.5 Hz, 1H), 7.13 (s, 1H), 6.95 (dd, J=2.5, 8.5 Hz, 1H), 6.32 (d, J=8 Hz, 1H), 4.44-4.37 (m, 1H), 3.95-3.89 (m, 1H), 3.88 (s, 3H), 3.05-3.00 (m, 2H), 2.31 (m, 2H).

Example 3. (1r, 3r)-3-Isothiocyanatocyclobutyl 3'-methoxy-[1,1'-biphenyl]-4-carboxylate

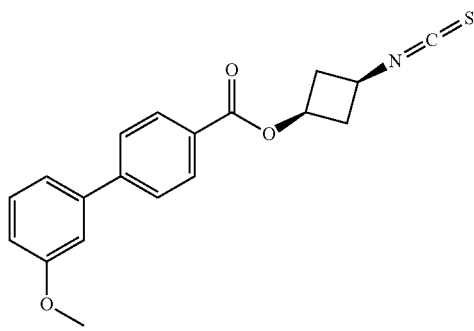 [SMILES: COc1cccc(-c2ccc(C(=O)O[C@H]3C[C@@H](N=C=S)C3)cc2)c1]

$^1$H NMR (500 MHz, CDCl$_3$) δ 8.10 (d, J=8 Hz, 2H), 7.78 (d, J=8 Hz, 2H), 7.40 (t, J=8 Hz, 1H), 7.26 (d, J=6 Hz, 1H), 7.15 (s, 1H), 6.96 (d, J=8.5 Hz, 1H), 5.02-4.98 (m, 1H), 3.93-3.88 (m, 1H), 3.88 (s, 3H), 3.11-3.05 (m, 2H), 2.57-2.51 (m, 2H).

Example 4. N-((1r, 3r)-3-Isothiocyanatocyclobutyl)-4-(4-methoxyphenoxy)benzamide

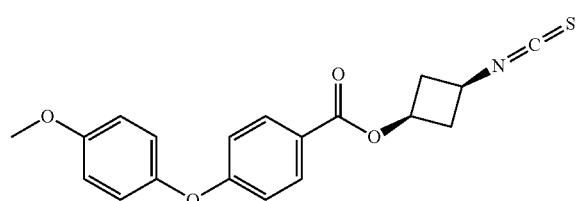

$^1$H NMR (500 MHz, CDCl$_3$) δ 7.71 (d, J=6.5 Hz, 2H), 7.01 (d, J=6 Hz, 2H), 6.95-6.91 (m, 4H), 6.21 (d, J=7.5 Hz,

1H), 4.37-4.35 (m, 1H), 3.92-3.88 (m, 1H), 3.83 (s, 3H), 3.02-2.97 (m, 2H), 2.28-2.22 (m, 2H); MS (ESI) m/z 355.47 [M+1]⁺.

Example 5. N-((1r, 3r)-3-Isothiocyanatocyclobutyl)-4-morpholinobenzamide

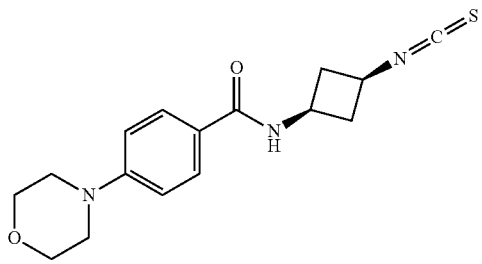 [SMILES: O=C(N[C@H]1C[C@@H](N=C=S)C1)c1ccc(N2CCOCC2)cc1]

¹H NMR (500 MHz, CDCl₃) δ 7.70 (d, J=9 Hz, 2H), 6.89 (d, J=8.5 Hz, 2H), 6.17 (d, J=8 Hz, 1H), 4.40-4.34 (m, 1H), 3.91-3.85 (m, 5H), 3.27-3.25 (m, 4H), 3.02-2.97 (m, 2H), 2.27-2.21 (m, 2H); MS (ESI) m/z 318.46 [M+1]⁺.

Example 6. N-((1r, 3r)-3-Isothiocyanatocyclobutyl)-4-(pyridin-3-yloxy)benzamide

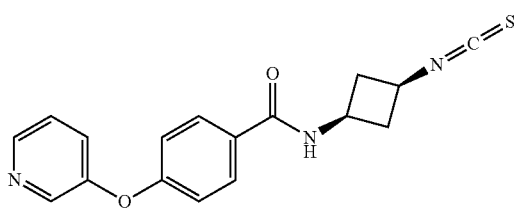 [SMILES: O=C(N[C@H]1C[C@@H](N=C=S)C1)c1ccc(Oc2cccnc2)cc1]

¹H NMR (500 MHz, CDCl₃) δ 8.46-8.44 (m, 1H), 7.78 (d, J=9 Hz, 2H), 7.37-7.31 (m, 2H), 7.05 (dd, J=9, 2 Hz, 2H), 6.25 (d, J=2 Hz, 1H), 4.42-4.33 (m, 1H), 3.93-3.89 (m, 1H), 3.04-2.99 (m, 2H), 2.29-2.23 (m, 2H); MS (ESI) m/z 326.43 [M+1]⁺.

Example 7. 3-Fluoro-N-((1r, 3r)-3-isothiocyanatocyclobutyl)-4'-methoxy-[1,1'-biphenyl]-4-carboxamide

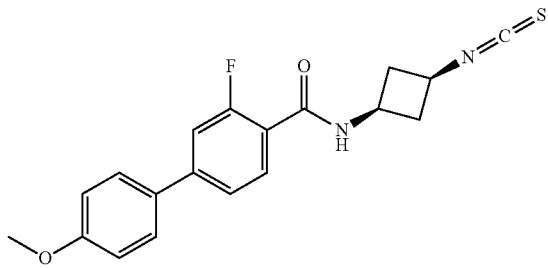 [SMILES: COc1ccc(-c2ccc(C(=O)N[C@H]3C[C@@H](N=C=S)C3)c(F)c2)cc1]

¹H NMR (500 MHz, CDCl₃) δ 8.12 (t, J=8.5 Hz, 1H), 7.57 (d, J=6.5 Hz, 2H), 7.47 (dd, J=8.5, 1.5 Hz, 1H), 7.34 (dd, J=14, 2 Hz, 1H), 7.01 (dd, J=7, 2 Hz, 2H), 6.93-6.88 (m, 1H), 4.43-4.38 (m, 1H), 3.93-3.90 (m, 1H), 3.87 (s, 1H), 3.03-3.01 (m, 2H), 2.30-2.28 (m, 2H); MS (ESI) m/z 357.43 [M+1]⁺.

Example 8. (1r, 3r)-3-Isothiocyanatocyclobutyl 3-fluoro-4'-methoxy-[1,1'-biphenyl]-4-carboxylate

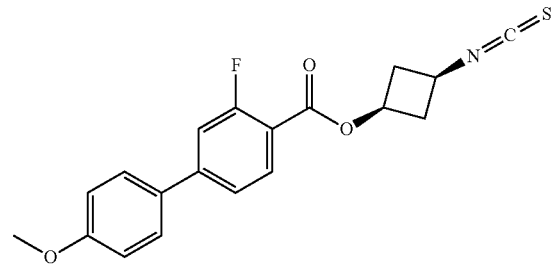 [SMILES: COc1ccc(-c2ccc(C(=O)O[C@H]3C[C@@H](N=C=S)C3)c(F)c2)cc1]

¹H NMR (500 MHz, CDCl₃) δ 7.98 (t, J=8 Hz, 1H), 7.57 (d, J=8.5 Hz, 2H), 7.42 (dd, J=8.5, 2 Hz, 1H), 7.35 (d, J=12.5 Hz, 1H), 7.01 (d, J=8.5 Hz, 2H), 5.01-4.97 (m, 1H), 3.93-3.89 (m, 1H), 3.87 (s, 1H), 3.08-3.04 (m, 2H), 2.55-2.53 (m, 2H).

Example 9. 3-Fluoro-N-(3-isothiocyanatobicyclo[1.1.1]pentan-1-yl)-4'-methoxy-[1,1'-biphenyl]-4-carboxamide

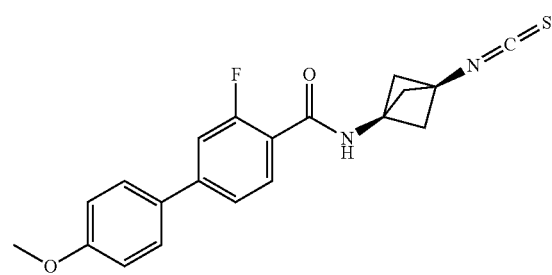 [SMILES: COc1ccc(-c2ccc(C(=O)N[C@]34C[C@](N=C=S)(C3)C4)c(F)c2)cc1]

tert-Butyl N-(3-aminobicyclo[1.1.1]pentan-1-yl)carbamate was used as the starting amine in Method A for this example.

¹H NMR (500 MHz, CDCl₃) δ 8.10 (t, J=8 Hz, 1H), 7.56 (d, J=7 Hz, 2H), 7.48 (dd, J=8.5, 1.5, 1H), 7.31 (dd, J=13.5, 1 Hz, 1H), 7.12 (d, J=10 Hz, 1H), 7.00 (d, J=9 Hz, 2H), 3.86 (s, 3H), 2.60 (s, 6H); MS (ESI) m/z 369.46 [M+1]⁺.

Example 10. N-((1s, 3 s)-3-Isothiocyanatocyclobutyl)-6-methoxy-2-naphthamide

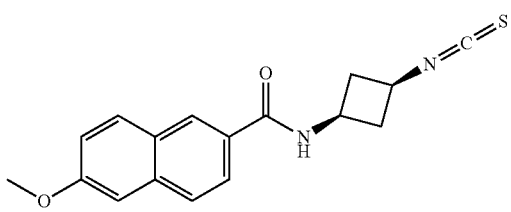 [SMILES: COc1ccc2cc(C(=O)N[C@H]3C[C@@H](N=C=S)C3)ccc2c1]

¹H NMR (500 MHz, CDCl₃) δ 8.21 (s, 1H), 7.82 (m, 3H), 7.22 (dd, J=9.5, 2.5 Hz, 1H), 7.16 (s, 1H), 6.41 (d, J=7 Hz, 1H), 4.45-4.42 (m, 1H), 3.95 (s, 3H), 3.93-3.90 (m, 1H), 3.07-3.03 (m, 2H), 2.34-2.29 (m, 2H); MS (ESI) m/z 313.41 [M+1]⁺.

Example 11. 4-((1s, 4s)-4-Ethylcyclohexyl)-N-((1r, 3R)-3-isothiocyanatocyclobutyl) benzamide

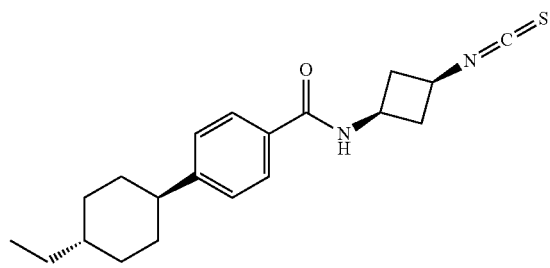 [SMILES: CC[C@H]1CC[C@H](c2ccc(C(=O)N[C@H]3C[C@@H](N=C=S)C3)cc2)CC1]

¹H NMR (500 MHz, CDCl₃) δ 7.68 (d, J=10 Hz, 2H), 7.28 (d, J=8 Hz, 2H), 6.21 (d, J=7.5 Hz, 1H), 4.42-4.33 (m, 1H), 3.93-3.87 (m, 1H), 3.03-2.97 (m, 2H), 2.54-2.49 (m, 1H), 2.27-2.21 (m, 2H), 1.90 (d, J=10 Hz, 4H), 1.49-1.42 (m, 1H), 1.29-1.21 (m, 4H), 1.08-1.02 (m, 2H), 0.93 (t, J=7 Hz, 3H); MS (ESI) m/z 343.51 [M+1]⁺.

Example 12. N-((1r, 3r)-3-Isothiocyanatocyclobutyl)-3-(4-methoxyphenyl)propanamide

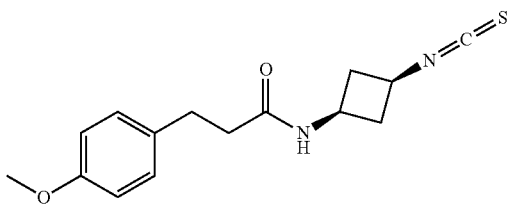 [SMILES: COc1ccc(CCC(=O)N[C@H]2C[C@@H](N=C=S)C2)cc1]

¹H NMR (500 MHz, CDCl₃) δ 7.10 (d, J=9 Hz, 2H), 6.83 (d, J=9 Hz, 2H), 5.39 (d, J=7.5 Hz, 1H), 4.14-4.09 (m, 1H), 3.80-3.76 (m, 4H), 2.89-2.81 (m, 4H), 2.41 (t, J=7.5 Hz, 2H), 2.03-1.97 (m, 2H).

Example 13. N-((1r, 3r)-3-Isothiocyanatocyclobutyl)-3-(4-methoxyphenyl)propiolamide

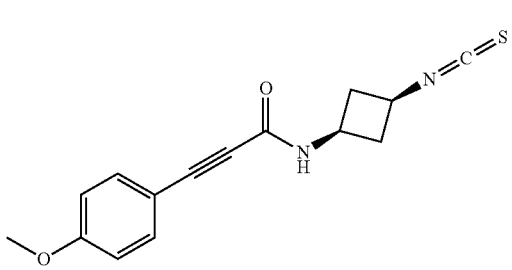 [SMILES: COc1ccc(C#CC(=O)N[C@H]2C[C@@H](N=C=S)C2)cc1]

¹H NMR (500 MHz, CDCl₃) δ 7.97 (d, J=9.5 Hz, 2H), 7.60 (s, 1H), 6.96 (d, J=9 Hz, 2H), 4.18-4.14 (m, 1H), 3.88-3.81 (m, 4H), 2.91-2.86 (m, 2H), 2.24-2.18 (m, 2H).

Example 14. N-((1r, 3r)-3-Isothiocyanatocyclobutyl)-2-(4-methoxyphenyl)cyclopropane-1-carboxamide

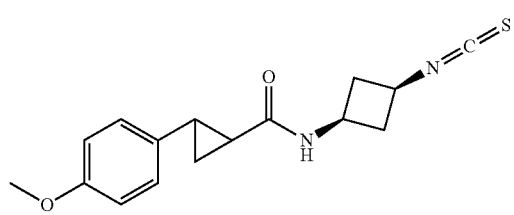 [SMILES: COc1ccc(C2CC2C(=O)N[C@H]2C[C@@H](N=C=S)C2)cc1]

¹H NMR (500 MHz, CDCl₃) δ 7.00 (d, J=9 Hz, 2H), 6.82 (d, J=8.5 Hz, 2H), 5.74 (s, 1H), 4.22-4.19 (m, 1H), 3.85-3.80 (m, 1H), 3.77 (s, 3H), 2.91-2.89 (m, 2H), 2.44-2.40 (m, 1H), 2.16-2.11 (m, 2H), 1.46-1.44 (m, 1H), 1.20-1.19 (m, 2H).

Example 15. N-((1r, 3r)-3-Isothiocyanatocyclobutyl)-4-(4-methoxyphenyl)butanamide

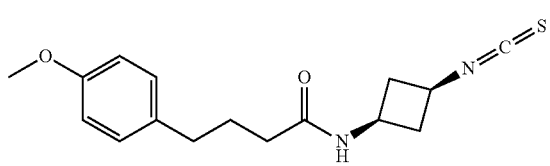 [SMILES: COc1ccc(CCCC(=O)N[C@H]2C[C@@H](N=C=S)C2)cc1]

¹H NMR (500 MHz, CDCl₃) δ 7.08 (d, J=8.5 Hz, 2H), 6.82 (d, J=8 Hz, 2H), 5.48 (s, 1H), 4.18-4.12 (m, 1H), 3.84-3.78 (m, 4H), 2.89-2.86 (m, 2H), 2.59 (t, J=8 Hz, 2H), 2.13-2.06 (m, 4H), 1.92-1.89 (m, 2H).

Example 16. N-((1r, 3r)-3-Isothiocyanatocyclobutyl)-3-(4-methoxyphenyl)isoxazole-5-carboxamide

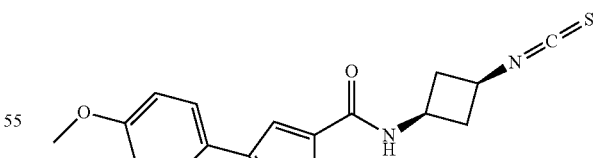

¹H NMR (500 MHz, CDCl₃) δ 7.71 (d, J=8.5 Hz, 2H), 6.99-6.96 (m, 3H), 6.79 (s, 1H), 4.34-4.28 (m, 1H), 3.92-3.87 (m, 1H), 3.84 (s, 3H), 2.99-2.92 (m, 2H), 2.33-2.29 (m, 2H).

Example 17. N-((1r, 3 r)-3-Isothiocyanatocyclobutyl)-1-(4-methoxyphenyl)piperidine-4-carboxamide

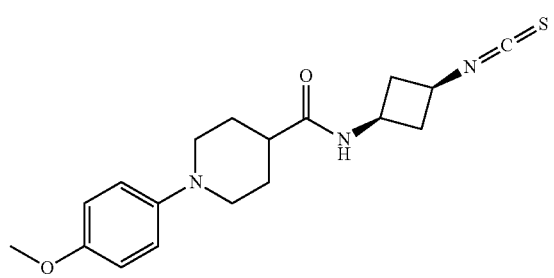 [SMILES: COc1ccc(N2CCC(C(=O)N[C@H]3C[C@@H](N=C=S)C3)CC2)cc1]

¹H NMR (500 MHz, CDCl₃) δ 6.90 (d, J=9 Hz, 2H), 6.82 (d, J 8.5 Hz, 2H), 5.61 (d, J=7 Hz, 1H), 4.22-4.16 (m, 1H), 3.85-3.81 (m, 1H), 3.56-3.51 (m, 2H), 2.94-2.88 (m, 2H), 2.65 (dt, J=11.5, 2.5 Hz, 2H), 2.14-2.08 (m, 3H), 1.93-1.84 (m, 4H).

Method B

N-((1s,3s)-3-isothiocyanatocyclobutyl)carboxamides 10 and N-((1s,3s)-3-isothio-cyanatocyclobutyl)carboxylates 11 with a bi-aryl moiety were prepared according to scheme 2. Cyclobutyl-anamine 1 or cyclobutyl-alcohol 2 were coupled with aryl-bromide carboxylic acids 3 as described in method A to afford the corresponding amides 4 or esters 5, respectively. Palladium mediated cross-coupling reaction between aryl-bromide (4) or (5) with an appropriately substituted boronic acid afforded the bi-aryl analogs 6 and 7, respectively. Tetrakis(triphenylphosphine)palladium(0) was used in the process of the invention with K₂CO₃ as the inorganic base. Deprotection of the BOC group on 6 and 7 afforded the free amines 8 and 9, respectively Amines 8 or 9 were treated with 1,1'-thiocarbonyldi-2(1H)-pyridone to afford the bi-aryl N-((1s,3s)-3-isothiocyanatocyclobutyl)carboxamides 10 and N-((1s,3s)-3-isothio-cyanatocyclobutyl)carboxylates 11, respectively.

Scheme 2

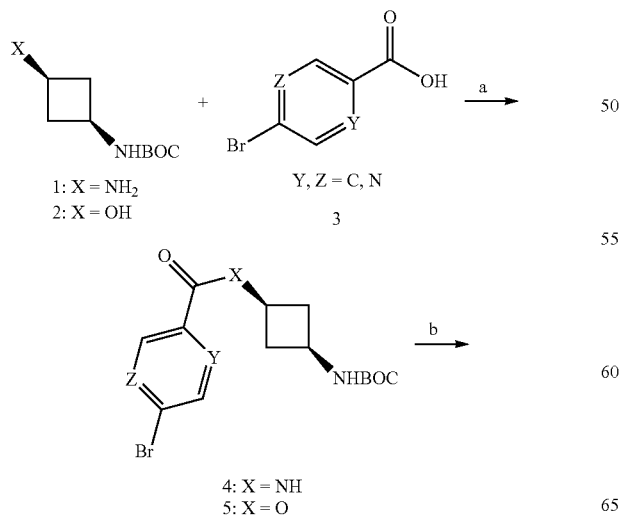

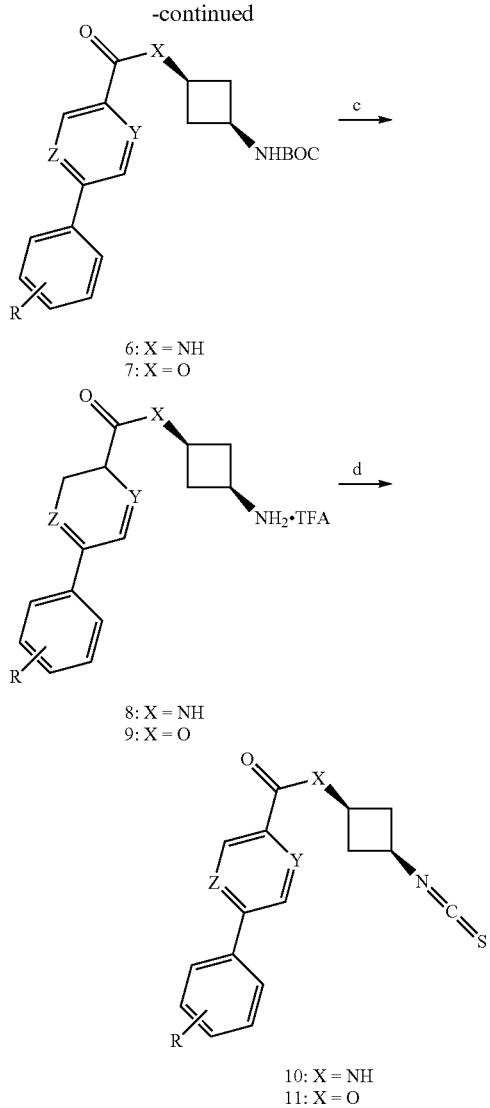

Reagents: (a) EDC, DIEA, HOBt, DMF; (b) Substituted-boronic acid, Pd(PPh₃)₄, K₂CO₃, Dioxane, H₂O, 110° C.; (c) TFA, CH₂Cl₂; (d) 1,1'-thiocarbonyldi-2(1H)-pyridone, Et₃N, CH₂Cl₂

Example 18. N-((1s, 3 s)-3-Isothiocyanatocyclobutyl)-5-(4-methoxyphenyl)picolinamide

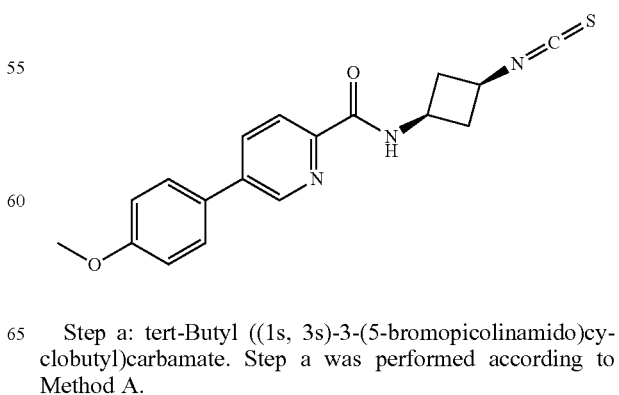

Step a: tert-Butyl ((1s, 3s)-3-(5-bromopicolinamido)cyclobutyl)carbamate. Step a was performed according to Method A.

¹H NMR (500 MHz, CDCl₃) δ 8.58 (s, 1H), 8.05 (d, J=8.5 Hz, 1H), 7.97 (dd, J=8.5, 2.5 Hz, 2H), 4.74-4.66 (m, 1H), 4.24-4.19 (m, 1H), 3.92-3.88 (m, 1H), 2.89-2.83 (m, 2H), 2.00-1.91 (m, 2H).

Step b: tert-Butyl ((1s, 3s)-3-(5-(4-methoxyphenyl)picolinamido)cyclobutyl)carbamate. Tert-butyl ((1s, 3s)-3-(5-bromopicolinamido)cyclobutyl)carbamate (150 mg, 0.41 mmol), 4-methoxyphenyl-boronic acid (123 mg, 0.81 mmol), K₂CO₃ (169 mg, 1.22 mmol), dioxane (10 mL) and water (2.5 mL) were added in a microwave vessel. The mixture was degassed with argon for 10 minutes and tetrakis(triphenylphosphine)palladium(0) (9.4 mg, 0.01 mmol) was added and the argon flow continued for 5 additional minutes. Then, the vessel was sealed and microwaved at 110° C. for 2 hours. The mixture was diluted with EtOAc (30 mL) and washed with a saturated solution of sodium bicarbonate and brine. The organic extracts were dried over anhydrous MgSO₄. The solvents were removed under vacuum and residue was purified on silica gel (Biotage; eluting solvents hexanes:EtOAc 1/2 ratio) to afford tert-butyl ((1s, 3s)-3-(5-(4-methoxyphenyl)picolinamido)cyclobutyl)carbamate (125 mg, 78% yield) as white solid; 1H NMR (500 MHz, CDCl3) δ 8.73 (s, 1H), 8.21 (d, J=9 Hz, 1H), 8.12-8.08 (m, 1H), 7.99 (dd, J=8.5, 2.5 Hz, 1H), 7.57 (d, J=9 Hz, 2H), 7.04 (d, J=9 Hz, 2H), 4.78-4.70 (m, 1H), 4.31-4.25 (m, 1H), 3.96-3.89 (m, 1H), 3.88 (s, 1H), 2.95-2.86 (m, 2H), 2.04-1.93 (m, 2H), 1.45 (s, 9H)

Step c: N-((1s, 3s)-3-Aminocyclobutyl)-5-(4-methoxyphenyl)picolinamide TFA. This step was performed according to Method A.

Step d: N-((1s, 3s)-3-Isothiocyanatocyclobutyl)-5-(4-methoxyphenyl)picolinamide. This step was performed according to Method A.

¹H NMR (500 MHz, CDCl₃) δ 8.75 (t, J=1 Hz, 1H), 8.20 (d, J=8.5 Hz, 2H), 8.00 (dd, J=8.5, 2.5 Hz, 1H), 7.58 (dd, J=6.5, 2.5 Hz, 2H), 7.05 (dd, J=7, 2 Hz, 2H), 4.41-4.38 (m, 1H), 3.84-3.80 (m, 1H), 3.88 (s, 3H), 3.02-2.99 (m, 2H), 2.37-2.35 (m, 2H); MS (ESI) m/z 340.44 [M+1]⁺.

The following examples were prepared according to Method B.

Example 19. 5-(3-Fluoro-4-methoxyphenyl)-N-((1r, 3r)-3-isothiocyanatocyclobutyl) picolinamide

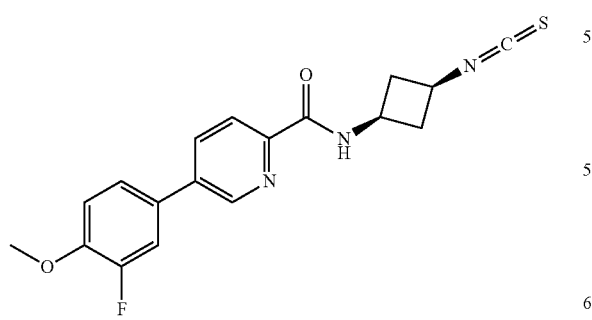

¹H NMR (500 MHz, CDCl₃) δ 8.72 (d, J=2 Hz, 1H), 8.21 (t, J 8, 10 Hz, 2H), 7.98 (dd, J=2.5, 8.5 Hz, 1H), 7.38 (m, 2H), 7.11 (t, J=8, 9.5 Hz, 1H), 4.42-4.36 (m, 1H), 3.96 (s, 3H), 3.94-3.91 (m, 2H), 2.39-2.33 (m, 2H); MS (ESI) m/z 358.44 [M+1]⁺.

Example 20. N-((1r, 3r)-3-Isothiocyanatocyclobutyl)-5-(3-methoxyphenyl)picolinamide

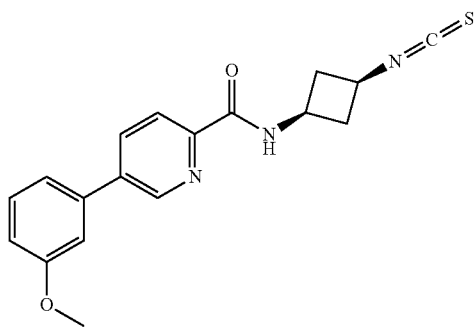 [SMILES: COc1cccc(-c2ccc(C(=O)N[C@H]3C[C@@H](N=C=S)C3)nc2)c1]

¹H NMR (500 MHz, CDCl₃) δ 8.77 (d, J=1 Hz, 1H), 8.23-8.21 (m, 2H), 8.03-8.01 (m, 2H), 7.45 (t, J=2.5 Hz, 1H), 7.20 (dd, J=6, 1 Hz, 1H), 7.13 (s, 1H), 7.01 (dd, J=8.5, 2.5 Hz, 1H), 4.82-4.70 (m, 1H), 3.95-3.80 (m, 1H), 3.89 (s, 3H), 3.02-2.99 (m, 2H), 2.38-2.35 (m, 2H); MS (ESI) m/z 340.46 [M+1]⁺.

Example 21. (1r, 3r)-3-Isothiocyanatocyclobutyl 5-(4-methoxyphenyl)picolinate

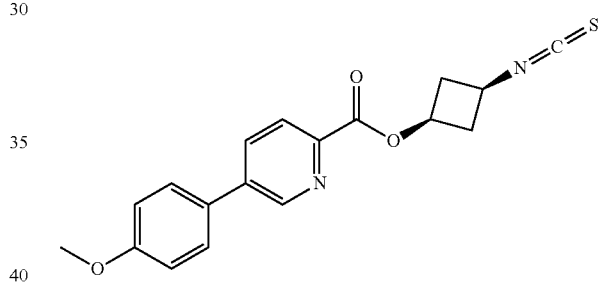

¹H NMR (500 MHz, CDCl₃) δ 8.73 (s, 1H), 8.18 (d, J=8 Hz, 2H), 7.98 (dd, J=8, 2 Hz, 1H), 7.56 (d, J=8.5 Hz, 2H), 7.03 (d, J=8.5 Hz, 2H), 4.40-4.36 (m, 1H), 3.93-3.88 (m, 1H), 3.86 (s, 3H), 3.02-2.96 (m, 2H), 2.38-2.32 (m, 2H); MS (ESI) m/z 340.37 [M+1]⁺.

Example 22. N-((1r, 3r)-3-Isothiocyanatocyclobutyl)-5-(4-methoxyphenyl)pyrazine-2-carboxamide

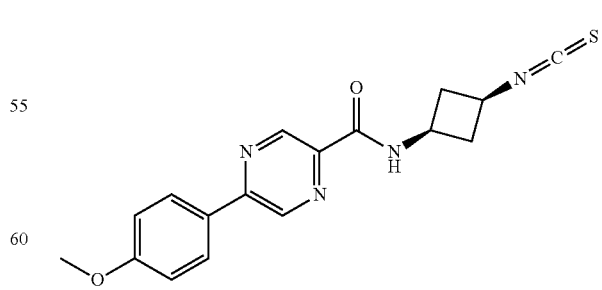

¹H NMR (500 MHz, CDCl₃) δ 9.32 (s, 1H), 8.88 (s, 1H), 8.07 (d, J=8.5 Hz, 2H), 7.92 (d, J=8 Hz, 1H), 7.05 (d, J=9 Hz, 2H), 4.41-4.37 (m, 1H), 3.94-3.88 (m, 4H), 3.03-2.98 (m, 2H), 2.37-2.31 (m, 2H).

Example 23. 5-(4-cyanophenyl)-N-((1r, 3r)-3-Isothiocyanatocyclobutyl)picolinamide

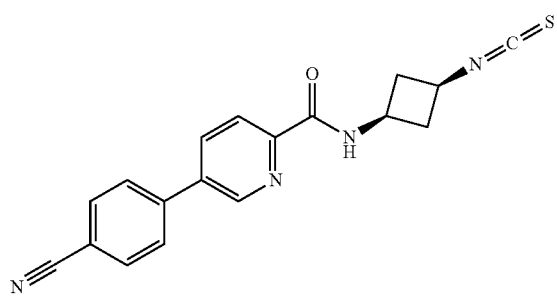 [SMILES: N#Cc1ccc(-c2ccc(C(=O)N[C@H]3C[C@@H](N=C=S)C3)nc2)cc1]

$^1$H NMR (500 MHz, CDCl$_3$) δ 8.77 (s, 1H), 8.27 (d, J=7.5 Hz, 1H), 8.05 (dd, J=8.5, 2.5 Hz, 1H), 7.81 (d, J=8.5 Hz, 2H), 7.72 (d, J=9 Hz, 2H), 4.42-4.34 (m, 1H), 3.94-3.90 (m, 1H), 3.03-2.98 (m, 2H), 2.38-2.32 (m, 2H).

Method C

Heterocyclic N-substituted N-((1s,3s)-3-isothiocyanatocyclobutyl)carboxamides (10) and 3-N-((1s,3s)-3-isothiocyanatocyclobutyl)carboxylates (11) were prepared according to scheme 3. Cyclobutyl-amine 1 or cyclobutyl-alcohol 2 were coupled with bromo-aryl carboxylic acids 3 to afford the corresponding amide 4 or ester 5, respectively. Palladium mediated cross-coupling reaction between aryl-bromides and the appropriate amine was used to generate the N-substituted analogs 6 and 7. Pd$_2$(dba)$_3$/2,2'-bis(diphenylphosphino)-1,1'-binaphthalene is the catalyst used in the process of the invention with polar and non-polar organic solvents, such as toluene and benzene. Deprotection of the BOC group of 6 and 7 afforded the free amines 8 and 9, respectively. Amines 8 and 9 were converted to N-((1s,3s)-3-isothiocyanatocyclobutyl) carboxamides (10) and 3-N-((1s,3s)-3-isothiocyanatocyclobutyl)carboxylates (11) as described in Method A.

Scheme 3

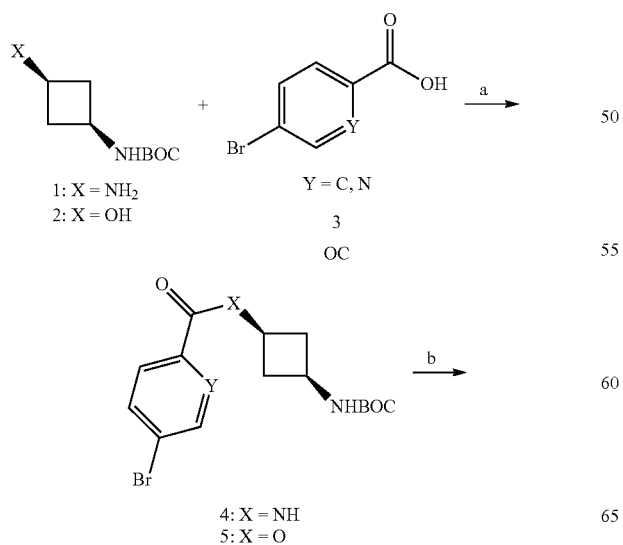

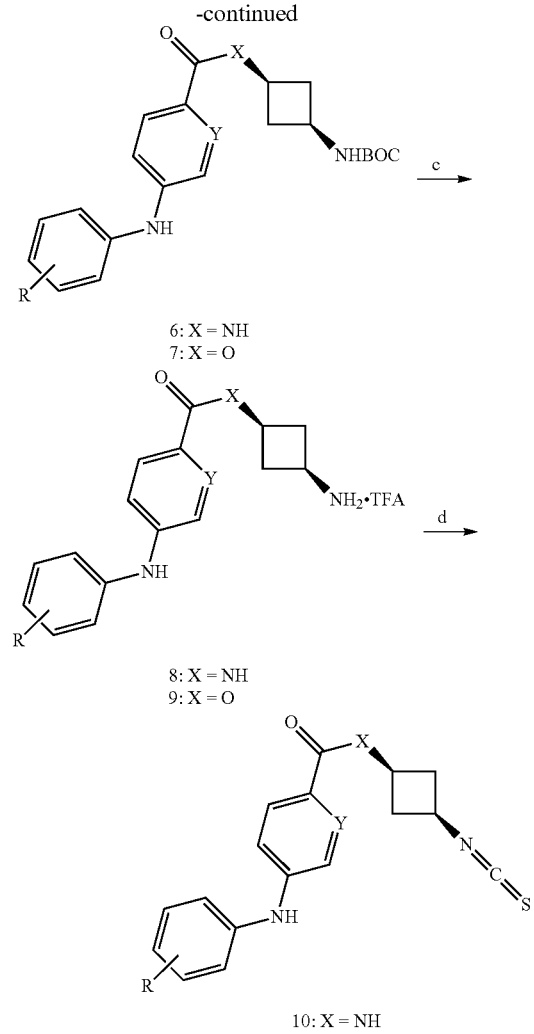

Reagents: (a) EDC, DIEA, HOBt, DMF; (b) aromatic amine, Pd$_2$(dba)$_3$, BINAP, sodium tert-butoxide, toluene, 80° C.; (c) TFA, CH$_2$Cl$_2$; (d) 1,1'-thiocarbonyldi-2(1H)-pyridone, Et$_3$N, CH$_2$Cl$_2$

Example 24. N-((1r, 3r)-3-Isothiocyanatocyclobutyl)-5-((4-methoxyphenyl)amino) picolinamide

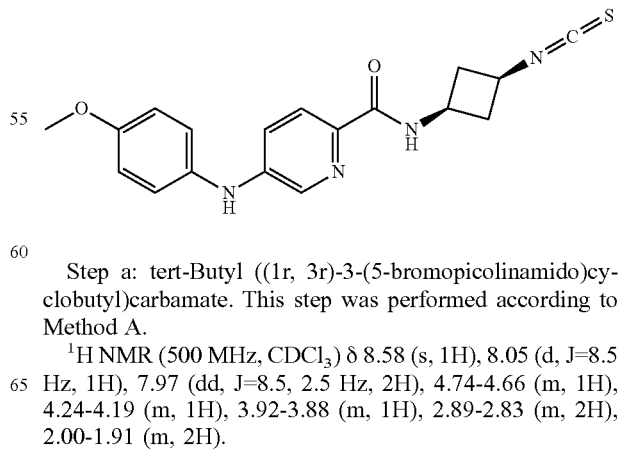

Step a: tert-Butyl ((1r, 3r)-3-(5-bromopicolinamido)cyclobutyl)carbamate. This step was performed according to Method A.

$^1$H NMR (500 MHz, CDCl$_3$) δ 8.58 (s, 1H), 8.05 (d, J=8.5 Hz, 1H), 7.97 (dd, J=8.5, 2.5 Hz, 2H), 4.74-4.66 (m, 1H), 4.24-4.19 (m, 1H), 3.92-3.88 (m, 1H), 2.89-2.83 (m, 2H), 2.00-1.91 (m, 2H).

Step b: tert-Butyl ((1r, 3r)-3-(5-((4-methoxyphenyl)amino)picolinamido)cyclobutyl) carbamate. Tris(dibenzylideneacetone)dipalladium(0) (6.88 mg, 0.01 mmol), 2,2'-bis(diphenylphosphino)-1,1'-binaphthalene (14 mg, 0.02 mmol) and sodium tert-butoxide (101 mg, 1.05 mmol) were added into a solution of tert-butyl ((1s, 3s)-3-(5-bromopicolinamido)cyclobutyl)carbamate (278 mg, 0.75 mmol) in toluene (2 mL). The reaction mixture was purged with argon for 5 minutes and then p-anisidine (111 mg, 0.90 mmol) was added and the mixture was stirred at 80° C. for 3 hours. After the completion of the reaction (monitored by TLC) the solvent was removed under vacuum and water (15 mL) was added and the mixture was extracted with EtOAc (2×15 mL). The combined organic extracts were dried over MgSO$_4$. The solvents were removed under vacuum and the residue was purified on silica gel (Biotage; eluting solvents hexanes:EtOAc 3/1 ratio) to afford tert-butyl ((1r,3r)-3-(5-((4-methoxyphenyl)amino)picolinamido)cyclobutyl)carbamate as yellow solid (160 mg, 52% yield).

$^1$H NMR (500 MHz, CDCl$_3$) δ 8.07 (d, J=2.5 Hz, 1H), 7.97 (d, J=8.5 Hz, 1H), 7.85-7.82 (m, 1H), 7.21 (dd, J=9, 3 Hz, 1H), 7.13 (d, J=9 Hz, 2H), 6.93 (d, J=9 Hz, 2H), 5.81 (s, 1H), 4.73-4.69 (m, 1H), 4.27-4.18 (m, 1H), 3.95-3.86 (m, 1H), 3.83 (s, 3H), 2.90-2.83 (m, 2H), 1.96-1.88 (m, 2H), 1.45 (s, 9H).

Step c: N-((1r, 3r)-3-Aminocyclobutyl)-5-((4-methoxyphenyl)amino)picolinamide TFA salt. This step was performed according to Method A.

Step d: N-((1r, 3r)-3-Isothiocyanatocyclobutyl)-5-((4-methoxyphenyl)amino)picolinamide. This step was performed according to Method A.

$^1$H NMR (500 MHz, CDCl$_3$) δ 8.75 (d, J=2.5 Hz, 1H), 7.96-7.92 (m, 2H), 7.20 (dd, J=9, 3 Hz, 1H), 7.14 (dd, J=6.5, 1.5 Hz, 2H), 6.93 (dd, J=6.5, 2.5 Hz, 2H), 5.82 (s, 1H), 4.40-4.32 (m, 1H), 3.91-3.86 (m, 1H), 3.83 (s, 3H), 2.98-2.96 (m, 2H), 2.32-2.30 (m, 2H); MS (ESI) m/z 355.48 [M+1]$^+$.

Method D

N-((1s,3s)-3-isothiocyanatocyclobutyl)sulfonamides 6 were prepared according to scheme 4. Cyclobutyl-amine 1 was coupled with bromo-aryl sulfonyl chloride 2 to afford the corresponding sulfonamides 3. Palladium cross-coupling was performed as described in method B to form the bi-aryl moieties 4. Deprotection of the BOC group of 4 afforded free amine 5. Amine 5 was converted to N-((1s,3s)-3-isothiocyanatocyclobutyl)sulfonamide 6 as described in Method A.

Scheme 4

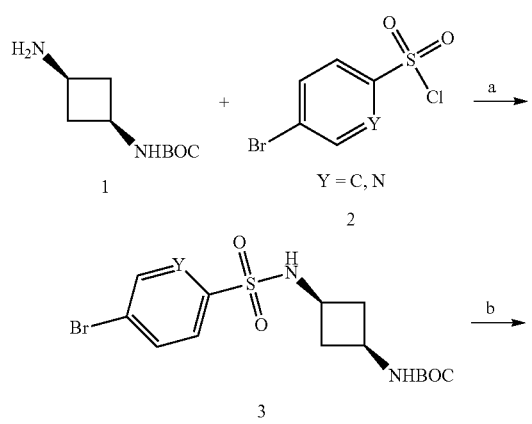

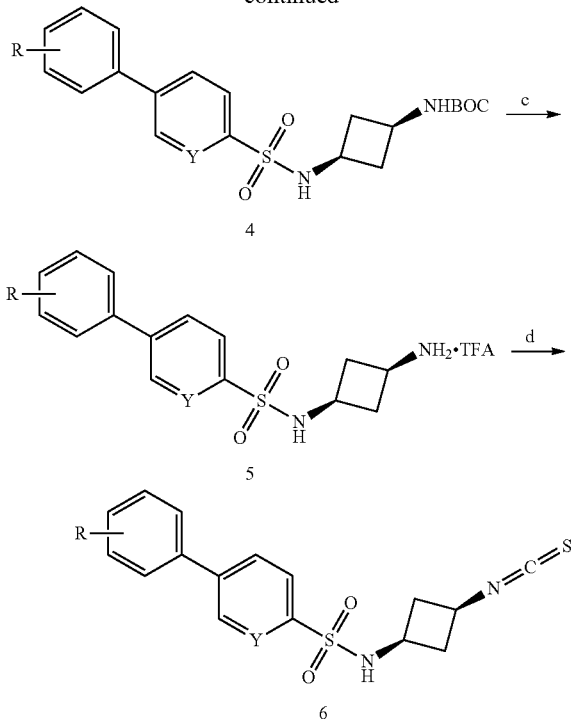

Reagents: (a) DIEA, CH$_2$Cl$_2$; (b) Aromatic-amine, Pd$_2$(dba)$_3$, BINAP, sodium tert-butoxide, toluene, 80° C.; (c) TFA, CH$_2$Cl$_2$; (d) 1,1'-thiocarbonyldi-2(1H)-pyridone, Et$_3$N, CH$_2$Cl$_2$ Example 25. N-((1r, 3r)-3-Isothiocyanatocyclobutyl)-4'-methoxy-[1,1'-biphenyl]-4-sulfonamide

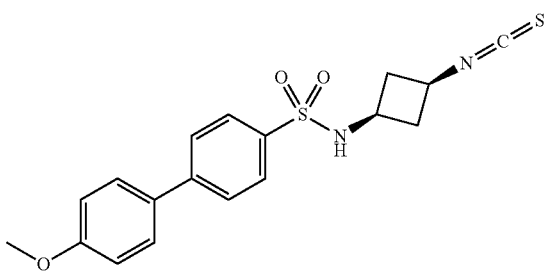 [SMILES: COc1ccc(-c2ccc(S(=O)(=O)N[C@H]3C[C@@H](N=C=S)C3)cc2)cc1]

Step a: tert-Butyl ((1r, 3r)-3-((4-bromophenyl)sulfonamido)cyclobutyl)carbamate. tert-Butyl (cis-3-aminocyclobutyl)carbamate (150 mg, 0.81 mmol), and diisopropylethylamine (0.23 mL, 1.34 mmol) were added to a stirring solution of 4-bromobenzene-sulfonyl chloride (172 mg, 0.67 mmol) in dichloromethane (5 mL). The resulting reaction mixture was stirred for 18 hours at room temperature, and then diluted with EtOAc and washed with water and saturated solution of ammonium chloride. The organic layer was dried over MgSO$_4$ and the solvent was removed under reduced pressure to afford tert-butyl ((1r,3r)-3-((4-bromophenyl)sulfonamido) cyclobutyl)carbamate (233 mg, 86% yield) as white solid.

$^1$H NMR (500 MHz, DMSO-d$_6$) δ 8.02-8.05 (m, 1H), 7.82 (d, J=9 Hz, 2H), 7.71 (d, J=9 Hz, 2H), 7.08-7.06 (m, 1H), 3.49-3.44 (m, 1H), 3.28-3.21 (m, 1H), 2.25-2.18 (m, 2H), 1.68-1.61 (m, 2H), 1.33 (s, 9H).

Step b: tert-Butyl ((1r, 3r)-3-((4'-methoxy-[1,1'-biphenyl])-4-sulfonamido)cyclobutyl) carbamate. This step was performed according to Method B.

¹H NMR (500 MHz, d₆-DMSO) δ 7.93 (d, J=7.5 Hz, 1H), 7.84 (q, J=9, 7.5 Hz, 4H), 7.72 (d, J=8.5 Hz, 2H), 7.07-7.05 (m, 3H), 4.05-4.01 (m, 1H), 3.82 (s, 3H), 3.50-3.43 (m, 1H), 2.26-2.22 (m, 2H), 1.71-1.62 (m, 2H), 1.32 (s, 9H).

Step c: N-((1r, 3r)-3-Aminocyclobutyl)-4'-methoxy-[1,1'-biphenyl]-4-sulfonamide TFA salt. This step was performed according to Method A.

Step d: N-((1r, 3r)-3-Isothiocyanatocyclobutyl)-4'-methoxy-[1,1'-biphenyl]-4-sulfonamide. This step was performed according to Method A.

¹H NMR (500 MHz, d₆-DMSO) δ 8.10 (d, J=10 Hz, 1H), 7.86 (dd, J=25, 9 Hz, 4H), 7.72 (d, J=9.5 Hz, 2H), 7.08 (d, J=9 Hz, 2H), 3.94-3.86 (m, 1H), 3.82 (s, 3H), 3.51-3.42 (m, 1H), 2.56-2.49 (m, 2H), 2.04-1.97 (m, 2H); MS (ESI) m/z 375.49 [M+1]⁺.

The following examples were prepared according to Method D.

Example 26. N-((1s, 3s)-3-Isothiocyanatocyclobutyl)-5-(4-methoxyphenyl)pyridine-2-sulfonamide ¹H NMR (500 MHz, d₆-DMSO) δ 9.03 (s, 1H), 8.34 (m, 3H), 7.95 (d, J=8 Hz, 1H), 7.81 (d, J=9 Hz, 2H), 7.12 (d, J=9 Hz, 2H), 3.95-3.88 (m, 1H), 3.83 (s, 3H), 3.61-3.54 (m, 1H), 2.57-2.54 (m, 2H), 2.10-2.08 (m, 2H); MS (ESI) m/z 376.41 [M+1]⁺.

Method E

N-((1s,3s)-3-isothiocyanatocyclobutyl)sulfonates 6 were prepared according to scheme 5. Cyclobutyl-amine 1 was coupled with bromo-aryl sulfonyl chloride 2 to afford the corresponding sulfonate 3. Palladium cross-coupling reaction was performed as described in method B to afford the bi-aryl sulfonate 4. Deprotection of the BOC group of 4 afforded the free amine 5. Amine 5 was converted to N-((1s,3s)-3-isothiocyanatocyclobutyl)sulfonate 6 as described in Method A.

Scheme 5

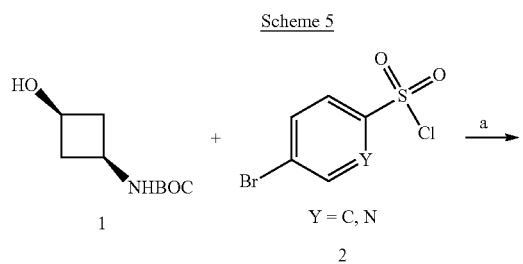

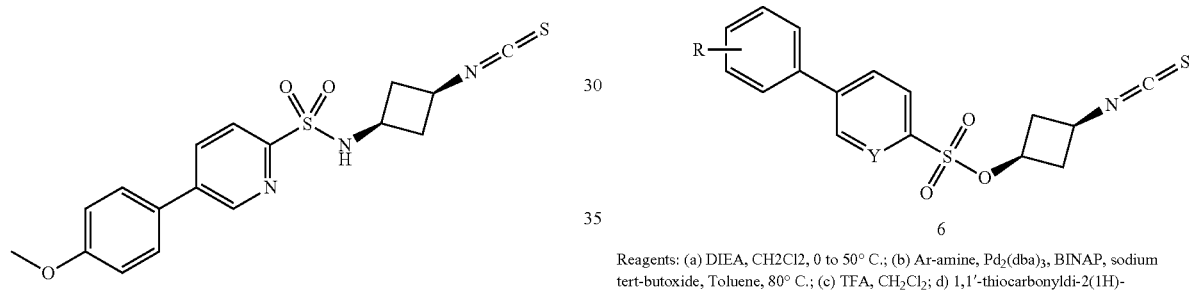

Reagents: (a) DIEA, CH2Cl2, 0 to 50° C.; (b) Ar-amine, Pd₂(dba)₃, BINAP, sodium tert-butoxide, Toluene, 80° C.; (c) TFA, CH₂Cl₂; d) 1,1'-thiocarbonyldi-2(1H)-pyridone, Et₃N, CH₂Cl₂

Example 27. (1s, 3 s)-3-Isothiocyanatocyclobutyl 4'-methoxy-[1,1'-biphenyl]-4-sulfonate Step a: (1s, 3s)-3-((tert-Butoxycarbonyl)amino)cyclobutyl 4-bromobenzenesulfonate. tert-Butyl (cis-3-hydroxycyclobutyl)carbamate (210 mg, 0.82 mmol), and diisopropylethylamine (1 mL, 5.75 mmol) were added into a stirring solution of 4-bromobenzene-sulfonyl chloride (308 mg, 1.64 mmol) in dichloromethane (5 mL) at 0° C. and under argon. The resulting reaction mixture was refluxed at 50° C. for 24 hours. The reaction mixture was diluted with Et₂O and washed with water and brine. The organic layer was left to crystallize overnight at −20° C. and then filtered and washed with hexanes to afford (1s, 3s)-3-((tert-butoxycarbonyl) amino) cyclobutyl 4-bromobenzenesulfonate (186 mg, 56% yield) as white solid.

¹H NMR (500 MHz, d₆-DMSO) δ 7.91 (d, J=8.5 Hz, 2H), 7.82 (d, J=8.5 Hz, 2H), 7.147 (d, J=8.5 Hz, 1H), 4.59-4.53 (m, 1H), 3.59-3.3.51 (m, 1H), 2.48-2.43 (m, 2H), 2.02-1.96 (m, 2H), 1.34 (s, 9H).

Step b: (1s, 3s)-3-((tert-Butoxycarbonyl)amino)cyclobutyl 4'-methoxy-[1,1'-biphenyl]-4-sulfonate. This step was performed according to Method B.

¹H NMR (500 MHz, CDCl₃) δ 7.92 (d, J=8 Hz, 2H), 7.72 (d, J=8.5 Hz, 2H), 7.57 (d, J=8.5 Hz, 2H), 7.03 (d, J=8.5 Hz, 2H), 4.58-4.50 (m, 1H), 3.87 (s, 3H), 3.76-3.70 (m, 1H), 2.79-2.71 (m, 2H), 2.08-2.00 (m, 2H).

Step c: (1s, 3s)-3-Aminocyclobutyl 4'-methoxy-[1, 1'-biphenyl]-4-sulfonate. This step was performed according to Method A.

Step d: (1s, 3s)-3-Isothiocyanatocyclobutyl 4'-methoxy-[1, 1'-biphenyl]-4-sulfonate. This step was performed according to Method A.

¹H NMR (500 MHz, CDCl₃) δ 7.93 (d, J=9 Hz, 2H), 7.73 (d, J=8.5 Hz, 2H), 7.58 (d, J=8.5 Hz, 2H), 7.03 (d, J=9 Hz, 2H), 4.62-4.57 (m, 1H), 3.88 (s, 3H), 3.76-3.50 (m, 1H), 2.86-2.83 (m, 2H), 2.50-2.47 (m, 2H).

Example 28. (1s,3s)-3-isothiocyanatocyclobutyl 3,3'-difluoro-4'-methoxy-[1,1'-biphenyl]-4-carboxylate

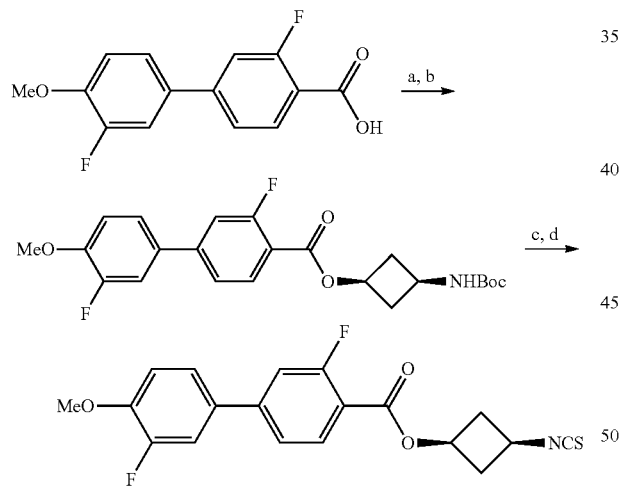

Scheme 6

Reagents: (a) (COCl)₂, DCM; (b) tert-butyl ((1s,3s)-3-hydroxycyclobutyl)carbamate, Et₃N, DCM; (c) 4M HCl in dioxane; (d) Thiocarbonyl pyridin-2-one, Et₃N, CH₂Cl₂

To a solution of (1s,3s)-3-aminocyclobutyl 4-bromo-2-fluorobenzoate hydrochloride (20.0 mg, 0.054 mmol) in 1 mL anhydrous dichloromethane, triethylamine (10.9 mg, 15.1 mmol) was added with stirring at room temperature. 1,1'-thiocarbonyl pyridin-2-one (13.8 mg, 0.059 mmol) was added to reaction mixture and reaction continue for 2 h (control by TLC for disappearing of amine). After the solvent was removed by vacuum the crude product was subject to chromatography to afford (1s,3s)-3-isothiocyanatocyclobutyl 3,3'-difluoro-4'-methoxy-[1,1'-biphenyl]-4-carboxylate (19.8 mg, 97.7% yield). ¹H NMR (400 MHz, CDCl₃) δ ppm 2.47-2.63 (m, 2H), 2.98-3.15 (m, 2H), 3.91 (quintet, J=7.30 Hz, 1H), 4.99 (quin, J=7.30 Hz, 1H), 7.05 (t, J=8.79 Hz, 2H), 7.28-7.45 (m, 4H), 7.98 (t, J=8.06 Hz, 2H).

Example 29. 3,3'-Difluoro-N-((1s,3s)-3-isothiocyanatocyclobutyl)-4'-methoxy-[1,1'-biphenyl]-4-carboxamide

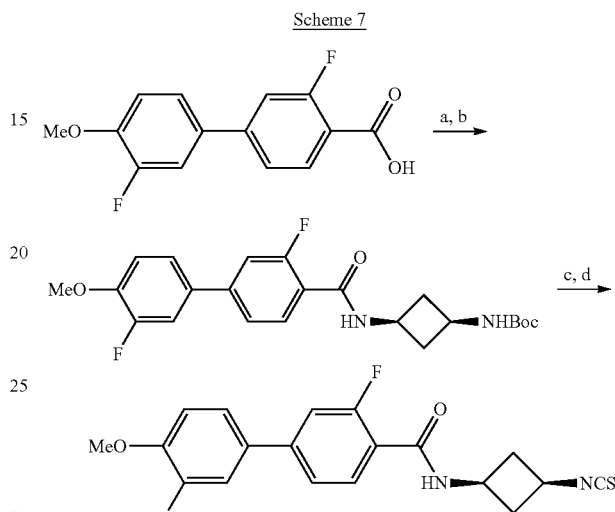

Scheme 7

Reagents: (a) (COCl)₂, CH₂Cl₂; (b). tert-butyl ((1s,3s)-3-hydroxycyclobutyl)carbamate, Et₃N, CH₂Cl₂; (c) 4M HC in dioxane; (d) thiocarbonyl pyridin-2-one, Et₃N, CH₂Cl₂;

This compound was prepared according to Example 1.

¹H NMR (400 MHz, CDCl₃) δ ppm 2.29 (dd, J=8.79, 2.93 Hz, 2H), 3.02 (dd, J=9.53, 2.20 Hz, 2H), 3.88-3.99 (m, 3H), 4.33-4.45 (m, 1H), 7.06 (dd, J=9.53, 8.06 Hz, 1H), 7.27-7.29 (m, 2H), 7.31-7.38 (m, 3H), 7.44 (dd, J=8.06, 1.47 Hz, 1H), 8.11 (t, J=9.53 Hz, 1H).

Example 30. 3'-Fluoro-N-((1s,3s)-3-isothiocyanatocyclobutyl)-4'-methoxy-[1,1'-biphenyl]-4-sulfonamide

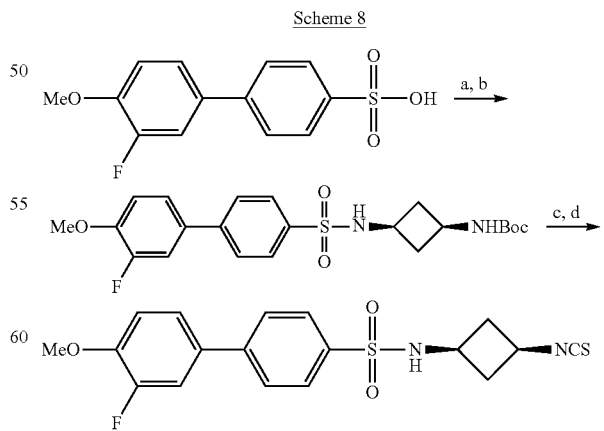

Scheme 8

Reagents: (a) (COCl)₂, CH₂Cl₂; (b) tert-butyl ((1s,3s)-3-aminocyclobutyl)carbamate, Et₃N, CH₂Cl₂; c. 4M HCl in dioxane; (d) thiocarbonyl pyridin-2-one, Et₃N, CH₂Cl₂

This compound was prepared according to Example 1.

$^1$H NMR (500 MHz, CDCl$_3$) δ ppm 2.03-2.12 (m, 2H), 2.70-2.79 (m, 2H), 3.56-3.67 (m, 1H), 3.70-3.79 (m, 1H), 4.66-4.71 (m, 1H), 7.07 (s, 1H), 7.33-7.39 (m, 2H), 7.67 (d, J=8.30 Hz, 2H), 7.88 (d, J=8.30 Hz, 2H).

Example 31. (1s,3s)-3-Isothiocyanatocyclobutyl 3'-fluoro-4'-methoxy-[1,1'-biphenyl]-4-sulfonate Scheme 9

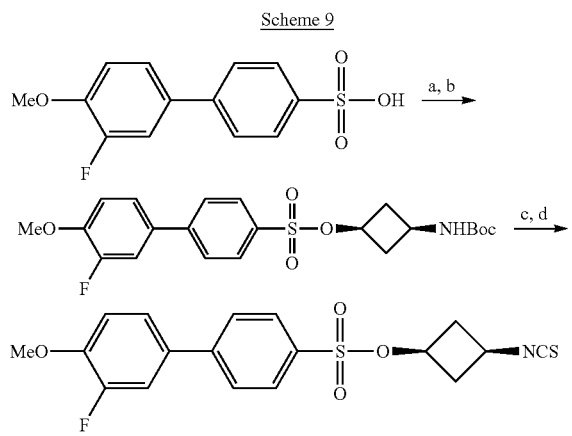

Reagents: (a) (COCl)$_2$, CH$_2$Cl$_2$; (b) tert-butyl ((1s,3s)-3-hydroxycyclobutyl)carbamate, Et$_3$N, CH$_2$Cl$_2$; (c) 4M HCl in dioxane; (d) thiocarbonyl pyridin-2-one, Et$_3$N, CH$_2$Cl$_2$ This compound was prepared according to Example 1.

$^1$H NMR (500 MHz, CDCl$_3$) δ ppm 2.41-2.55 (m, 2H), 2.79-2.91 (m, 2H), 3.74 (quintet, J=7.80 Hz, 1H), 4.60 (quintet, J=7.30 Hz, 1H), 7.07 (t, J=8.30 Hz, 1H), 7.30-7.45 (m, 2H), 7.70 (d, J=8.30 Hz, 2H), 7.93 (d, J=8.30 Hz, 2H).

Example 32. N-(1s,3s)-(3-Isothiocyanatocyclobutyl)-6-phenylhexanamide

Scheme 10

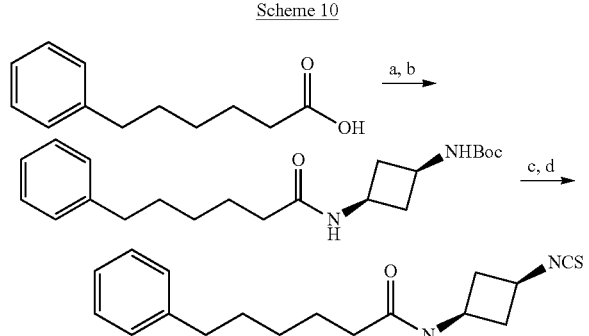

Reagents: (a) (COCl)$_2$, CH$_2$Cl$_2$ (b) tert-butyl ((1s,3s)-3-aminocyclobutyl)carbamate, Et$_3$N, CH$_2$Cl$_2$ (c) 4M HCl in dioxane; (d) thiocarbonyl pyridin-2-one, Et$_3$N, CH$_2$Cl$_2$ This compound was prepared according to Example 1.

$^1$H NMR (400 MHz, CDCl$_3$) δ ppm 1.35 (quintet, J=8.10 Hz, 2H), 1.60-1.70 (m, 5H), 2.03-2.16 (m, 4H), 2.61 (t, J=7.69 Hz, 2H), 2.61-2.61 (m, 1H), 2.84-2.94 (m, 2H), 3.82 (quintet, J=8.10 Hz, 1H), 4.17 (sextet, J=8.10 Hz, 1H), 5.45-5.55 (m, 1H), 7.14-7.22 (m, 2H), 7.27-7.31 (m, 1H).

Example 33. 4'-Methoxy-[1,1'-biphenyl]-4-yl ((1s,3s)-3-isothiocyanatocyclobutyl)carbamate

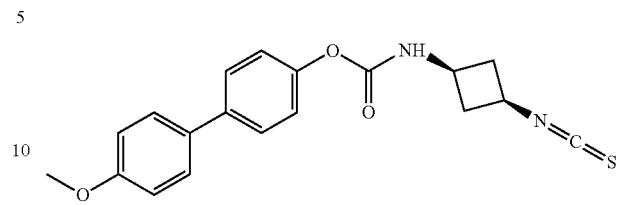

$^1$H NMR (400 MHz, CDCl$_3$) δ 7.50 (dd, J=13.5, 8.7 Hz, 4H), 7.15 (d, J=8.6 Hz, 2H), 6.96 (d, J=8.8 Hz, 2H), 5.21 (d, J=8 Hz, 1H), 4.03-4.01 (m, 1H), 3.85 (s, 3H), 3.84-3.83 (m, 1H), 2.99-2.92 (m, 2H), 2.29-2.26 (m, 2H).

Example 34. N-(cis-(3-Isothiocyanatocyclobutyl))-5-methoxy-[2,3'-bipyridine]-6'-carboxamide

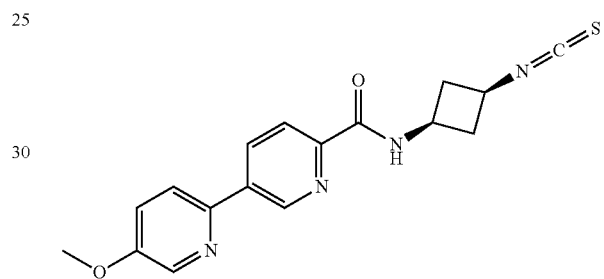

Scheme 1

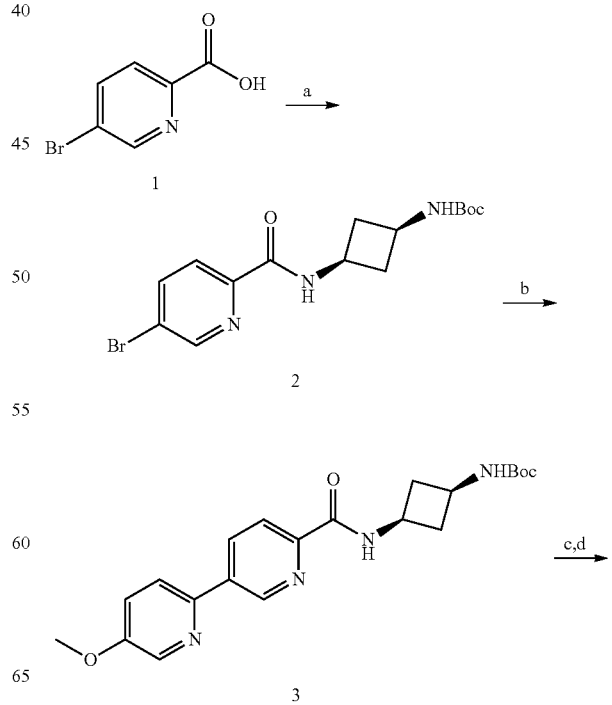

-continued

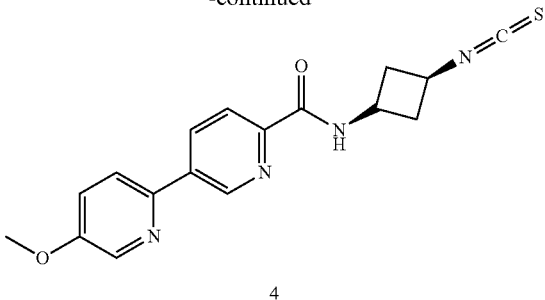

4

Reagents and Conditions: (a) tert-Butyl ((1r,3r)-3-aminocyclobutyl)carbamate, EDAC/HOBt, EtN(i-Pr)2, DMF, CH2Cl2, rt, 12 h; (b) (5-methoxypyridin-2-yl)boronic acid, Pd[(PPh3)]2Cl2, K2CO3, MeOH/Dioxane/H2O, 80° C., 4 h.; (c) HCl/dioxane; (d) 1,1'-thiocarbonyldi 2-[1H]-pyridone, EtN(i-Pr)2, CH2Cl2, rt, 2 h Step a): tert-Butyl (cis-3-(5-bromopicolinamido)cyclobutyl)carbamate. To a stirring suspension of 5-bromopicolinic acid (404 mg, 2.0 mmol) and N-ethyl-N-diisopropyl amine (750 mg, 6.0 mmol) in anhydrous dichloromethane (20 mL) at room temperature under argon was added DMF (0.5 mL), EDAC-HCl (480 mg, 2.5 mmol), and HOBt (338 mg, 2.5 mmol), sequentially. The resulting mixture was stirred at room temperature for 12 hours, diluted with methylene chloride (20 mL) and saturated aqueous NaHCO₃ (10 mL). The aqueous layer was further extracted with methylene chloride (2×10 mL). The combined organic layers were dried (MgSO₄) and the solvent evaporated under reduced pressure to give a crude material, which was purified by column chromatography (ethyl acetate/hexane, 1:1) to give title compound tert-butyl (cis-3-(5-bromopicolinamido)cyclobutyl)carbamate (562.0 mg, 76% yield). ¹H NMR (400 MHz, CDCl₃): δ 8.58 (d, J=2.0 Hz, 1H); 8.05 (dd, J=8.0 Hz J=2.0 Hz, 1H); 7.96 (d, J=8.0 Hz, 1H); 7.95 (brs, 1H); 4.71 (brs, 1H), 4.27-4.17 (m, 1H); 3.89-3.80 (m, 1H); 2.88-2.84 (m, 2H); 1.87-1.80 (m, 2H); 1.43 (s, 9H).

Step b): tert-Butyl (cis-3-(5-bromopicolinamido)cyclobutyl)carbamate. To a solution of tert-butyl (cis-3-(5-bromopicolinamido)cyclobutyl)carbamate (259 mg, 0.7 mmol) in dioxane/methanol (2:1, 9.0 mL) was added 5-methoxypyridine-2-boronic acid (138 mg, 0.9 mmol) and a solution of K₂CO₃ (248 mg, 1.8 mmol) in water (5 mL). The mixture bubbled with argon with stirring (10 min) and Pd[(PPh₃)]₂Cl₂ (28.0 mg 0.04 mmol) was added and the mixture heated at 80° C. for 4 hours. The mixture was then cooled to room temperature, diluted with methylene chloride (20.0 mL) and water (5 mL). The aqueous layer was further extracted with methylene chloride/methanol (4:1, 20 mL). The combined organic layers was dried (MgSO₄) and the solvent evaporated under reduced pressure to give a crude material, purified by column chromatography (ethyl acetate/hexane, 1:1) to give title compound tert-butyl (cis-3-(5-bromopicolinamido)cyclobutyl)carbamate (112.0 mg, 40% yield). ¹H NMR (400 MHz, CDCl₃): δ 9.09 (d, J=2.0, 1H); 8.44 (d, J=2.0 Hz, 1H); 8.35 (d, J=8.0 Hz, 1H); 8.22 (d, J=8.0 Hz, 1H); 7.74 (d, J=8.0 Hz, 1H); 7.28 (d, J=8.0 Hz, 1H); 7.16 (brs, 1H); 4.45-4.43 (m, 1H); 3.93 (s, 3H); 3.88-3.85 (m, 1H); 2.96-2.89 (m, 2H); 2.09-1.80 (m, 2H); 1.44 (s, 9H).

Step c): N-((1s,3s)-3-aminocyclobutyl)-5-methoxy-[2,3'-bipyridine]-6'-carboxamide HCl salt. A solution of tert-butyl (cis-3-(5-bromopicolinamido)cyclobutyl)carbamate (100 mg, 0.25 mmol) was treated with HCl in dioxane (4 N, 0.5 mL). The mixture was stirred at room temperature for 6 hours. The solvent was removed in vacuum. The crude hydrochloride salt triturated with diethyl ether (2 mL) and isolated by filtration to give N-((1s,3s)-3-aminocyclobutyl)-5-methoxy-[2,3'-bipyridine]-6'-carboxamide HCl salt 110 mg of material, used in the next step without further purification.

Step d). N-(cis-(3-Isothiocyanatocyclobutyl))-5-methoxy-[2,3'-bipyridine]-6'-carboxamide. To a suspension of N-((1s,3s)-3-aminocyclobutyl)-5-methoxy-[2,3'-bipyridine]-6'-carboxamide HCl salt in dichloromethane (10 mL) was added EtN(i-Pr)₂ (129.0 mg, 1.0 mmol). The mixture was stirred 10 minutes, and 1,1'-thiocarbonyldi 2-[1H]-pyridone was added. The mixture was stirred at room temperature (2 hours) and the solvent evaporated under reduced pressure. The crude material was purified by column chromatography to provide 45 mg of N-(cis-(3-Isothiocyanatocyclobutyl))-5-methoxy-[2,3'-bipyridine]-6'-carboxamide (53% yield). ¹H NMR (400 MHz, CDCl₃): δ 9.10 (d, J=2.0, 1H); 8.44 (d, J=2.0 Hz, 1H); 8.38 (dd, J=8.0, dd, J=2.0 Hz, 1H); 8.21 (d, J=8.0 Hz, 1H); 8.15 (brs, 1H); 7.73 (d, J=8.0 Hz, 1H); 7.3 (d, J=8.0 Hz, 1H); 4.73 (brs, 1H), 4.28-4.20 (m, 1H); 3.89 (s, 3H); 3.88-3.85 (m, 1H); 2.96-2.89 (m, 2H); 2.09-1.80 (m, 2H).

Example 35. N-((cis)-3-isothiocyanatocyclobutyl)-2-(4-methoxyphenyl)oxazole-5-carboxamide

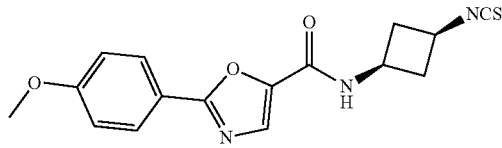

Scheme 2

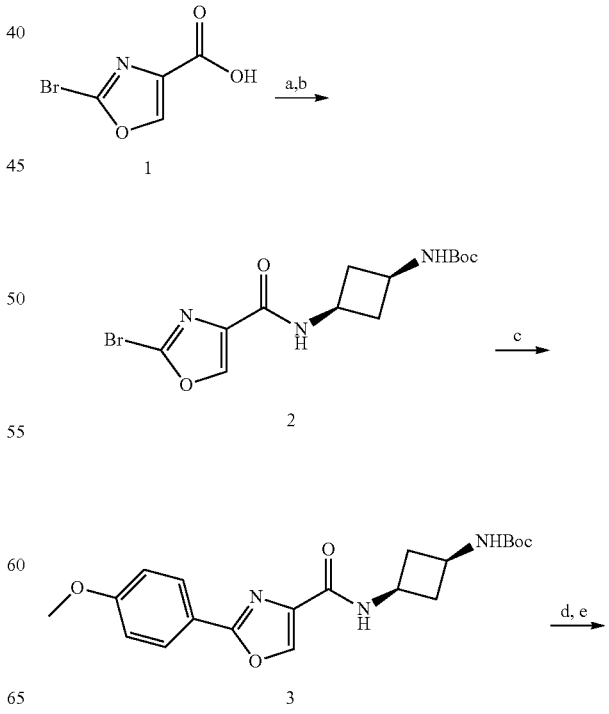

-continued

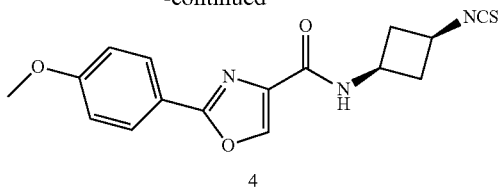

4

Reagents and Conditions: (a) (COCl)₂, cat. DMF, CH₂Cl₂, rt, 2 h; (b) 2, EtN(i-Pr)₂, CH₂Cl₂, rt, 2 h; (c) (4-methoxyphenyl)boronic acid, Pd(OAc)₂/DPPF, K₂CO₃, dioxane/H₂O, 80° C., 4 h.; (d) HCl/dioxane; (e) 1,1'-thiocarbonyldi 2-[1H]-pyridone, EtN(i-Pr)₂, CH₂Cl₂, rt, 2 h Step a): 2-Bromooxazole-4-carbonyl chloride. To a stirring suspension of 2-bromooxazole-4-carboxylic acid (96.0 mg, 0.5 mmol) in anhydrous dichloromethane (5.0 mL) at room temperature, under argon was added DMF (0.01 mL), and oxalyl chloride (149 mg, 0.1 mL, 1.2 mmol). The resulting mixture was stirred at room temperature for 2 hours. The solvent was evaporated under reduced pressure to give 2-bromooxazole-4-carbonyl chloride as a crude material which was used without purification.

Step b): tert-Butyl ((cis)-3-(2-bromooxazole-4-carboxamido)cyclobutyl)carbamate. A solution of 2-bromooxazole-4-carbonyl chloride (step a) in anhydrous dichloromethane (5.0 mL) was added dropwise to a mixture of cis-(3-aminocyclobutyl)carbamate (112.0 mg, 0.6 mmol) and EtN(i-Pr)₂ (155.0 mg, 1.2 mmol) in dichloromethane (5 mL) at room temperature under argon. The mixture was stirred (2 hours) and diluted with saturated aqueous NaHCO₃ (5 mL). The aqueous layer was extracted with CH₂Cl₂/MeOH (4:1 2×10 mL). The combined organic layers were dried (MgSO₄) and the solvent evaporated under reduced pressure to give a crude material which was purified by column chromatography (MeOH/CH₂Cl₂ (1:24) to tert-butyl ((cis)-3-(2-bromooxazole-4-carboxamido)cyclobutyl) carbamate (134 mg, 75% yield). ¹H NMR (400 MHz, CDCl₃): δ 8.12 (s, 1H); 6.90 (brs, 1H); 4.70 (brs, 1H); 4.03-4.01 (m, 1H); 3.99-3.82 (m, 1H); 2.92-2.75 (m, 2H); 1.98-1.84 (m, 2H); 1.44 (s, 9H).

Step c). tert-butyl ((cis)-3-2-(4-methoxyphenyl)oxazole-4carboxamido)cyclobutyl)carbamate. To a solution of tert-butyl ((cis)-3-(2-bromooxazole-4-carboxamido)cyclobutyl) carbamate (72.0 mg, 0.2 mmol) in dioxane (4 mL) was added 4-methoxphenylboronic acid (46.0 mg, 0.3 mmol) and a solution of K₂CO₃ (83.0 mg, 0.6 mmol) in water (2 mL), DPPF (22.0 mg, 0.04 mmol) was added and the mixture bubbled with argon with stirring (10 minutes). The mixture was treated with Pd(OAc)₂ (4.5 mg 0.02 mmol) and heated at 80° C. for 4 hours. The mixture was cooled to room temperature, diluted with methylene chloride (10.0 mL) and water (3 mL). The aqueous layer was further extracted with methylene chloride/methanol (4:1, 10 mL). The combined organic layers was dried (MgSO₄) and the solvent evaporated under reduced pressure to give a crude material, which was purified by column chromatography (35% EtOAc/5% MeOH/40% Hexane) to afford title compound tert-butyl ((cis)-3-2-(4-methoxyphenyl)oxazole-4carboxamido)cyclobutyl) carbamate (43.0 mg, 56% yield). ¹H NMR (400 MHz, CDCl₃): δ 8.17 (s, 1H); 7.98 (d, J=8.0 Hz, 2H); 7.12 (d, J=8.0 Hz, 1H); 6.90 (d, J=8.0 Hz, 2H); 4.72 (brs, 1H); 4.30-4.20 (m, 1H); 3.99-3.82 (m, 1H); 3.88 (s, 3H); 2.92-2.82 (m, 2H); 2.05-1.94 (m, 2H); 1.45 (s, 9H).

Step d): N-((cis)-3-isothiocyanatocyclobutyl)-2-(4-methoxyphenyl)oxazole-5-carboxamide. A similar procedure to that described for the synthesis of N-(cis-(3-isothiocyanatocyclobutyl))-5-methoxy-[2,3'-bipyridine]-6'-carboxamide step c) and step d) was followed by using tert-butyl ((cis)-3-2-(4-methoxyphenyl)oxazole-4carboxamido)cyclobutyl) carbamate (39.0 mg, 0.1 mmol) to obtain N-((cis)-3-isothiocyanatocyclobutyl)-2-(4-methoxyphenyl) oxazole-5-carboxamide (20.0 mg, 61%). ¹H NMR (400 MHz, CDCl₃): δ 8.17 (s, 1H); 7.98 (d, J=8.0 Hz, 2H); 7.12 (d, J=8.0 Hz, 1H); 6.90 (d, J=9.0 Hz, 2H); 4.50-4.32 (m, 1H); 3.99-3.82 (m, 1H); 3.88 (s, 3H); 3.05-2.92 (m, 2H); 2.40-2.24 (m, 2H).

Example 36. N-((1s,3s)-3-Isothiocyanatocyclobutyl)-1-(4-methoxyphenyl)azetidine-3-carboxamide

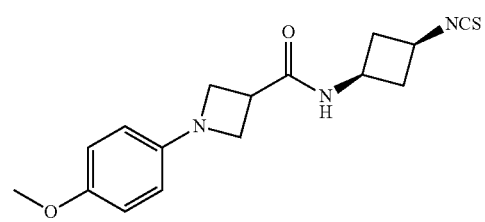

Scheme 3

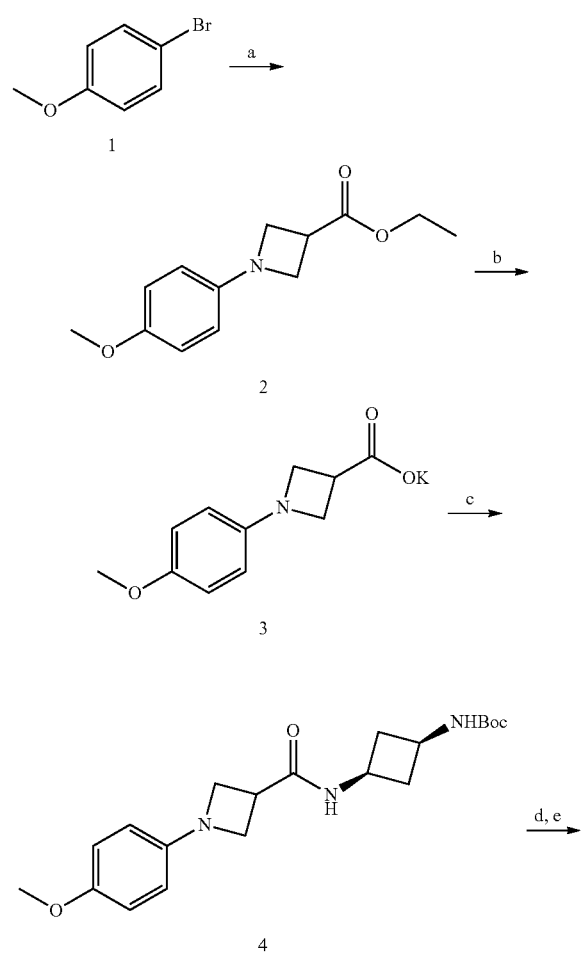

-continued

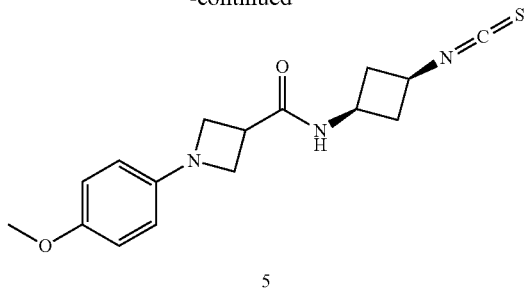

5

Reagents and Conditions: (a) Ethyl azetidine-3-carboxylate•HCl, NaOt-Bu, Pd₂(dba)₃/BINAP, PhCH₃, 100° C.; (b) KOH, EtOH; (c) EDAC/HOBt, EtN(i-Pr)₂, cat. DMF, CH₂Cl₂, rt, 12 h; (d) HCl/dioxane; (e) 1,1'-thiocarbonyldi 2-[1H]-pyridone, EtN(i-Pr)₂, CH₂Cl₂, rt, 2 h.

Step a): Ethyl 1-(4-methoxyphenyl)azetidine-3-carboxylate. To a stirring suspension of a mixture of ethyl azetidine-3-carboxylate.HCl (500.0 mg, 3.0 mmol) in toluene at 0° C., under argon was added NaO-t-Bu (576.0 mg, 6.0 mmol). The suspension was stirred at room temperature (10 minutes), 4-bromoanisole (280.0 mg, 1.5 mmol) and BINAP (99.0 mg, 0.15 mmol) were added. The resulting suspension was bubbled with argon (10 minutes), Pd₂(dba)₃ (73.0 mg, 0.08 mmol) was added, the mixture was bubble with argon for additional 10 minutes and heated at 100° C. for 6 hours. After cooling, the reaction mixture was poured into water. The aqueous layer was extracted with ethyl acetate (2×20 mL). The combined organic phases were washed with brine, dried over MgSO₄, filtered and concentrated under reduced pressure. The crude material was purified by column chromatography over silica gel (10-15% EtOAc/hexane) to give 179.0 mg (48% yield) of ethyl 1-(4-methoxyphenyl)azetidine-3-carboxylate. ¹H NMR (500 MHz, CDCl₃): δ 6.82 (d, J=9.0 Hz, 2H); 6.44 (d, J=9.0 Hz, 2H); 4.19 (q, J=7.0 Hz, 2H); 4.03 (t, J=7.0 Hz, 2H); 3.95 (t, J=7.0 Hz, 2H); 3.75 (s, 3H); 3.51-3.58 (m, 1H); 1.28 (t, J=7.0 Hz, 3H).

Step b). 1-(4-methoxyphenyl)azetidine-3-carboxylic acid potassium salt. A mixture of ethyl 1-(4-methoxyphenyl) azetidine-3-carboxylate (166.0 mg, 0.7 mmol) and KOH (78.0 mg, 1.4 mmol) in EtOH/H₂O (9.5/0.5, 10.0 mL) was stirred at room temperature (6 hours). The solvent was removed under reduced pressure and the residue dried under vacuum to give 221 mg of potassium 1-(4-methoxyphenyl) azetidine-3-carboxylate, which was used in the next step without purification.

Step c): tert-Butyl ((cis)-3-(1-(4-methoxyphenyl)azetidine-3 carboxamido)cyclobutyl) carbamate. A similar procedure to that described in the synthesis of N-(cis-(3-isothiocyanatocyclobutyl))-5-methoxy-[2,3'-bipyridine]-6'-carboxamide step a) was followed by using potassium 1-(4-methoxyphenyl)azetidine-3-carboxylate (104 mg, 0.4 mmol), N-ethyl-N-diisopropyl amine (103.0 mg, 0.8 mmol) in anhydrous dichloromethane (10 mL), DMF (0.02 mL), EDAC-HCl (96.0 mg, 0.5 mmol), and HOBt (67.0 mg, 0.5 mmol). The crude material was purified by column chromatography (ethyl acetate/hexane, 1:3) to give title compound tert-butyl ((cis)-3-(1-(4-methoxyphenyl)azetidine-3 carboxamido)cyclobutyl) carbamate (111.0 mg, 74% yield). ¹H NMR (500 MHz, CDCl₃): δ 6.82 (d, J=9.0 Hz, 2H); 6.44 (d, J=9.0 Hz, 2H); 6.18 (brs, 1H); 4.65-4.75 (m, 1H); 3.96 (t, J=7.0 Hz, 2H); 3.90 (t, J=7.0 Hz, 2H); 3.75 (s, 3H); 3.32-3.20 (m, 1H); 2.83-2.78 (m, 2H); 1.94-1.84 (m, 2H); 1.43 (s, 9H).

Steps d, e): N-((cis)-3-isothiocyanatocyclobutyl)-1-(4-methoxyphenyl)azetidine-3-carboxamide. A similar procedure to that described in the synthesis of N-(cis-(3-isothiocyanatocyclobutyl))-5-methoxy-[2,3'-bipyridine]-6'-carboxamide step c) and step d) was followed by using tert-butyl ((cis)-3-(1-(4-methoxyphenyl)azetidine-3 carboxamido)cyclobutyl) carbamate (75.0 mg, 0.2 mmol) to produce N-((cis)-3-isothiocyanatocyclobutyl)-1-(4-methoxyphenyl)azetidine-3-carboxamide (39.0 mg, 61%). ¹H NMR (500 MHz, CDCl₃): δ 6.84 (d, J=9.0 Hz, 2H); 6.54 (d, J=9.0 Hz, 2H); 6.50 (brs, 1H); 4.25-4.18 (m, 1H); 4.17-4.06 (m, 2H); 4.05-3.97 (m, 2H); 3.87-3.82 (m, 1H); 3.77 (s, 3H); 3.43-3.32 (m, 1H); 2.95-2.88 (m, 2H); 2.20-2.18 (m, 2H).

Example 37. N-((1s,3s)-3-isothiocyanatocyclobutyl)-3-(4-methoxyphenyl)bicyclo[1.1.1]pentane-1-carboxamide

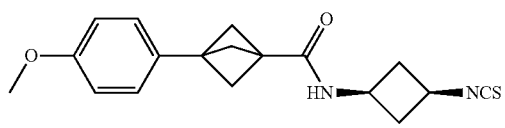

Scheme 4

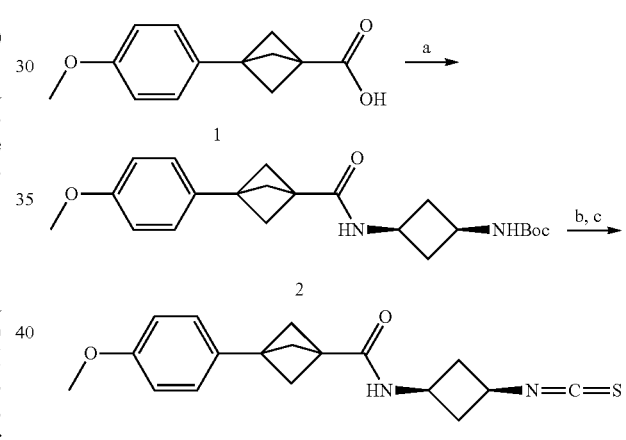

Reagents and Conditions: (a) 2, EDAC/HOBt, EtN(i-Pr)₂, cat. DMF, CH₂Cl₂, rt, 12 h; (b) HCl/dioxane; (d) 1,1'-thiocarbonyldi 2-[1H]-pyridone, EtN(i-Pr)₂, CH₂Cl₂, rt, 2 h Step a): tert-Butyl((cis)-3-(3-(4-methoxyphenyl)bicyclo [1.1.1]pentane1carboxamido) cyclobutyl) carbamate. A similar procedure to that described for the synthesis of N-(cis-(3-isothiocyanatocyclobutyl))-5-methoxy-[2,3'-bipyridine]-6'-carboxamide step a) was followed by using 3-(4-methoxyphenyl)bicycle[1.1.1]pentane carboxylic acid (65.0 mg, 0.3 mmol), N-ethyl-N-diisopropylamine (103.0 mg, 0.8 mmol) in anhydrous dichloromethane (5.0 mL), DMF (0.01 mL), EDAC-HCl (77.0 mg, 0.4 mmol), and HOBt (54.0 mg, 0.4 mmol). The crude material was purified by column chromatography (ethyl acetate/hexane, 1:1) to give tert-butyl((cis)-3-(3-(4-methoxyphenyl)bicyclo[1.1.1] pentane1carboxamido) cyclobutyl) carbamate (71.0 mg, 61% yield). ¹H NMR (400 MHz, CDCl₃): δ 7.14 (d, J=8.0 Hz, 2H); 6.85 (d, J=8.0 Hz, 2H); 5.75-5.63 (brs, 1H); 4.80-4.73 (m, 1H); 4.15-4.02 (m, 1H); 3.79 (s, 3H); 2.85-2.70 (m, 2H); 2.23 (s, 6H); 1.98-1.82 (m, 2H); 1.44 (s, 9H).

Steps b, c): N-((cis)-3-isothiocyanatocyclobutyl)-3-(4-methoxyphenyl)bicyclo[1.1.1]pentane-1-carboxamide. A similar procedure to that described for the synthesis of N-(cis-(3-isothiocyanatocyclobutyl))-5-methoxy-[2,3'-bipyridine]-6'-carboxamide step c) and step d) was followed by using tert-butyl((cis)-3-(3-(4-methoxyphenyl)bicyclo[1.1.1]pentane1carboxamido) cyclobutyl) carbamate (58.0 mg, 0.15 mmol) to produce N-((cis)-3-isothiocyanatocyclobutyl)-3-(4-methoxyphenyl)bicyclo[1.1.1]pentane-1-carboxamide (26.0 mg, 52%). $^1$H NMR (400 MHz, CDCl$_3$): δ 7.14 (d, J=8.0 Hz, 2H); 6.67 (brs, 1H); 5.75-5.63 (brs, 1H); 4.25-4.13 (m, 1H); 3.90-3.81 (m, 1H); 3.80 (s, 3H); 2.95-2.70 (m, 2H); 2.25 (s, 6H); 2.24-2.15 (m, 2H).

Example 38. 3-(Azetidin-1-yl)-N-((1s,3s)-3-isothiocyanatocyclobutyl)-5-(4-methoxyphenyl)picolinamide

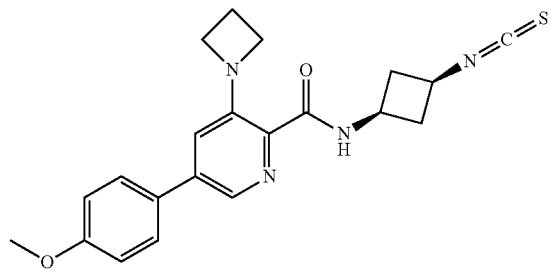 [SMILES: COc1ccc(-c2cnc(C(=O)N[C@H]3C[C@@H](N=C=S)C3)c(N3CCC3)c2)cc1]

Scheme 5

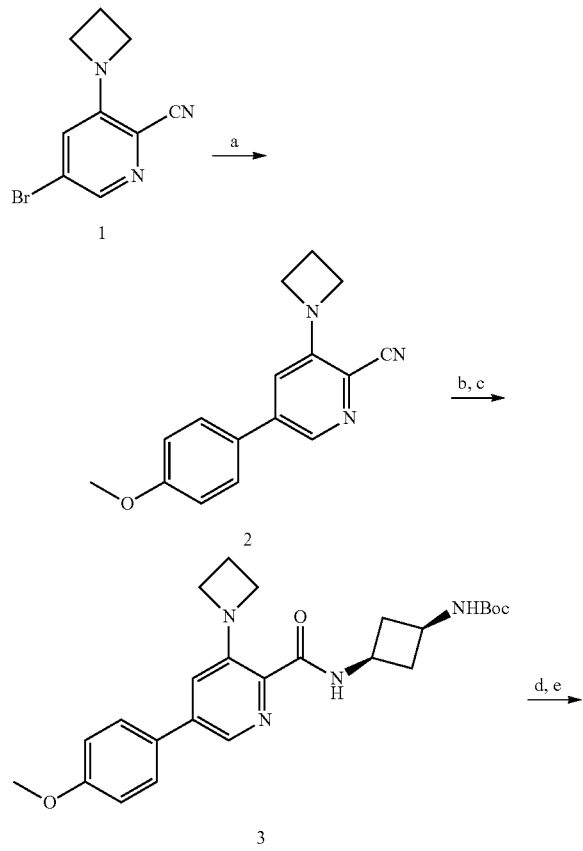

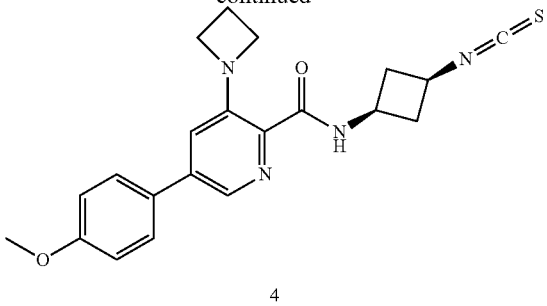

Reagents and Conditions: (a) 7, K$_2$CO$_3$, dioxane/H$_2$O, Pd(PPh$_3$)$_4$, 80° C., 4 h.; (b) NaOH, EtOH/H$_2$O, reflux 4 days; (c) 2, EDAC/HOBt, EtN(i-Pr)$_2$, cat DMF, CHCl$_3$, rt, 12 h; (d) HCl/Dioxane; (e) 1,1'thiocarbonyldi 2-[1H]-pyridone, EtN(i-Pr)$_2$, CH$_2$Cl$_2$, rt, 2 h Step a): 3-(Azetidin-1-yl)-5-(4-methoxyphenyl)picolinonitrile. To a stirring solution of 3-(azetidin-1-yl)-5-bromopicolinonitrile (238.0 mg, 1.0 mmol) in dioxane (5 mL) was added 4-methoxphenylboronic acid 7 (182.0 mg, 1.2 mmol) and a solution of K$_2$CO$_3$ (331.0 mg, 2.4 mmol) in water (2.5 mL), the mixture bubbled with argon (10 minutes), treated with Pd(PPh$_3$)$_4$ (4.5 mg 0.02 mmol) and heated at 80° C. for 2 hours. The mixture was cooled to room temperature, diluted with EtOAc (10.0 mL) and water (3 mL). The aqueous layer was further extracted with EtOAc (10 mL). The combined organic layers were dried (MgSO$_4$) and the solvent evaporated under reduced pressure to give a crude material which was purified by column chromatography (35% EtOAc/65% hexane) to afford 3-(azetidin-1-yl)-5-(4-methoxyphenyl)picolinonitrile (243.0 mg, 91.6% yield). $^1$H NMR (500 MHz, CDCl$_3$): δ 8.20 (d, J=2.0 Hz, 1H); 7.50 (d, J=9.0 Hz, 2H); 7.01 (d, J=9.0 Hz, 2H); 6.81 (d, J=2.0 Hz, 1H); 4.29 (t, J=7.0 Hz, 4H); 3.86 (s, 3H); 2.50-2.43 (m, 2H).

Step b): tert-Butyl ((cis)-3-(3-(azetidin-1-yl)-5-(4 methoxyphenyl)picolinamido)cyclobutyl) carbamate. A solution of 3-(azetidin-1-yl)-5-(4-methoxyphenyl)picolinonitrile (240 mg, 0.9 mmol) in EtOH/H$_2$O (1:1, 4 mL) was treated with NaOH (360 mg, 9.0 mmol). The mixture was refluxed for 4 days. The solvent was removed under reduced pressure and the residue dried under high vacuum to give 3-(azetidin-1-yl)-5-(4-methoxyphenyl)picolinic acid (595 mg) which was used in the next step without further purification. $^1$H NMR (500 MHz, CDCl$_3$): δ 8.58 (s, 1H); 8.10 (s, 1H); 7.61 (d, J=8.0 Hz, 2H); 7.10 (d, J=8.0 Hz, 2H); 3.90 (t, J=7.0 Hz, 4H); 3.79 (s, 3H); 2.30-2.20 (m, 2H).

Step c). A solution of 16 (240 mg, 0.9 mmol) in EtOH/H2O (1:1, 4 mL) was treated with NaOH (360 mg, 9.0 mmol). The mixture was heated at reflux for 4 days. The solvent was removed under reduced pressure and the residue dried under high vacuum to give a crude carboxylic acid sodium salt (595 mg) used in the next step without further purification. $^1$H NMR (500 MHz, CDCl$_3$): δ 8.58 (s, 1H); 8.10 (s, 1H); 7.61 (d, J=8.0 Hz, 2H); 7.10 (d, J=8.0 Hz, 2H); 3.90 (t, J=7.0 Hz, 4H); 3.79 (s, 3H); 2.30-2.20 (m, 2H).

Step d): N-((1s,3s)-3-aminocyclobutyl)-3-(azetidin-1-yl)-5-(4-methoxyphenyl)picolinamide. A similar procedure to that described for the synthesis of N-(cis-(3-isothiocyanatocyclobutyl))-5-methoxy-[2,3'-bipyridine]-6'-carboxamide step c) was followed by using a crude carboxylic acid salt (step b), EDAC (10.0 eq), HOBt (10.0 eq.), EtN(i-Pr)$_2$ (10.0 eq.) and 2 (94.0 mg 0.5 mmol), DMF (0.5 mL) and CHCl$_3$ (20 mL) to give N-((1s,3s)-3-aminocyclobutyl)-3-(azetidin-1-yl)-5-(4-methoxyphenyl)picolinamide, 102 mg, 25% yield). $^1$H NMR (500 MHz, CDCl$_3$): 8.10 (s, 1H); 7.79 (brs, 1H) 7.53 (d, J=8.0 Hz, 2H); 7.01 (d, J=8.0 Hz, 2H); 6.93 (s, 1H); 4.25-4.15 (m, 1H); 4.12-3.99 (m, 5H); 3.86 (s, 3H); 2.90-2.82 (m, 1H); 2.80-2.70 (m, 1H); 2.38-2.30 (m, 2H); 1.94-1.85 (m, 1H); 1.84-1.75 (m, 1H); 1.44 (s, 9H).

Step e). 3-(Azetidin-1-yl)-N-((cis)-3-isothiocyanatocyclobutyl)-5-(4-methoxyphenyl) picolinamide. A similar procedure to that described for the synthesis of N-(cis-(3-isothiocyanatocyclobutyl))-5-methoxy-[2,3'-bipyridine]-6'-carboxamide step d) was followed by using N-((1s,3s)-3-aminocyclobutyl)-3-(azetidin-1-yl)-5-(4-methoxyphenyl) picolinamide (45.0 mg, 0.1 mmol) to produce 3-(azetidin-1-yl)-N-((cis)-3-isothiocyanatocyclobutyl)-5-(4 methoxyphenyl) picolinamide (18.0 mg, 45%). $^1$H NMR (500 MHz, CDCl$_3$): δ 8.30 (brs, 1H); 7.99 (s, 1H); 7.55 (d, J=10.0, 2H); 7.18 (s, 1H); 7.02 (d, J=10.0 Hz, 2H); 4.30-4.20 (m, 1H); 3.95-3.8 (m overlapping with s at 3.87, 4H); 3.68 (t, J=7.0, 2H); 3.45 (q, J=7.0, 2H); 3.05-2.90 (m, 2H); 2.45-2.30 (m, 2H); 2.20-2.05 (m, 2H).

Example 39. 2-(1-((1s,3s)-3-Isothiocyanatocyclobutoxy)ethyl)-5-(4-methoxyphenyl)pyridine

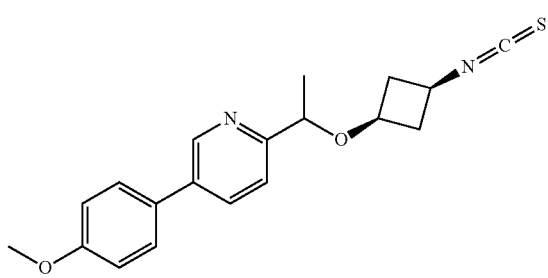 [SMILES: COc1ccc(-c2ccc(C(C)O[C@H]3C[C@@H](N=C=S)C3)nc2)cc1]

Step a): 5-Bromo-2-(1-bromoethyl) pyridine. To a solution of 5-bromo-2-ethylpyridine (1.00 g, 5.37 mmol) in 10 mL were added dichloroethane N-bromosuccinimide (0.956 mg, 5.37 mmol) and AIBN (44.1 mg, 0.050 mmol). The mixture was heated at 90° C. and stirred for 3 hours, and overnight at room temperature. The reaction mixture was washed with saturated sodium bicarbonate solution, water (2 times) and brine. After solvent removal under vacuum the crude material was used in the next step without purification. $^1$H NMR (400 MHz, CDCl$_3$) δ ppm 2.05 (d, J=6.59 Hz, 3H) 5.18 (q, J=6.59 Hz, 1H) 7.36 (d, J=8.06 Hz, 1H) 7.81 (dd, J=8.06, 2.20 Hz, 1H) 8.62 (d, J=1.47 Hz, 1H).

Step b): tert-Butyl ((1s,3s)-3-(1-(5-bromopyridin-2-yl)ethoxy)cyclobutyl)carbamate. tert-Butyl ((1s,3s)-3-hydroxycyclobutyl)carbamate (318.9 mg, 1.703 mmol) was dissolved in toluene (15 mL) and the solution was evaporated in vacuum and was dissolved in 15 ml of anhydrous THF and cooled to 5° C. To this was added 60% sodium hydride in mineral oil (103 mg, 2.555 mmol). The suspension was stirred for 15 minutes and 5-bromo-2-(1-bromoethyl) pyridine (475.0 mg, 1.793 mmol) was added. The reaction mixture was stirred at room temperature for 68 hours, and then overnight at 50° C. After removing of THF in vacuum, water was added and products were extracted twice with EtOAc, washed with water and brine and dried with MgSO$_4$. Purified by chromatography. $^1$H NMR (500 MHz, CHLOROFORM-d) δ ppm 1.55 (d, J=1.95 Hz, 3H) 1.66-1.77 (m, 1H) 1.77-1.88 (m, 1H) 2.49 (br. s., 1H) 2.72 (br. s., 1H) 3.58-3.72 (m, 2H) 4.45 (q, J=6.34 Hz, 1H) 4.58 (br. s., 1H) 7.30 (d, J=8.30 Hz, 1H) 7.79 (d, J=8.30 Hz, 1H) 8.57 (s, 1H).

Step c): tert-Butyl ((1s,3s)-3-(1-(5-(4-methoxyphenyl)pyridin-2-yl)ethoxy)cyclobutyl) carbamate. A mixture of tert-butyl ((1s,3s)-3-(1-(5-bromopyridin-2-yl)ethoxy)cyclobutyl) carbamate (83.5 mg, 0.225 mmol), (4-methoxyphenyl)boronic acid (51.3 mg, 0.337 mmol), potassium carbonate (3.8 mg, 0.675 mmol) in a mixture of DME (5 mL) and water (2 mL) was stirred in argon for 5 minutes, then flushed by argon 1 minute. To this mixture 18.3 mg Pd catalyst was added and contents were heated at 80° C. with stirring for 1 hour. The reaction mixture was diluted with 15 mL EtOAc and 20 mL of water and extracted with EtOAc (3×10 mL). After drying (MgSO$_4$) and solvent removal the crude product was subjected to chromatography. $^1$H NMR (500 MHz, CHLOROFORM-d) δ ppm 1.43 (s, 9H) 1.50 (d, J=6.83 Hz, 3H) 1.70-1.90 (m, 2H) 2.54 (br. s., 1H) 2.77 (br. s., 1H) 3.63-3.76 (m, 3H) 3.88 (s, 3H) 4.56 (q, J=6.67 Hz, 1H) 4.61 (br. s., 1H) 7.03 (d, J=8.78 Hz, 2H) 7.44 (d, J=8.30 Hz, 1H) 7.53 (d, J=8.78 Hz, 2H) 7.85 (d, J=8.30 Hz, 1H) 8.74 (s, 1H).

Step d): 2-(1-((1s,3s)-3-(Chloro-15-azaneyl)cyclobutoxy)ethyl)-5-(4-methoxyphenyl) pyridine. Tert-butyl ((1s,3s)-3-(1-(5-(4-methoxyphenyl)pyridin-2-yl)ethoxy)cyclobutyl) carbamate (76 mg, 0.205 mmol) was dissolved at 5° C. in 0.5 mL 4M solution of hydrogen chloride in dioxane. The mixture was stirred 20 minutes at that temperature and then at room temperature for 2 hours. The precipitate was separated by filtration and dried and used as is in the next step.

Step e): 2-(1-((1s,3s)-3-Isothiocyanatocyclobutoxy)ethyl)-5-(4-methoxyphenyl) pyridine. To a solution of 2-(1-((1s,3s)-3-(chloro-15-azaneyl)cyclobutoxy)ethyl)-5-(4-methoxyphenyl)pyridine (45.0 mg, 0.134 mmol) in 3 mL DCM, 38.1 mg (52.5 μl, 0.126 mmol) TEA and 52.5 mg (0.377 mmol) of 1,1'-thiocarbonylbis(pyridin-2(1H)-one) were added and mixture was stirred at room temperature for 4 hours. After solvent evaporation, the crude product was purified by chromatography. $^1$H NMR (500 MHz, CHLOROFORM-d) δ ppm 1.50 (d, J=6.83 Hz, 3H) 2.19-2.25 (m, 1H) 2.29-2.35 (m, 1H) 2.57 (td, J=11.96, 5.61 Hz, 1H) 2.83 (td, J=11.71, 5.86 Hz, 1H) 3.61 (quint, J=7.81 Hz, 1H) 3.72 (quint, J=7.08 Hz, 1H) 3.86 (s, 3H) 4.53 (q, J=6.34 Hz, 1H) 7.01 (d, J=8.78 Hz, 2H) 7.43 (d, J=8.30 Hz, 1H) 7.51 (d, J=8.78 Hz, 2H) 7.85 (dd, J=8.05, 2.20 Hz, 1H) 8.71 (d, J=1.95 Hz, 1H).

Example 40. 5-(3-Fluoro-4-methoxyphenyl)-2-(1-((1s,3s)-3-isothiocyanatocyclobutoxy)ethyl)pyridine

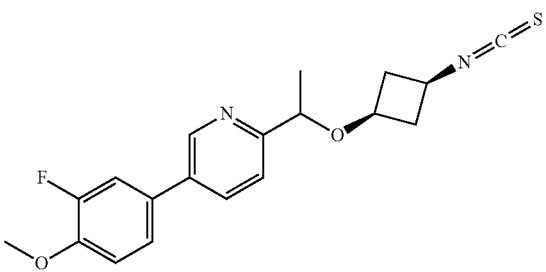 [SMILES: COc1ccc(-c2ccc(C(C)O[C@H]3C[C@@H](N=C=S)C3)nc2)cc1F]

Step a: tert-Butyl ((1s,3s)-3-(1-(5-(3-fluoro-4-methoxyphenyl)pyridin-2-yl)ethoxy)cyclobutyl)carbamate. The solution of 38.7 mg (0.1427 mmol) of tert-butyl ((1s,3s)-3-(1-(5-bromopyridin-2-yl)ethoxy)cyclobutyl) carbamate, 36.4 (0.2141 mmol) of (3-fluoro-4-methoxyphenyl)boronic acid and 59.5 mg (0.4282 mmol) potassium carbonate in mixture of 2 mL of DME and 1 mL of water was stirred in argon for 5 minutes, and then flushed in argon for 1 minute. To this mixture, 11.7 mg Pd⁰ catalyst was added and the mixture was heated at 80° C. with stirring for 1.5 hours. The reaction mixture was diluted with 5 mL of EtOAc and 10 mL of water, and extracted with EtOAc (3×5 mL). After drying and solvent removal, the crude product was subjected to chromatography. ¹H NMR (500 MHz, CHLOROFORM-d) δ ppm 1.55 (d, J=1.95 Hz, 3H) 1.66-1.77 (m, 1H) 1.77-1.88 (m, 1H) 2.49 (br. s., 1H) 2.72 (br. s., 1H) 3.58-3.72 (m, 2H) 4.45 (q, J=6.34 Hz, 1H) 4.58 (br. s., 1H) 7.30 (d, J=8.30 Hz, 1H) 7.79 (d, J=8.30 Hz, 1H) 8.57 (s, 1H).

Step b): 2-(1-((1s,3s)-3-(Chloro-15-azaneyl)cyclobutoxy)ethyl)-5-(3-fluoro-4-methoxyphenyl) pyridine. Tert-butyl ((1s,3s)-3-(1-(5-(3-fluoro-4-methoxyphenyl)pyridin-2-yl)ethoxy)cyclobutyl) carbamate (46 mg, 110 mmol) was dissolved at 5° C. in 0.5 mL 4M solution of hydrogen chloride in dioxane. The mixture was stirred 20 minutes at that temperature and then 2 hours at room temperature. The precipitate was separated by filtration and dried and used as is in the next step.

Step c): 2-(1-((1s,3s)-3-Isothiocyanatocyclobutoxy)ethyl)-5-(3-fluoro-4-methoxyphenyl) pyridine. To a solution of 15.0 mg (0.043 mmol) of 2-(1-((1s,3s)-3-(chloro-15-azaneyl)cyclobutoxy)ethyl)-5-(3-fluoro-4-methoxyphenyl) pyridine in 3 mL DCM, 12.7 mg (17.5 µl, 0.126 mmol) TEA and 17.5 mg (0.075 mmol) of 1,1'-thiocarbonylbis(pyridin-2(1H)-one) were added and the mixture was stirred at room temperature for 4 hours. After solvent evaporation, the rest was purified by chromatography. ¹H NMR (500 MHz, CHLOROFORM-d) δ ppm 1.50 (d, J=6.83 Hz, 3H) 2.18-2.25 (m, 1H) 2.30-2.35 (m, 1H) 2.58 (td, J=11.96, 5.61 Hz, 1H) 2.83 (td, J=11.71, 5.86 Hz, 1H) 3.61 (quint, J=7.81 Hz, 1H) 3.73 (quint, J=7.08 Hz, 1H) 3.95 (s, 3H) 4.54 (q, J=6.34 Hz, 1H) 7.02 (d, J=8.78 Hz, 2H) 7.07 (t, J=8.30 Hz, 1H) 7.31 (m, 1H) 7.83 (dd, J=8.05, 2.20 Hz, 1H) 8.70 (d, J=1.95 Hz, 1H).

Example 41. (1s,3S)—N-((1s,3S)-3-Isothiocyanatocyclobutyl)-3-(4-methoxyphenyl) cyclobutane-1-carboxamide

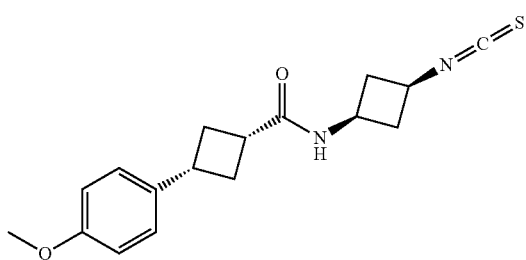 [SMILES: COc1ccc([C@H]2C[C@@H](C(=O)N[C@H]3C[C@@H](N=C=S)C3)C2)cc1]

Step a): Ethyl 3-hydroxy-3-(4-methoxyphenyl)cyclobutane-1-carboxylate. To a solution of 362.5 mg (2.550 mmol) ethyl 3-oxocyclobutane-1-carboxylate in 15 mL of anhydrous THF was added 2.7 mL (~2.6 mmol) 1 M (4-methoxyphenyl)magnesium bromide in THF at 10° C. The reaction mixture was stirred at room temperature for 2 hours and then treated with 5 mL saturated solution of NH₄Cl and extracted with EtOAc (3×15). The extracts were washed with water and brine and dried (MgSO₄). After removal of the solvents the compound was used in the next step without purification.

Step b): Ethyl 3-(4-methoxyphenyl)cyclobutane-1-carboxylate. Ethyl 3-hydroxy-3-(4-methoxyphenyl)cyclobutane-1-carboxylate, 485.0 mg (1.938 mmol) was dissolved in 30 ml of EtOH. 145 mg of 10% Pd/C was added in a high pressure vessel and the solution was flushed with H₂ and the compound subjected to hydrogenation at 30 psi H₂ pressure with vigorous agitation for 26 hours. After standard work-up and chromatography 409.3 mg ethyl 3-(4-methoxyphenyl)cyclobutane-1-carboxylate was obtained. ¹H NMR (500 MHz, CHLOROFORM-d) δ ppm 1.25-1.29 (m, 3H) 2.32-2.41 (m, 2H) 2.54-2.62 (m, 2H) 3.02-3.11 (m, 1H) 3.35-3.43 (m, 1H) 3.79 (s, 3H) 4.12-4.17 (m, 2H) 6.85 (d, J=8.78 Hz, 2H) 7.17 (d, J=8.30 Hz, 2H).

Step c): 3-(4-Methoxyphenyl)cyclobutane-1-carboxylic acid. To a solution of 409.3 mg (1.747 mmol)ethyl 3-(4-methoxyphenyl)cyclobutane-1-carboxylate in 15 mL of THF were added a solution of 100 mg (2.5 mmol) NaOH in a mixture of 5 mL of MeOH and 3 mL of water. The solution was stirred for 2.5 hours and the solvents were removed in vacuum and the rest was acidified with 2 M hydrochloric acid (5 mL). The product was extracted with DCM (3×15 mL) and was used in the next step. ¹H NMR (500 MHz, CHLOROFORM-d) δ ppm 2.36-2.47 (m, 2H) 2.57-2.67 (m, 2H) 3.08-3.18 (m, 1H) 3.36-3.47 (m, 1H) 3.79 (s, 3H) 6.86 (d, J=8.78 Hz, 2H) 7.17 (d, J=8.30 Hz, 2H).

Step d): tert-Butyl ((1s,3s)-3-(4-methoxyphenyl)cyclobutane-1-carbonyl)carbamate. A mixture of 91.4 mg (0.456 mmol) 3-(4-methoxyphenyl)cyclobutane-1-carboxylic acid, 70.8 mg (0.380 mmol) tert-butyl ((1s,3s)-3-aminocyclobutyl)carbamate, 49.9 mg (0.456 mmol) HOBt in 10 ml DCM 123 mg (165 µl, 0.951 mmol) DIPEA and 87.5 mg (0.456 mmol) of EDC was stirred at room temperature overnight. The reaction mixture was diluted with DCM, washed with water (3×15 ml) and brine. After chromatography obtained pure tert-butyl ((1s,3s)-3-(4-methoxyphenyl)cyclobutane-1-carbonyl)carbamate. ¹H NMR (500 MHz, CHLOROFORM-d) δ ppm 1.38-1.48 (m, 9H) 1.85 (d, J=7.32 Hz, 2H) 2.27-2.39 (m, 2H) 2.50 (qd, J=8.21, 2.20 Hz, 2H) 2.73-2.81 (m, 2H) 2.84 (t, J=8.78 Hz, 1H) 3.29-3.39 (m, 1H) 3.78 (s, 3H) 3.99-4.13 (m, 1H) 4.76 (br. s., 1H) 5.69 (br. s., 1H) 6.83 (d, J=8.78 Hz, 2H) 7.17 (d, J=8.30 Hz, 2H).

Step e): N-((1s,3s)-3-Aminocyclobutyl)-3-(4-methoxyphenyl)cyclobutane-1-carboxamide hydrochloride. The title compound was prepared from 35.1 mg (0.094 mmol) tert-butyl ((1s,3s)-3-(4-methoxyphenyl)cyclobutane-1-carbonyl) carbamate and 0.7 ml 4M solution of hydrogen chloride in dioxane. The 28.8 mg N-((1s,3s)-3-aminocyclobutyl)-3-(4-methoxyphenyl) cyclobutane-1-carboxamide hydrochloride was obtained. ¹H NMR (500 MHz, DEUTERIUM OXIDE) δ ppm 1.95-2.04 (m, 2H) 2.04-2.13 (m, 2H) 2.41 (qd, J=8.21, 2.68 Hz, 2H) 2.65 (dtd, J=9.76, 7.32, 7.32, 2.93 Hz, 3H) 2.91-3.02 (m, 1H) 3.25-3.36 (m, 1H) 3.48 (quin, J=7.93 Hz, 1H) 3.69 (s, 3H) 3.90-4.02 (m, 1H) 6.86 (d, J=8.78 Hz, 2H) 7.15 (d, J=8.78 Hz, 2H).

Step f): (1s,3S)—N-((1s,3S)-3-Isothiocyanatocyclobutyl)-3-(4-methoxyphenyl)cyclobutane-1-carboxamide. The title compound was prepared from 25.0 mg (0.080 mmol) of N-((1s,3s)-3-aminocyclobutyl)-3-(4-methoxyphenyl) cyclobutane-1-carboxamide hydrochloride, 25.6 mg (0.088 mmol) of 1,1'-thiocarbonylbis(pyridin-2(1H)-one) and 22.4 µl TEA in 2 ml DCM. ¹H NMR (500 MHz, CHLOROFORM-d) δ ppm 2.07-2.19 (m, 13H) 2.29-2.40 (m, 13H) 2.53 (qd, J=8.30, 2.44 Hz, 13H) 2.85-2.96 (m, 19H) 3.31-3.43 (m, 6H) 3.78 (s, 18H) 3.80-3.89 (m, 6H) 4.12-4.24 (m, 6H) 5.62 (d, J=7.32 Hz, 6H) 6.84 (d, J=8.30 Hz, 12H) 7.17 (d, J=8.30 Hz, 12H).

Example 42. 6'-(((1s,3s)-3-Isothiocyanatocyclobutoxy)methyl)-5-methoxy-2,3'-bipyridine succinate

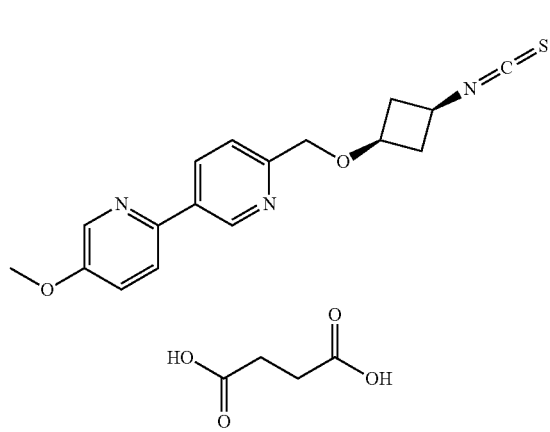

To the 5.1 mg (0.0156 mmol) of 6'-(((1s,3s)-3-isothiocyanatocyclobutoxy)methyl)-5-methoxy-2,3'-bipyridine dispersed in 0.2 ml of water, 3.7 mg (0.0312 mmol) succinic acid was added. Components were grinded until clear solution was reached and the water was evaporated at room temperature. After the water was removed the solid dried in vacuum to get 6'-(((1s,3s)-3-isothiocyanatocyclobutoxy)methyl)-5-methoxy-2,3'-bipyridine succinate. In the IR spectra of the salt the intensive absorption of the isothiocyanate functional group was present.

Example 43. 5-(3-Fluoro-4-methoxyphenyl)-2-(((1s,3s)-3-isothiocyanatocyclobutoxy)methyl)pyridine citrate

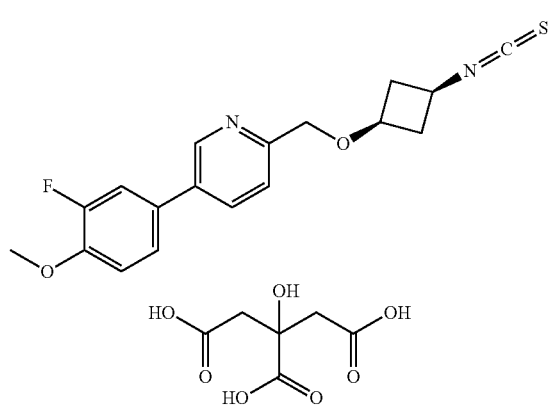

To 3 mg (0.0087 mmol) of 5-(3-fluoro-4-methoxyphenyl)-2-(((1s,3s)-3-isothiocyanatocyclobutoxy)methyl) pyridine dispersed in 0.2 ml of water, 1.7 mg (0.00885 mmol) citric acid was added. The components were grinded till a clear solution was reached and the water was evaporated at room temperature. After the water was removed the solid was dried in vacuum to get 5-(3-fluoro-4-methoxyphenyl)-2-(((1s,3s)-3-isothiocyanatocyclobutoxy) methyl)pyridine citrate. In the IR spectra of the salt the intensive absorption of the isothiocyanate functional group was present.

Example 44. Phosphinic Amide Compounds

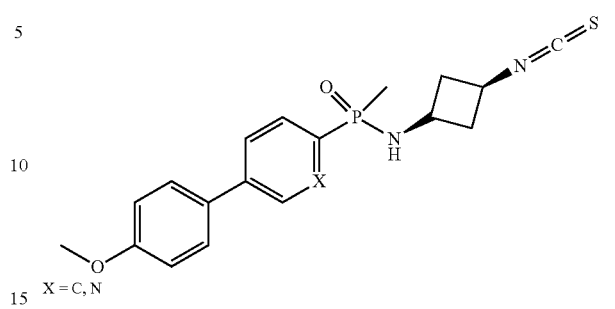

X = C, N

X=C: N-((1r,3r)-3-isothiocyanatocyclobutyl)-P-(4'-methoxy-[1,1'-biphenyl]-4-yl)-P-methylphosphinic amide
X=N: N-((1r,3r)-3-isothiocyanatocyclobutyl)-P-(5-(4-methoxyphenyl)pyridin-2-yl)-P-methylphosphinic amide The phosphinic acid compounds named and depicted above can be prepared according to the following reaction scheme.

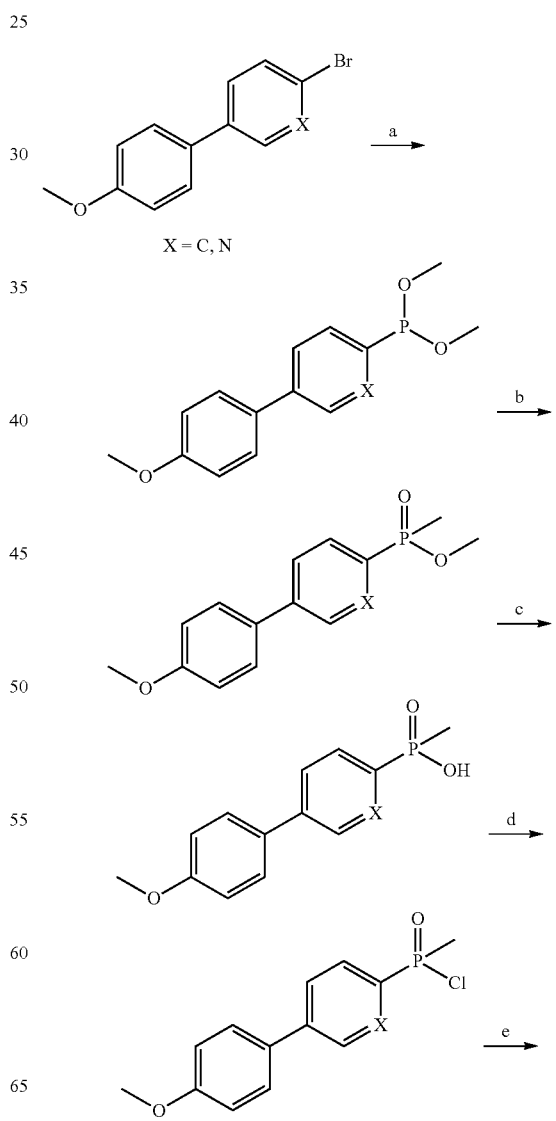

-continued

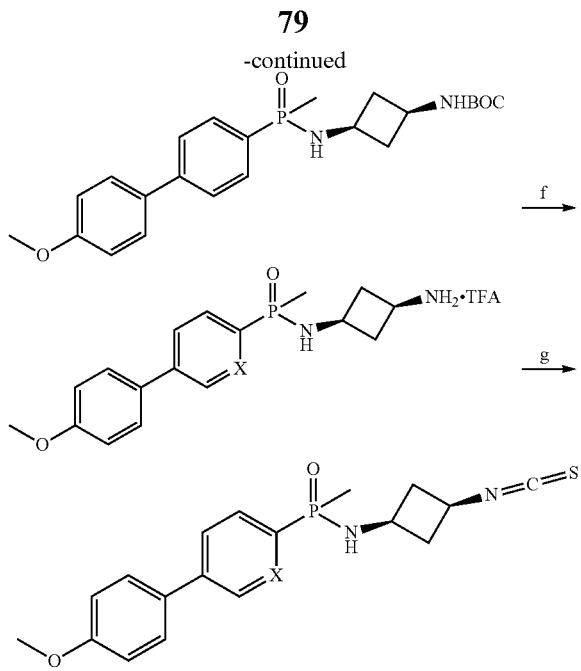

Reagents: (a) n-BuLi, dimethyl phosphorochloridite; (b) MeI, reflux; (c) HCl, H₂O; (d) SOCl₂, CH₂Cl₂; (e) isopropyl ((1s,3s)-3-aminocyclobutyl)carbamate, Et₃N; (f) TFA, CH₂Cl₂; (g) 1,1'thiocarbonylbis(pyridin-2(1H)-one), Et3N

Example 45. Evaluation of NAAA Inhibition of Test Compounds NAAA Assay

In order to have an assay method more conducive to high-throughput screening than those published for measuring the NAE hydrolyzing activity of NAAA [Proc. Natl. Acad. Sci. USA. 2009; 106(49):20966-71], the fluorogenic PEA analog N-(4-methyl coumarin)palmitamide (PAMCA), which is hydrolyzed to fluorescent 7-amino-4-methyl coumarin (AMC) and palmitic acid, was developed. [J. Proteome Res. 2012; 11(2):972-981], [PloS One. 2012; 7: e43877]. For three point concentration inhibition assays with hNAAA the following procedure was used. Purified activated NAAA (final concentration of 0.25 μg/mL) was incubated in assay buffer (100 mM citrate-phosphate buffer, pH 4.5, 3 mM DTT, 0.1% Triton X-100, 0.05% BSA, and 150 mM NaCl) made up to a total volume of 180 μL, followed by addition of the compound dissolved in 10 μL DMSO (along with DMSO neat for the control sample) with the final concentrations for each compound of 100, 10, and 1 μM, in triplicate on a 96 well plate. These samples were allowed to incubate for 15 min at room temperature and then 10 μL of a PAMCA stock solution in DMSO (final PAMCA concentration [5 μM]) was added. After 5 minutes of agitation on a shaking plate, the reaction was allowed to proceed at 37° C. for 120 minutes, with fluorescence readings taken every 10 minutes at a wavelength of 460 nm (using an excitation wavelength of 360 nm) on a Synergy HT Plate Reader using Gen5 software from Bio-Tek. The enzyme activity was calculated by converting the relative fluorescence units to AMC formed, using a standard curve of AMC.

For compounds that inhibit hNAAA in range IC₅₀<1 μM, full inhibition curves using eight different concentrations of inhibitor (8 point assay) were generated. The assay procedure used was the same as the three point assay. For ostensibly covalent compounds (as observed by a significant decrease in the slope of a plot of fluorescence vs. time in three point screen), samples were allowed to incubate for 2 hours at 37° C., instead of 15 minutes, before addition of 10 μL of a PAMCA stock solution in DMSO for a final PAMCA concentration of 5 μM. After 5 minutes of agitation on a shaking plate, the reaction was allowed to proceed at 37° C. for 120 minutes. Inhibition constants were calculated using pro Fit software (Quantum Soft, Uetikon am See, Switzerland) and a Levenberg-Marquardt algorithm.

The $k_{inact}$ and $K_I$ are routinely determined for the more potent (IC₅₀<10 nM) covalent inhibitors. This fluorescence-based assay was performed in a similar manner to the eight point assay above with the following exceptions noted here. The concentration range of compound used was 1 to 100 nM, and the compound was mixed with the PAMCA substrate (final concentration of 12.4 μM=2×$K_m$) on the 96-well plate and incubated for 15 minutes at 37° C. Then the enzyme in assay buffer (warmed to 37° C.) was added to the wells containing the compound and substrate, vigorously shaken for 5 seconds, and fluorescence readings initiated immediately (data was collected for 30 minutes at 60 second intervals). The data for each inhibitor concentration was fit to a first order equation (Eq. 1) shown below in order to determine $k_{observed}$ ($k_{obs}$), where $F_t$ is the fluorescence at time t, $F_0$ is the fluorescence at t=infinite time, $F_1$ is the total fluorescence change, and $k_{obs}$ is the first order rate constant for enzyme inactivation. To determine the inhibitor dissociation constant ($K_I$) and the first order rate constant for enzyme inactivation at infinite inhibitor concentration ($k_{inact}$), the $k_{obs}$ values for each [I] obtained above were fitted to a curve according to Eq. 2, which simplifies to Eq. 3 at [S]=2×$K_m$ as used in this experiment. These curves were fit using pro Fit software (Quantum Soft, Uetikon am See, Switzerland) and a Levenberg-Marquardt algorithm.

$$F_t = F_0 - F_1 e^{-k_{obs}t} \qquad [1]$$

$$k_{obs} = \frac{k_{inact}[I]}{[I] + K_I\left(1 + \frac{[S]}{K_m}\right)} \qquad [2]$$

$$k_{obs} = \frac{k_{inact}[I]}{[I] + 3(K_I)} \qquad [3]$$

For Table 4, the NAAA inhibition as IC₅₀ μM index is as follows: A=0.01 μM-0.1 μM; B=0.11 μM-1.00 μM; C=>1.00 μM.

TABLE 4

| Example No. | NAAA Inhibition IC₅₀ μM |
|---|---|
| 1 | C |
| 2 | B |
| 3 | A |
| 4 | C |
| 5 | C |
| 6 | B |
| 7 | A |
| 8 | A |
| 9 | C |
| 10 | C |
| 11 | C |
| 12 | B |
| 13 | B |
| 14 | A |
| 15 | A |
| 16 | A |
| 17 | B |

TABLE 4-continued

| Example No. | NAAA Inhibition IC$_{50}$ µM |
|---|---|
| 18 | A |
| 19 | A |
| 20 | B |
| 21 | A |
| 22 | B |
| 23 | B |
| 24 | C |
| 25 | A |
| 26 | A |
| 27 | A |
| 28 | A |
| 29 | A |
| 30 | A |
| 31 | A |
| 32 | A |
| 33 | A |
| 34 | A |
| 35 | B |
| 36 | B |
| 37 | B |
| 38 | B |
| 39 | A |
| 40 | B |
| 41 | A |
| 42 | A |
| 43 | A |

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

The invention claimed is:

1. A compound represented by the following structural formula:

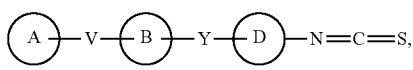

(I)

or a pharmaceutically acceptable salt thereof, wherein:
Ring A is absent, cycloalkyl, aryl, heterocyclyl or heteroaryl;
V is absent, —O—, —N(R$^{10}$)—, —S(O)$_2$—, —S(O)—, —C(O)—, —C(O)N(R$^{10}$)— or —C(R$^{11}$)(R$^{12}$);
R$^{10}$ is —H or C$_1$-C$_4$ alkyl;
R$^{11}$ and R$^{12}$ are each independently —H, C$_1$-C$_4$ alkyl, cycloalkyl, aryl, heterocyclyl or heteroaryl, or taken together with the carbon atom to which they are attached, form a saturated or unsaturated ring;
B is C$_1$-C$_6$ alkylene, C$_1$-C$_6$ alkenylene, C$_1$-C$_6$ alkynylene, cycloalkylene, arylene, heterocyclylene or heteroarylene;
Y is —C(O)N(R$^{13}$)—, —C(O)O—, —S(O$_2$)N(R$^{13}$)—, —S(O$_2$)O—, —P(O)(R$^{14}$)N(R$^{13}$)—, —P(O)(R$^{14}$)O—, —OC(O)N(R$^{13}$)—, —OC(O)O— or —N(R$^{13}$)C(O)N(R$^{13}$)—;
each R$^{13}$ is independently —H or C$_1$-C$_4$ alkyl;
R$^{14}$ is C$_1$-C$_4$ alkyl; and
Ring D is C$_3$-C$_7$ cycloalkyl.

2. The compound of claim 1, wherein Ring A is phenyl or pyridinyl.

3. The compound of claim 1, wherein V is absent.

4. The compound of claim 1, wherein B is phenylene or pyridinylene.

5. The compound of claim 1, wherein Y is —C(O)N(R$^{13}$)—, —S(O$_2$)N(R$^{13}$)— or —P(O)(R$^{14}$)N(R$^{13}$)—.

6. The compound of claim 1, represented by the following structural formula:

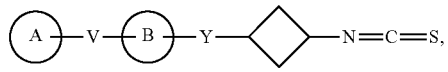

(II)

or a pharmaceutically acceptable salt thereof.

7. The compound of claim 6, represented by the following structural formula:

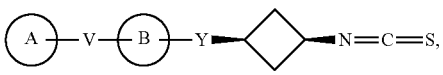

(IIa)

or a pharmaceutically acceptable salt thereof.

8. The compound of claim 1, represented by the following structural formula:

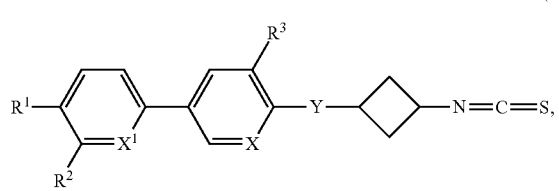

(III)

or a pharmaceutically acceptable salt thereof, wherein:
X and X$^1$ are each independently —C(R$^{15}$)— or —N—;
R$^{15}$ is —H or halo;
R$^1$ is C$_1$-C$_4$ alkoxy;
R$^2$ is —H or halo; and
R$^3$ is —H or halo.

9. The compound of claim 8, represented by the following structural formula:

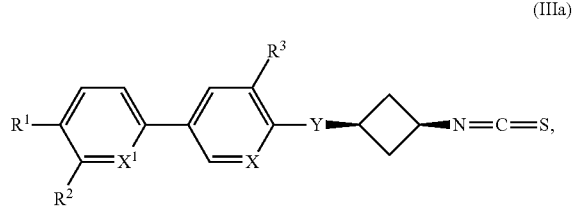

(IIIa)

or a pharmaceutically acceptable salt thereof.

10. The compound of claim 8, wherein X is —C(H)— and X$^1$ is —C(H)—.

11. The compound of claim 8, wherein X is —N— and X$^1$ is —C(H)—.

12. The compound of claim 8, wherein $R^1$ is —$OCH_3$.

13. A compound represented by any one of the following structural formulas:

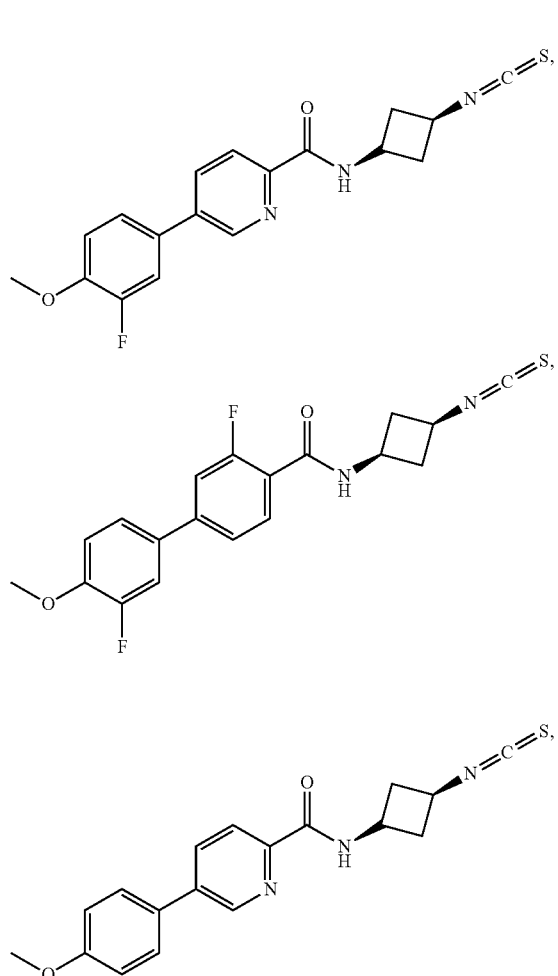

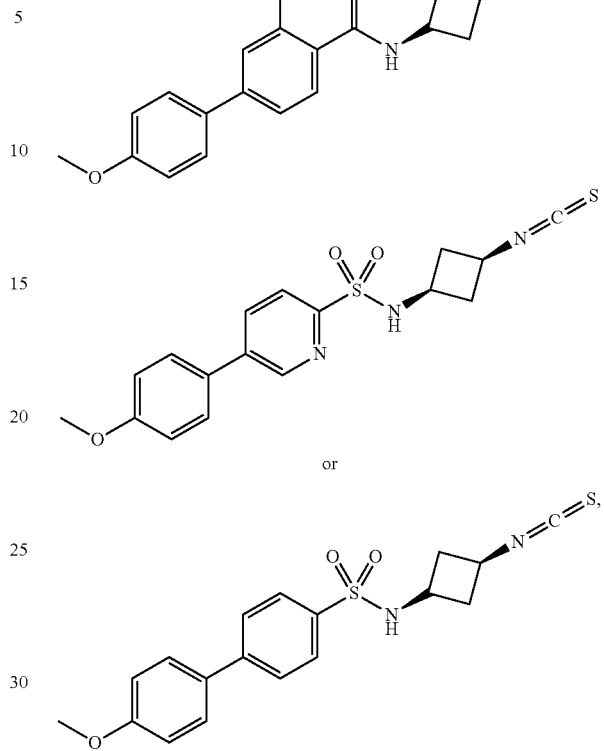

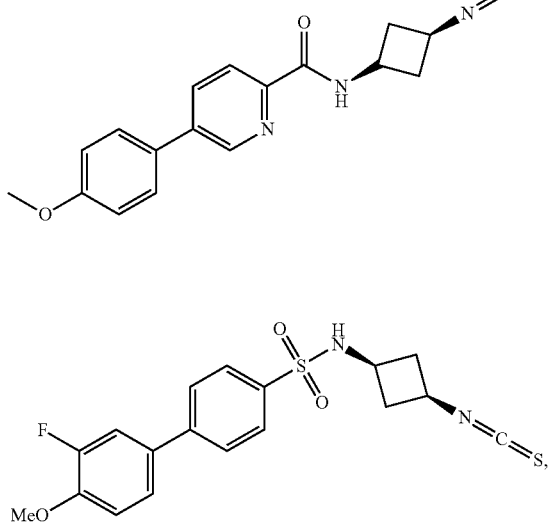

or a pharmaceutically acceptable salt of any of the foregoing.

14. A composition comprising a compound of claim 1, or a pharmaceutically acceptable salt thereof, and a pharmaceutically acceptable carrier.

15. A method for inhibiting N-acylethanolamine hydrolyzing acid amidase, comprising contacting N-acylethanolamine hydrolyzing acid amidase with a compound of claim 1, or a pharmaceutically acceptable salt thereof.

16. A method of treating a disease, disorder or condition selected from an inflammatory gastrointestinal motility disorder, irritable bowel syndrome or an inflammatory bowel disorder in a subject in need thereof, comprising administering to the subject an effective amount of a compound of claim 1, or a pharmaceutically acceptable salt thereof.

17. The method of claim 16, wherein the disease, disorder or condition is ulcerative colitis.

18. The method of claim 16, wherein the disease, disorder or condition is Crohn's disease.

* * * * *